United States Patent [19]

Taguchi et al.

[11] Patent Number: 5,974,108
[45] Date of Patent: Oct. 26, 1999

[54] X-RAY CT SCANNING APPARATUS

[75] Inventors: Katsuyuki Taguchi; Hiroshi Aradate, both of Tochigi, Japan

[73] Assignee: Kabushiki Kaisha Toshiba, Kawasaki, Japan

[21] Appl. No.: 08/773,324

[22] Filed: Dec. 24, 1996

[30] Foreign Application Priority Data

Dec. 25, 1995 [JP] Japan ................................. 7-337123

[51] Int. Cl.$^6$ ........................................................ A61B 6/03
[52] U.S. Cl. ................................. 378/4; 378/15; 378/901
[58] Field of Search .................. 378/15, 4, 901

[56] References Cited

U.S. PATENT DOCUMENTS

| | | | |
|---|---|---|---|
| 4,965,726 | 10/1990 | Heuscher et al. | 378/19 |
| 5,396,418 | 3/1995 | Heuscher | 378/15 |
| 5,430,783 | 7/1995 | Hu et al. | 378/15 |
| 5,485,493 | 1/1996 | Heuscher et al. | 378/15 |
| 5,541,971 | 7/1996 | Saito | 378/15 |

FOREIGN PATENT DOCUMENTS

| | | |
|---|---|---|
| 4-30300 | 5/1992 | Japan . |
| 4-224736 | 8/1992 | Japan . |
| 6-125890 | 5/1994 | Japan . |
| 8-167026 | 6/1996 | Japan . |

*Primary Examiner*—David Vernon Bruce
*Attorney, Agent, or Firm*—Oblon, Spivak, McClelland, Maier & Neustadt, P.C.

[57] ABSTRACT

An X-ray CT scanning apparatus comprises an X-ray source for irradiating a beam of X-ray to an object to be examined, a detector provided with at least two rows of detector elements for detecting the X-ray beam to have a real data, and a couch driver for traveling in an axial direction of the body of the object a couch on which the object is placed, in which the X-ray beam being irradiated from the X-ray source which is being rotated and simultaneously, the couch being traveled with the couch driver, the object is scanned in a helical direction so that the real data sampled by the detector is not identical in the sweep pattern to its opposite data. Two data located on both sides of the target slicing location may be selected from groups of the real data and their opposite data sampled by the detector and used to interpolate a data at the target slicing location. The group of the real data and their opposite data sampled by the detector may be filtered in the direction of slices to produce a desired data at the target slicing location. Also, a combination of the above three methods can be implemented.

24 Claims, 45 Drawing Sheets

CENTER OF ROTATION

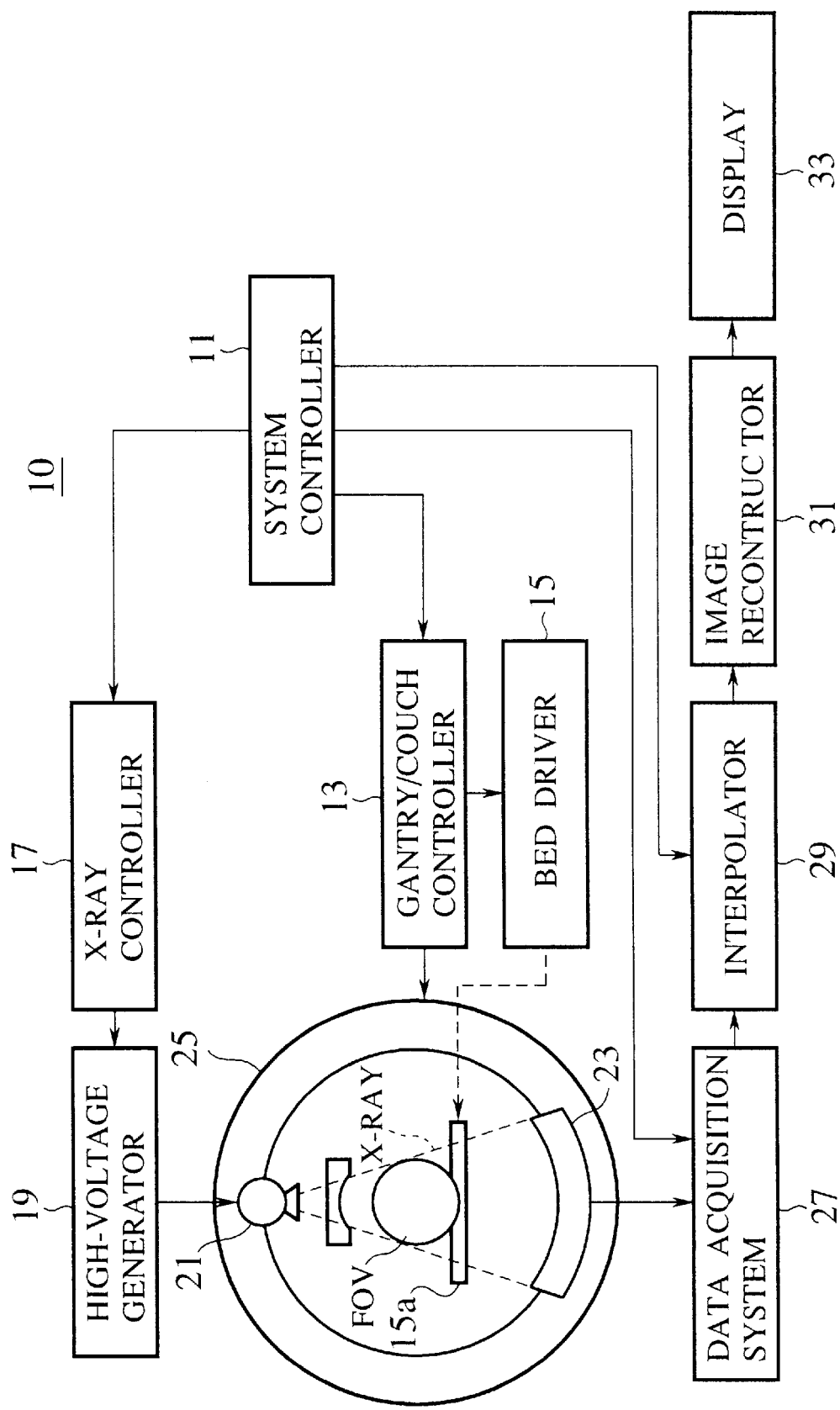

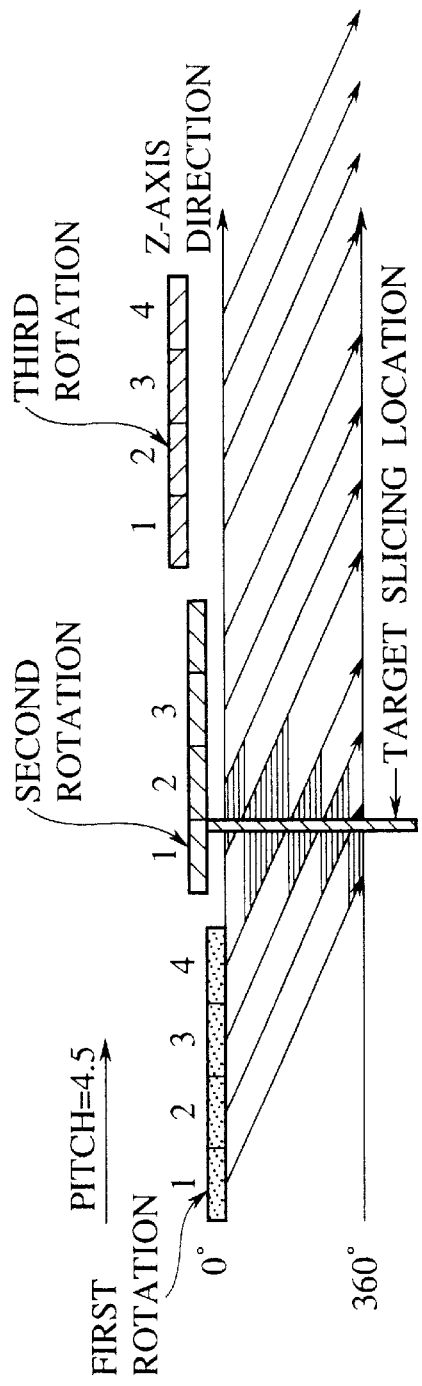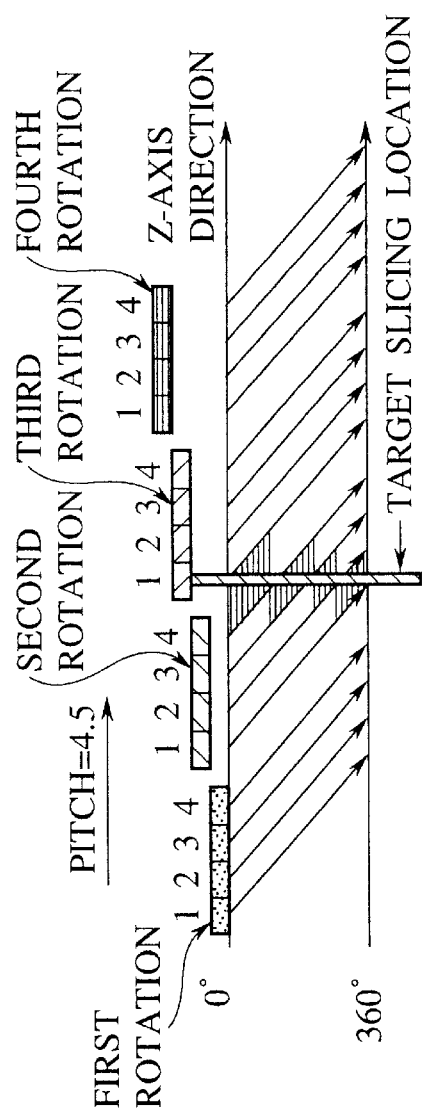

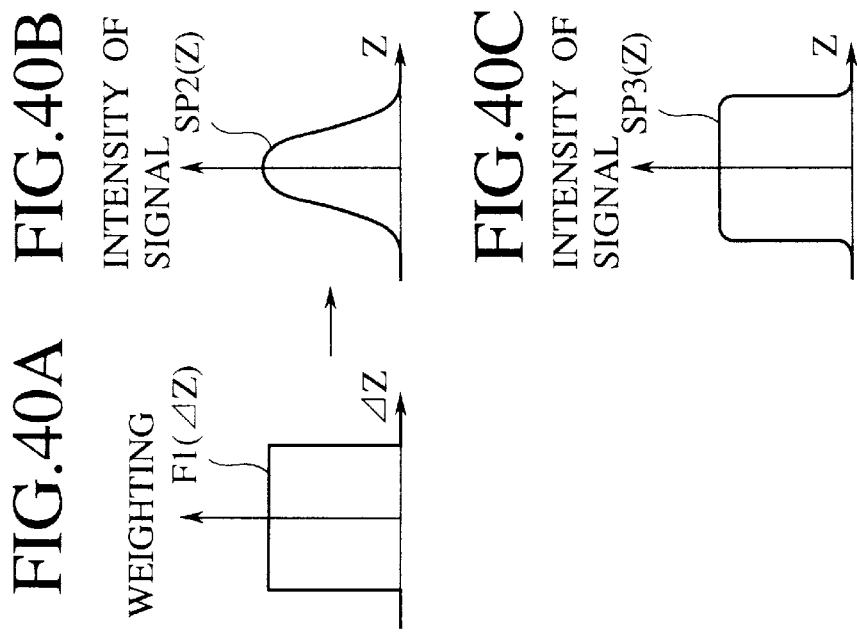

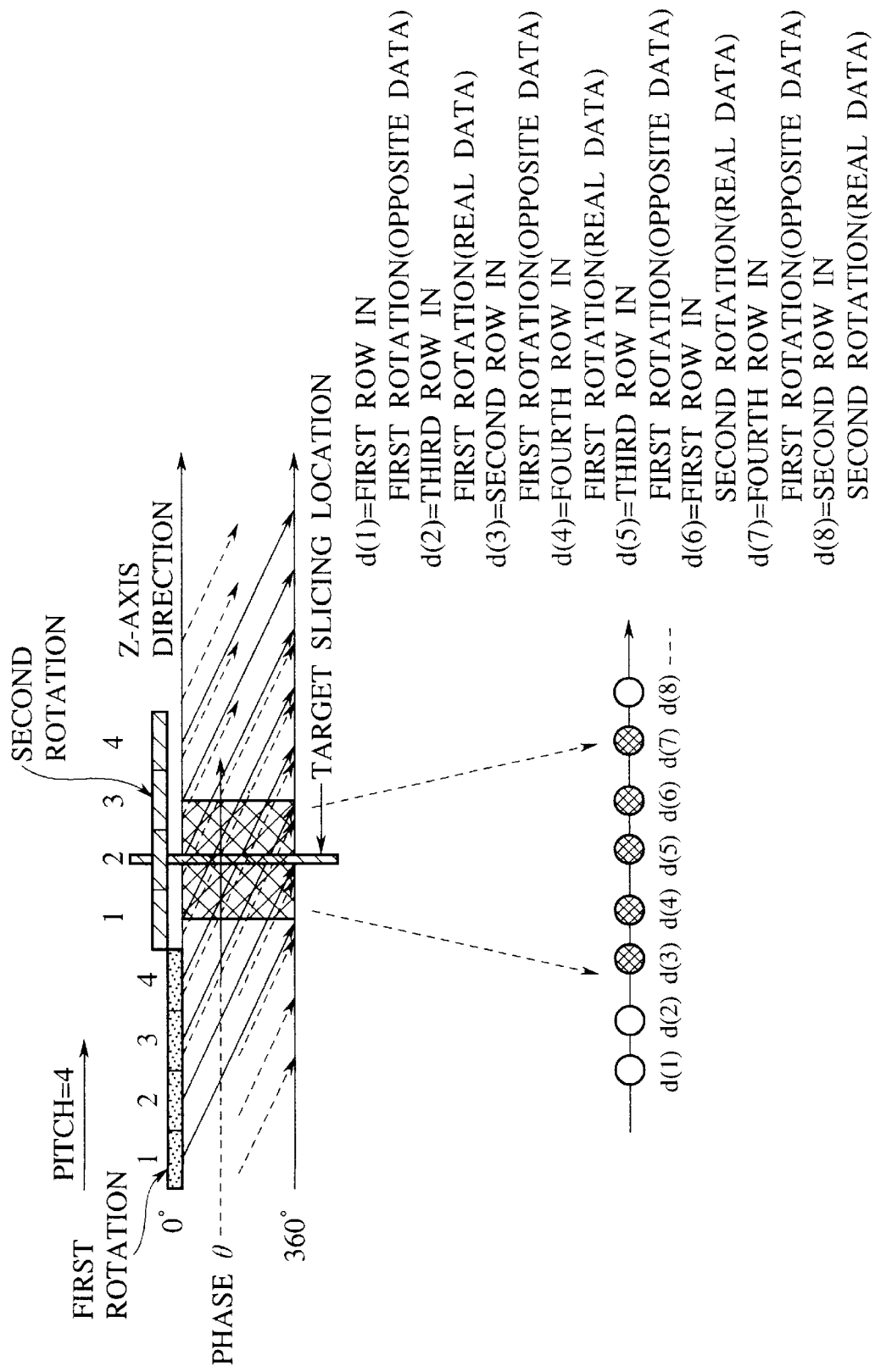

X-RAY CT SCANNING APPARATUS

BACKGROUND OF THE INVENTION

1. Field of the Invention

The present invention relates to an X-ray CT (computerized tomography) scanning apparatus and more particularly, to an X-ray CT apparatus capable of reducing undesired artifact in a reconstructed image caused by the action of helical scanning.

2. Prior Art (1) Single Slice CT

X-ray CT scanning apparatuses of the single slice type are commonly used which includes an X-ray source 101 for irradiating a fan-shaped beam of X-ray (a fan beam) and a detector 103 composed of an M number, e.g. 1000, of detector elements aligned in an arcuate or linear row, as shown in FIG. 1A. The X-ray source 101 and the detector 103 are rotated in a combination around an object to be scanned, as shown in FIG. 1A, for sampling intensity information (referred to as projection data hereinafter) of X-ray beams which have passed through the object. For example, projection data of 1000 times are sampled from one cycle of the irradiation and used for reconstruction of a visual image which will be explained later. It should be assumed that one time of the irradiation is termed one view, data of each detector element in one view is called one beam, and all the beams in one view are combined to a real data (from the detector elements).

(2) Two Different Scanning Methods

Two different scanning methods on the X-ray CT apparatus will now be explained.

One of the two scanning methods is of such a conventional type as shown in FIG. 2A where a cross section A is scanned by the source 101 which travels one full circle. If another cross section B is required to be scanned in addition to the cross section A, either a couch on which the object to be scanned is placed or a combination of the X-ray source 101 and the detector 103 is shifted to the cross section B after the completion of scanning the cross section A. The data is then collected by the combination traveling around the object. This will require a considerable length of time for scanning a series of cross sections of the object which is extended lengthwisely (along the Z axis).

The other scanning method is of such a helical scan type as shown in FIG. 2B where the X-ray source 101 and the detector 103 are rotated in circles while the couch travels lengthwisely of the object to be scanned in synchronization with the rotating movement. This allows the X-ray source 101 to scan the object as travel along a helical path. The helical scanning method is faster in the scanning speed and broader in the scanning area.

It is also assumed that the coordinate system involved is as shown at the left in FIG. 7C. The X-Y plane is a plane to be scanned by the conventional manner where the cross sections A and B fall. The Z axis is equivalent to a lengthwise direction of the object to be scanned or a slice direction in the single slice type CT scanning.

(3) Reconstruction of Conventional Scanned Image

Reconstruction of a scanned image sampled by the X-ray CT apparatus is explained below in brief. The procedure related to the conventional scanning manner consists of three steps. It is assumed that the object to be scanned is translated to a signal across the center of rotation denoted by the solid arrow shown at the upper left in FIG. 3.

[1] Sampling and compensation of data

The data is sampled by the conventional scanning method. Although the angle of rotation is shown through 90 degrees in the drawings, 360 or 180+any other fan shaping angle may be employed. Resultant patterns of projection data are as shown at the upper right in FIG. 3 and then compensated with relevant factors including the sensitivity of the detector 103, the intensity of X-ray beams, and other parameters, thus producing a raw data.

[2] Convolution with reconstructing function

The raw data sampled from all the angles are subjected to convolution of a reconstructing function. Patterns of the resultant convoluted data are shown at the lower right in FIG. 3 as have a decay at the original signal.

[3] Back projection

The convoluted data is then added to the pixels which are arrayed along the path of an X-ray beam. A result of the back projection is shown at the lower left in FIG. 3. By repeating the back projection for the convoluted data at all the angles, the original signal is reconstructed.

(4) Reconstruction of Helical Scanned Image

FIGS. 4A and 4B illustrate side-viewed patterns generated by the two, conventional and helical, scanning methods of FIGS. 2A and 2B respectively. The horizontal axis represents the slice direction (along the Z-axis) and the vertical axis is a phase (angle) of the rotation. The sampling locations are denoted by the arrows. Those drawings are referred to as "scan diagrams".

In the conventional scanning method of FIG. 4A, data at the target slicing location is sampled through 360 degrees of the phase by the prescribed step of [1] allowing the reconstruction of an image in the steps [1] to [3].

The helical scanning method of FIG. 4B however permits a helical scanning action which samples one view at the target slicing location. It is hence needed for interpolation along the Z-axis of the raw data instead of the step [1] before the steps [2] and [3] are executed. Typical methods of the interpolation for the single-slice type CT scanning are as follows:

(a) 360-degree interpolation

The 360-degree interpolation is shown in FIG. 5A where the real data of two views which are in phase with each other and designated on both sides of the target slicing location are used for linear interpolation with an inverse of the ratio of distance between the slicing location and the sampling location.

For example, if the target slicing location is expressed by Z=Z0 (at the z coordinate point of the slicing plane), its scanned data is one view at zero of the phase. For sampling data at a phase point θ, the two real data 1 and 2 on the upper and lower sides of the slicing location respectively are selected and used for linear interpolation with an inverse of the ratio of distance between their sampling location and the slicing location Z(in the z coordinate). By repeating this process, the interpolated projection data throughout the phase is obtained.

(b) Counter beam interpolation

This employs an opposite beam of imaginary data, so called "180° LI". If the X-ray source is located at the black point as shown in FIG. C, scanning beams incident on the detector elements are denoted by the arrows of the real line. The irradiating path of the beam 1 at the left side is identical to that of a beam from the X-ray source located at the white point. The beam irradiated from the white point and denoted by the dotted arrow is hence called an opposite beam. Similarly, the opposite beams of the beams 2 and 3 are irradiated from the gray point and the dark gray point respectively as also denoted by the dotted arrows. All the scanning beams irradiated from the black point are opposite to their respective opposite beams. This allows imaginary data of the opposite beams to be produced from data of the X-ray source from the white to dark gray points (as thus referred to as counter data). The opposite beam interpolation performs linear interpolation between the real data and its opposite data.

In the helical scanning, the sampling location for opposite data is varied depending on a beam (or a channel) as shown in FIG. 5D. For ease of the description, the sampling location is represented by the center channel denoted by the dotted line as shown in FIG. 5B. The interpolation of data sampled by the helical scanning may be implemented with the use of non-linear functions of which methods are also known.

(5)Slice Profile and Image Quality

Two of primary factors representing the performance of the system are slice profile and image quality. The slice profile is a impulse response along the Z-axis or (slice) direction. Its example is shown in FIG. 6 where an ideal slice has a square-like profile and its effective thickness (a width on a half of a value $I_O$) $W_{as}$ is small. More specifically, the profile 1 is identical in the effective slice thickness $W_{as}$ to the profile 2 but is more favorable in the shape than the same. The profile 2 is smaller in the effective slice thickness $W_{as}$ and thus more favorable than the profile 3.

As shown in FIG. 5A, the distance between two sampling locations of data to be used for the interpolation is termed an interpolation interval. The interpolation interval is equal to the helical pitch in the 360-degree interpolation and ½ the helical pitch in the opposite beam interpolation. The smaller the interpolation interval, the thinner the effective slice thickness $W_{as}$ is in the helical scanning action. Accordingly, the opposite beam interpolation is preferable.

(6)Multi-slice type CT scanning

For scanning a wider area at a higher resolution, a multi-slice type of CT scanning is provided having multiple rows, e.g. two, four, or eight rows, of detector elements as shown in FIGS. 7A, 7B, and 7C. FIG. 8A illustrates a fan beam viewed from the Z direction in which the center circle is an effective field of view (FOV). FIG. 8B explains four-row multi-slice CT scanning viewed from a direction vertical to the Z axis. The fundamental slice thickness T is defined by the width of a Z-axial beam at the center of rotation (spaced by a distance FCD from the X-ray source) which is irradiated from the X-ray source to a row of the detector elements.

(7)Helical Scanning of Multi-Slice Type CT Mode

The helical scanning of the multi-slice type CT mode is disclosed in Japanese Patent Laid-open Publication 4-224736 (1992). It is said that the helical pitch P of the multi-slice type CT scanning is substantially similar to the pitch of the single-slice type CT scanning and equal to a product of the number N of rows of the detector elements and the fundamental slice thickness T or a total slice thickness Ta at the center of rotation, as is expressed by:

$$P = N \times T \quad (1)$$

In this description, the helical pitch will be expressed hereinafter by a value calculated by dividing P by T. From the equation (1), the helical pitch is 4.

As depicted in the above publication, one of the interpolation methods for the helical scanning with the pitch of N in the N-row multi-slice type CT mode a modification of the 360-degree interpolation of the single-slice CT mode.

FIG. 9 is a scan diagram in which the four-row multi-slice type CT scanning employs such a modification of the interpolation. More particularly, similar to the 360-degree interpolation shown in FIG. 5A, the interpolation is carried out between two real data sampled at both sides of the target slicing location. This modification is now called an adjacent interpolation. Since the interpolation interval is equal to the fundamental slice thickness as alike in the 360-degree interpolation, the effective slice thickness $W_{as}$ is also similar to that of the 360-degree interpolation.

In the interpolation for the above (7) scanning, the effective slice thickness $W_{as}$ is not small. Hence, the opposite beams may be used for decreasing the effective slice thickness $W_{as}$.

FIG. 10A shows the helical scanning with an opposite beam at a pitch of 4, in which the opposite beam is denoted by the shaded area: a first rotation by the diagonal hatching and a second rotation by the vertical hatching. As apparent, most of the shaded area overlaps the sampling location of real data. Opposite data from scanning with the opposite beam is specified by the black rectangular area corresponding to the real data at the blank point in the single-slice type CT scanning. However, a majority of the opposite data is located on the same side of the target slicing location as of the real data. This requires extrapolation and if the opposite beam is desired without interruption, it may depart from the target slicing location depending on the channel or path. As the result, the extrapolation will increase generation of error and the departure from the target slicing location will cause the effective slice thickness $W_{as}$ to increase.

This drawback may be compensated by the opposite beams located opposite to the real data being sampled for opposite data as shown in FIG. 10B. Although no extrapolation is involved hence causing minimal error, there is generated an interruption between two adjacent beams in weighted interpolation. Consequently, the quality of a reconstructed image will be declined due to the interruption.

SUMMARY OF THE INVENTION

The present invention is developed in view of the foregoing aspects and its object is to provide an X-ray CT scanning apparatus for reconstructing a high quality image.

Another object of the present invention is to provide an X-ray CT scanning apparatus capable of processing image data at a higher speed.

For achievement of the above object, there is provided an X-ray CT scanning apparatus having an X-ray source for irradiating a beam of X-ray to an object to be examined, a detecting means provided with at least two rows of detector elements for detecting the X-ray beam to have a real data, and a couch traveling means for traveling in an axial direction of the body of the object a couch on which the object is placed, and characterized by irradiating the X-ray beam from the X-ray source which is being rotated and simultaneously, traveling the couch with the couch traveling means to scan the object in a helical direction so that the real data sampled by the detecting means is not identical in the sweep pattern to its opposite data.

Preferably, the scanning may be made so that the real data is not identical in the sweep pattern to its opposite data in a specific channel.

Also, the specific channel may be a significant channel essential for the purpose of examination.

For achievement of the above object, there is provided an X-ray CT scanning apparatus having an X-ray source for irradiating a beam of X-ray to an object to be examined, a detecting means provided with at least two rows of detector elements for detecting the X-ray beam to have a real data, and a couch traveling means for traveling in an axial direction of the body of the object a couch on which the object is placed, and characterized by: irradiating the X-ray beam from the X-ray source which is being rotated and simultaneously, traveling the couch with the couch traveling means to scan the object in a helical direction; and selecting two data located on both sides of the target slicing location from groups of the real data and their opposite data sampled by the detecting means and producing a desired data at the target slicing location by interpolation between the two selected data.

Preferably, the selection of the two data may independently be carried out in each channel.

Also, the scanning of the object in the helical direction may be conducted so that the real data is not identical in the sweep pattern to its opposite data.

For achievement of the above object, there is provided an X-ray CT scanning apparatus having an X-ray source for irradiating a beam of X-ray to an object to be examined, a detecting means provided with rows of detector elements for detecting the X-ray beam to have a real data, and a couch traveling means for traveling in an axial direction of the body of the object a couch on which the object is placed, and characterized by: irradiating the X-ray beam from the X-ray source which is being rotated and simultaneously, traveling the couch with the couch traveling means to scan the object in a helical direction; and filtering a group of the real data and their opposite data sampled by the detecting means to have a desired data at the target slicing location.

Preferably, the detecting means is provided with at least two rows of detector elements.

Preferably, the filtering may be a process of weighted addition.

Preferably, the filtering is carried out by a filter which is designed by reverse operation on the basis of a slice profile which is expected to be finally acquired.

Also, the filtering may comprise the steps of selecting a desired number of data from a group of the real data and their opposite data sampled by the detecting means, producing a corresponding number of data at imaginary slicing locations by interpolation between the selected data, and subjecting the data at the imaginary slicing locations to weighted addition.

The interpolation may be performed between two data which are located on both sides of each of the imaginary slicing locations and selected from the group of the real data and their opposite data sampled by the detecting means.

Furthermore, the filtering may comprise the steps of interpolating among a group of the real data and their opposite data sampled by the detecting means to produce imaginary conventional scanned real data, and producing a data at the target slicing location from the imaginary conventional scanned real data.

The interpolation may be performed between two data which are located on both sides of each of scanning locations for the imaginary conventional scanning and selected from the group of the real data and their opposite data sampled by the detecting means.

Also, the filtering may comprises the steps of interpolating among a group of the real data and their opposite data sampled by the detecting means to produce imaginary helical scanned real data of an imaginary single-slice CT mode, and producing a data at the target slicing location from the imaginary helical scanned real data and their opposite data.

The interpolation may be performed between two data which are located on both sides of each of scanning locations for the imaginary helical scanning and selected from the group of the real data and their opposite data sampled by the detecting means.

Preferably, the scanning of the object in the helical direction may be conducted so that the real data is not identical in the sweep pattern to its opposite data.

Also, the filtering may be implemented by a plurality of filter segments divided along the direction of slices from a filter for filtering a series of the data separately and combining them.

For achievement of the above object, there is provided an X-ray CT scanning apparatus having an X-ray source for irradiating a beam of X-ray to an object to be examined, a detecting means provided with at least two rows of detector elements for detecting the X-ray beam to have a real data, a couch traveling means for traveling in an axial direction of the body of the object a couch on which the object is placed, and an image reconstructing device for reconstructing a visual image from a group of the real data and their opposite data sampled by the detecting means, and characterized by: irradiating the X-ray beam from the X-ray source which is being rotated and simultaneously, traveling the couch with the couch traveling means to scan the object in a helical direction; and subjecting a group of the real data and their opposite data sampled by the detecting means to first image reconstruction for producing a series of preparatory voxel data and subjecting the preparatory voxel data to weighted addition along the direction of slices thus to produce the sliced image at the target slicing location.

The nature, principle and utility of the invention will become more apparent from the following detailed description when read in conjunction with the accompanying drawings.

BRIEF DESCRIPTION OF THE DRAWINGS

In the accompanying drawings:

FIG. 11 is a block diagram of an X-ray CT apparatus showing a first embodiment of the present invention;

FIG. 28 is a scan diagram of the four-row multi-slice CT scanning with P=4.5;

FIG. 29 is a scan diagram of the four-row multi-slice CT scanning with P=4.5 where the fundamental slice thickness is ½ of the value shown in FIG. 28;

FIGS. 40A to 40F are explanatory views showing a series of filtering actions for producing a desired slice profile;

FIG. 41 is an explanatory view showing the filter-like interpolation of opposite beams of the N1 channel in the four-row multi-slice CT scanning with P=4;

DESCRIPTION OF THE PREFERRED EMBODIMENTS

Figure 1A:
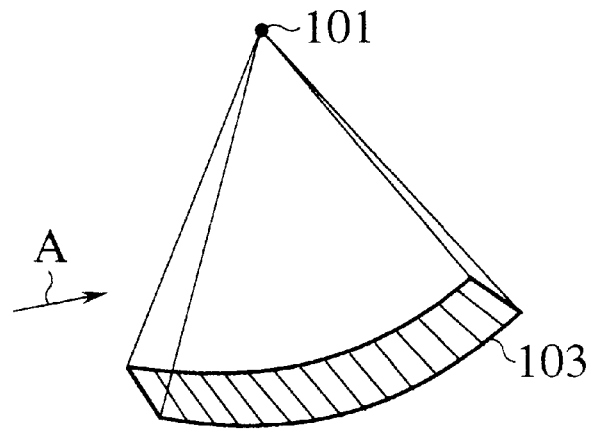
FIGS. 1A and 1B are diagrams showing a single-slice type CT scanning.
Figure 1B:
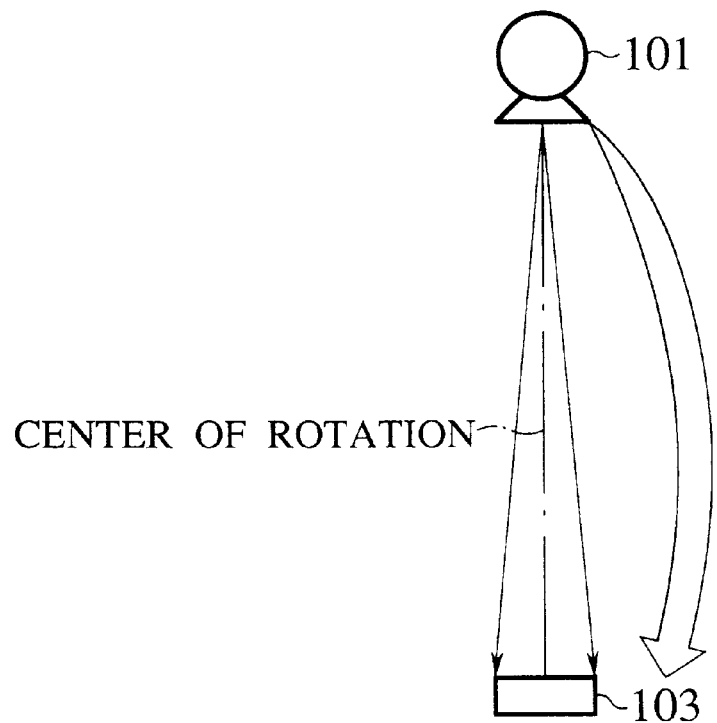
Figure 2A:
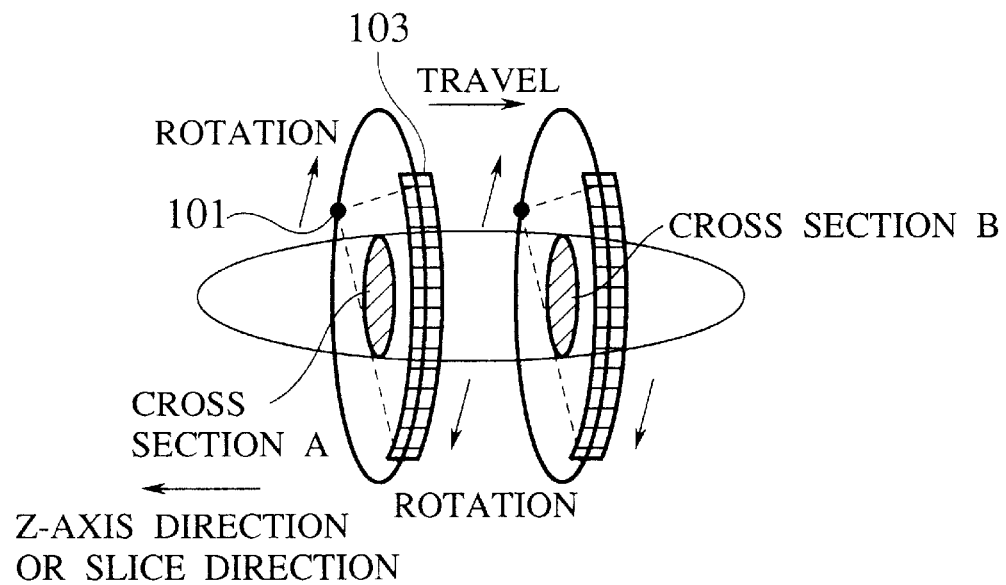
FIGS. 2A and 2B are diagrams explaining a conventional scanning action and a helical scanning action respectively.
Figure 2B:
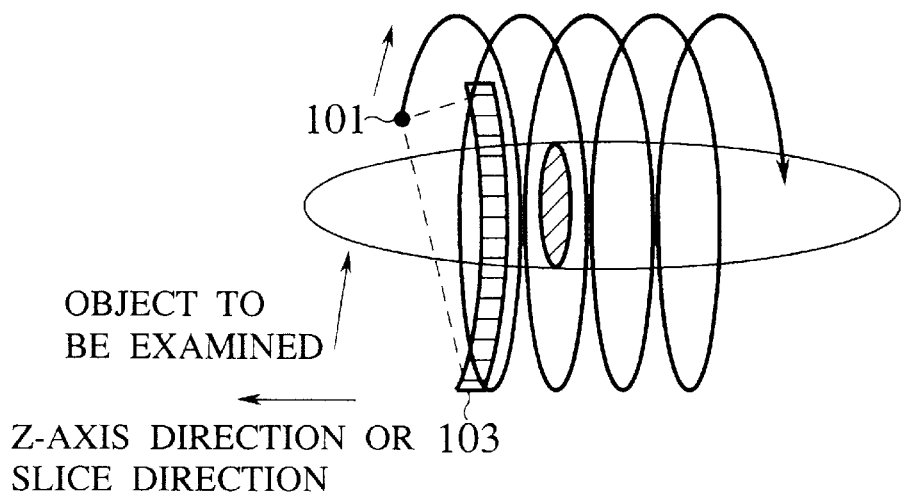
Figure 3:
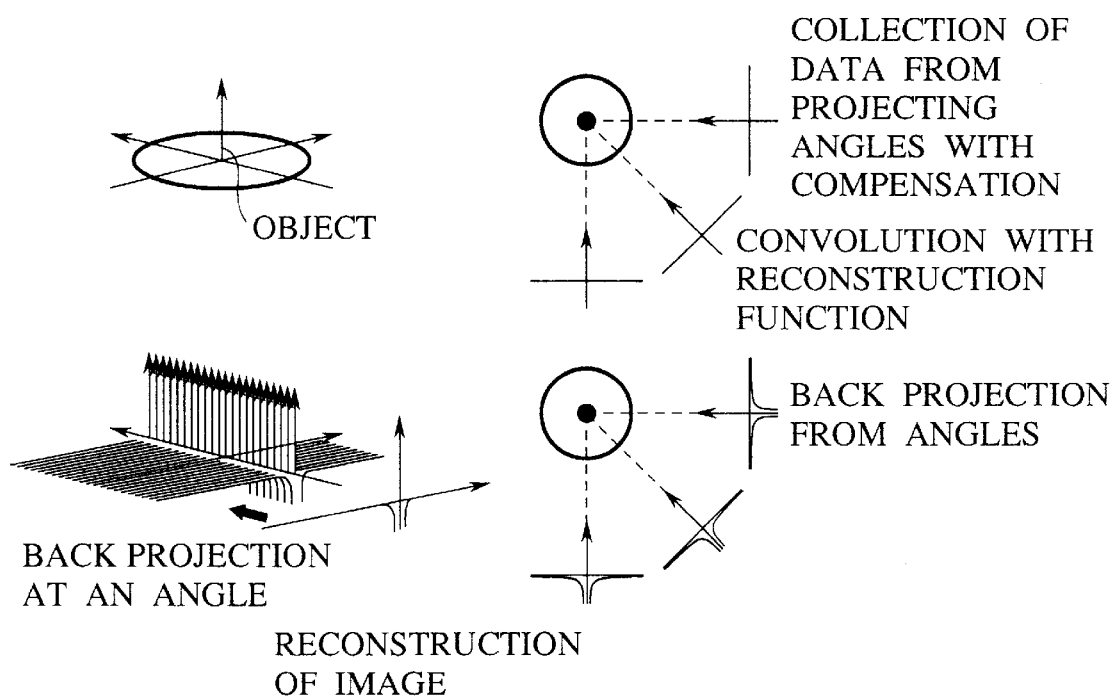
FIG. 3 illustrates the image reconstruction of an X-ray CT scan apparatus.
Figure 4A:
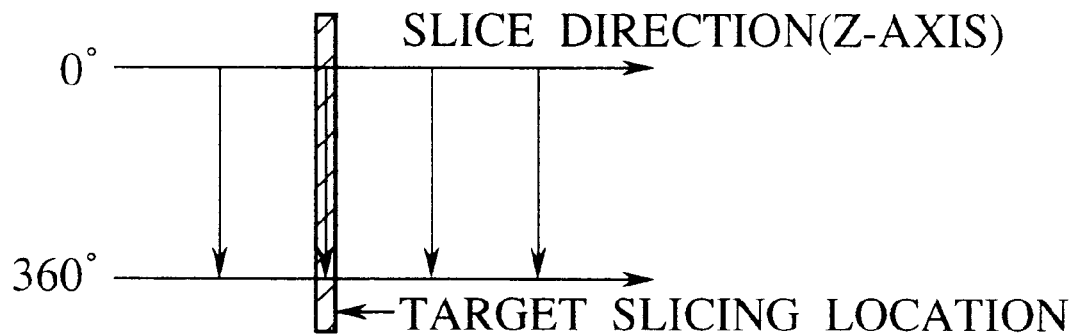
FIGS. 4A and 4B are scan diagrams of the conventional and helical scanning actions.
Figure 4B:
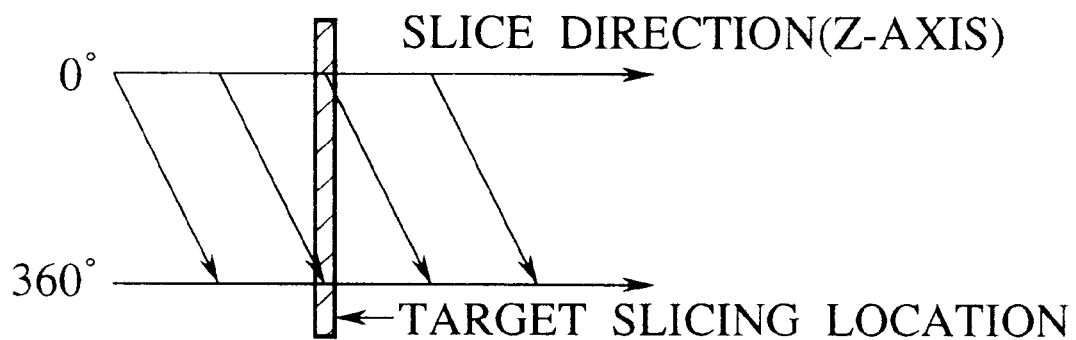

Preferred embodiments of the present invention will be described in detail referring to t he accompanying drawings. FIG. 11 is a block diagram of an X-ray CT scanning apparatus showing a first embodiment of the present invention.

The X-ray CT apparatus 10 according to the first embodiment is designed for interpolating X-ray beams (of detected data) by adjacent interpolation at the target slicing location and also at, at least, two different slicing locations spaced from and located on both sides of the target slicing location, and subjecting the interpolated X-ray beams to weighted addition thus to produce a desired slice data of X-ray beam.

The X-ray CT apparatus 10 of the first embodiment comprises, as shown in FIG. 11, a system controller 11, a gantry/couch controller 13, a couch driver 15, an X-ray controller 17, a high-voltage generator 19, an X-ray beam source 21, a detector 23, a gantry 25, a data acquisition system (DAS) 27, an Interpolator 29, an image reconstructor 31, and a display 33.

The system controller 11 receives requirements of the helical scanning action from an entry device not shown and transmits the rotating speed, the slicing thickness, and the fan beam angle of the requirements as gantry/couch control signals to the gantry/couch controller 13. Also, the system controller 11 delivers an X-ray beam generation control signal to the X-ray controller 17. A detection control signal for timing the detection of X-ray is fed from the system controller 11 to the DAS 27. The system controller 11 also feeds the DAS 27 with a data collection control signal for collection of data. An interpolation control signal is transmitted from the system controller 11 to the interpolator 29 for carrying out a desired type of interpolation.

The gantry/couch controller 13 upon receiving the gantry/couch control signals from the system controller 11 drives a rotating movement of the gantry 25 and simultaneously, delivers a couch drive signal to the couch driver 15.

The couch driver 15 receives the couch drive signal from the gantry/couch controller 13 and calculates a traveling distance of a couch 15a per one rotation of the gantry 25 to move the couch 15a through the traveling distance.

The X-ray controller 17 is response to the X-ray beam generation control signal from the system controller 11 for controlling the timing of high voltage generation of the high-voltage generator 19.

The high-voltage generator 19 upon receiving the control signal from the X-ray controller 17 generates and feeds a high voltage to the X-ray beam source 21 for irradiation of an X-ray beam.

The X-ray beam source 21 is driven by the high voltage from the high-voltage generator 19 for irradiating an X-ray beam.

The X-ray beam irradiated from the X-ray source 21 is passed through an object to be examined and received by the detector 23.

The gantry 25 carries thereon the X-ray beam source 21 and the detector 23 and is driven by a gantry driving mechanism, not shown, for rotation about the axis of rotation which extends across an intermediate point between the X-ray beam source 21 and the detector 23.

The DAS 27 is responsive to the data collection control signal from the system controller 11 for sampling data of the X-ray beams (actually, detection signals) received by the detector 23.

The interpolator 29 receives the X-ray beam data from the DAS 27 and interpolates an X-ray beam at the target slicing location. The interpolator 29 comprises commonly a CPU and memories.

The image reconstructor 31 is responsive to an interpolated X-ray beam from the interpolator 29 for reconstructing a visual image.

The display 33 allows display of the reconstructed image on a monitor not shown.

The action of the X-ray CT apparatus 10 of the first embodiment will now be explained. The requirements for a desired helical scanning action are entered by an operator through an entry device not shown. It is assumed that the helical scanning requirements are: Number of rows of the detector elements: $N_{seg}=2$ Number of channels of the detector elements: $N_{ch}=1000$ Width of row at the center of rotation along Z axis:=fundamental slice thickness: $D_{seg}=20$(mm)

Thickness of beam at the center of rotation: $N_{seg} \times D_{seg}=40$ (mm)

Distance between source and center of rotation: FCD=600 (mm)

Distance between source and detectors: FDD=1200(mm)

Diameter of field of view: FOV=500(mm)

Angle of field of view (fan angle): $\phi=50$ degrees

Upon receiving the above helical scanning requirements, the system controller 11 delivers the gantry/couch control signals of rotating speed, slice thickness, and fan angle to the gantry/couch controller 13 which in turn transmits the couch drive signal to the couch driver 15.

Then, when a diagnosis start command is entered through the entry device by the operator, the system controller 11 directs the gantry/couch controller 13 to start its action and feeds the X-ray controller 17 with the X-ray beam generation control signal for starting the generation of X-ray beam. Upon receiving the X-ray beam generation control signal, the X-ray controller 17 drives the high-voltage generator 19 to generate a high voltage.

This allows the X-ray source 21 to irradiate an X-ray beam and the couch driver 15 to move the couch 15a to a desired location for starting an action of the helical scanning.

In response to the data collect control signal from the system controller 11, the DAS 27 reads data of the X-ray beam from the detector 23 and transmits the detected data to the interpolator 29.

The interpolator 29 upon receiving the X-ray beam data performs an action of interpolation to produce an X-ray beam data at the target slicing location. An example of the interpolation of data performed by the interpolator 29 is shown at the left in FIG. 12. Shown at the right in FIG. 12 is the relation between a target phase point and a weighting of data in the data interpolation from 0 to 360 degree of the phase.

Figure 12:
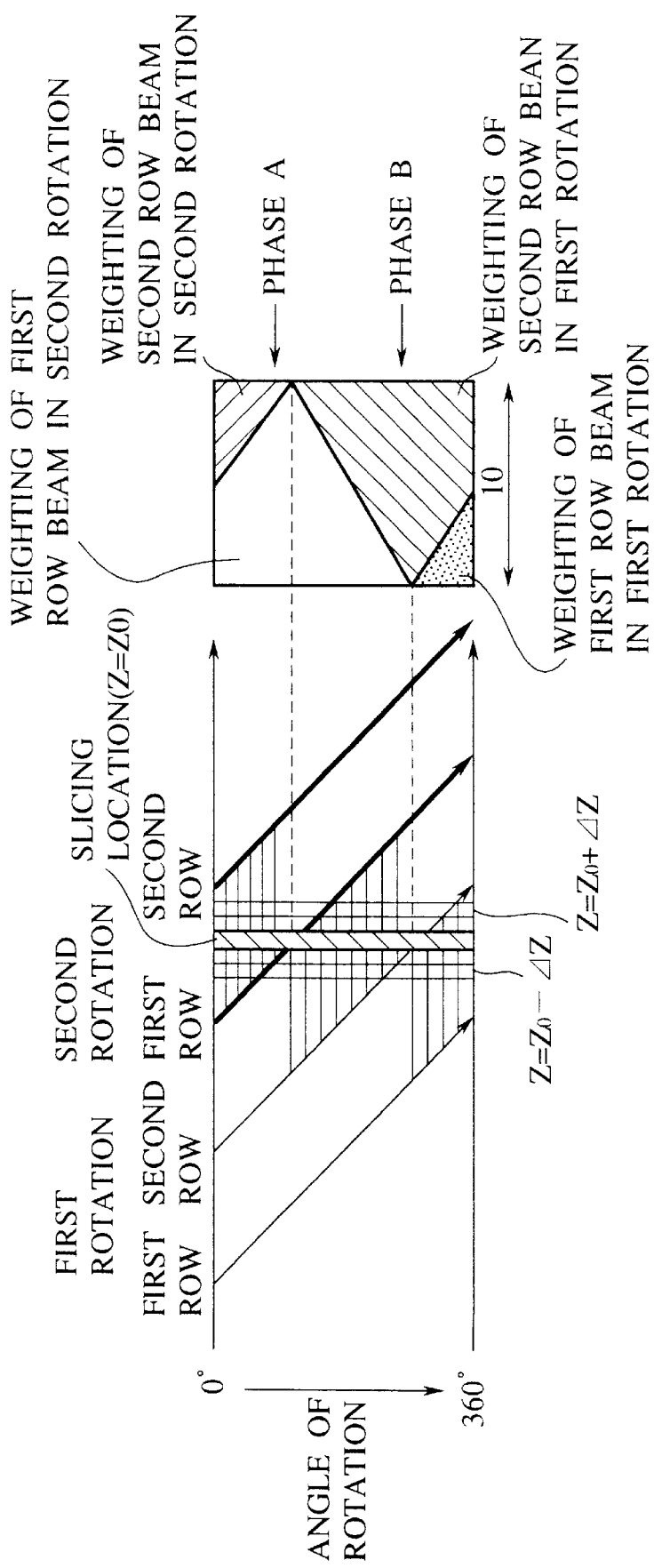
FIG. 12 is an explanatory view showing a data interpolation on the X-ray CT apparatus of the first embodiment shown in FIG. 11.

As shown at the left in FIG. 12, the interpolation starts between the first and second row beams in the second rotation at the upper end (at the phase of 0). As the interpolation proceeds (from 0 to 360 degree), a weighting of the first row beam in the second rotation is increased and a weighting of the second row beam in the second rotation is decreased. At the phase point A, the weighting of the first row beam in the second rotation only is left. Then, as the weighting of the first row beam in the second rotation is decreased, the weighting of the second row beam in the first rotation is increased. At the phase point B, the weighting of the second row beam in the first rotation is left. This is followed by decreasing the weighting of the second row beam in the first rotation and increasing the weighting of the first row beam in the first rotation.

Figure 13:
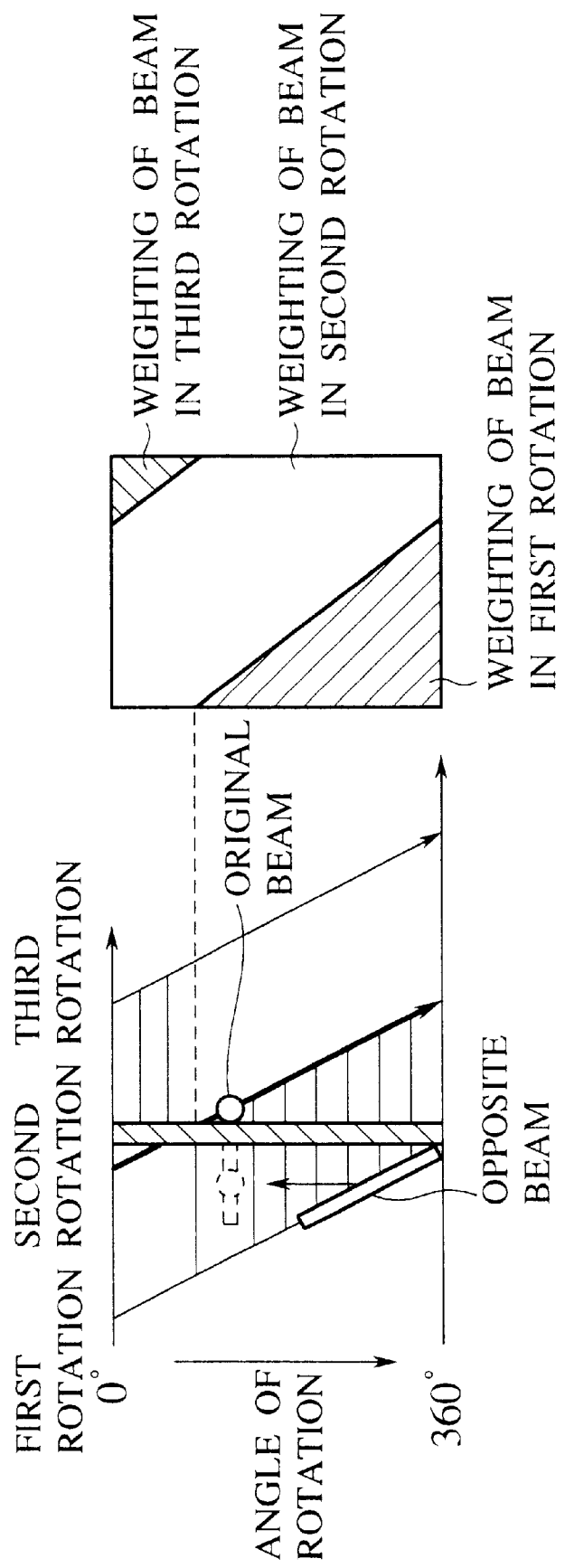
FIG. 13 is an explanatory view showing a data interpolation in a single-slice CT mode.

FIG. 13 illustrates at the left an example of the data interpolation in the single-slice type CT scanning. Shown at the right in FIG. 13 is a pattern of weighting in the single-slice type CT scanning. As apparent, there are three types of difference between the single-slice mode and the multi-slice mode CT scanning. Firstly, the multi-slice mode allows N times of beam switching for the interpolation as shown at the right in FIG. 12 and the phase points at the switching are opposite to each other, for example, $\theta$ and $\theta+180°$. Secondly, the variation of the weighting (a difference of weighting between two adjacent views) is higher in the multi-slice mode. Thirdly, change of the data characteristics at the switching is greater due to discrete outputs of the detector elements than in the single-slice mode. As suffering from the three differences, the multi-slice type CT scanning permits the interpolation to cause a considerable degree of declination in the quality of a reconstructed image.

The effect of the switching of beams to be used for the interpolation is proportional to its duration (a gap). The effect of the switching is preferably minimum and should be attenuated by a specific manner. In the X-ray CT apparatus 10 of the first embodiment, the effect of the switching is prevented from stressing in both the phase points A and B.

Figure 14A:
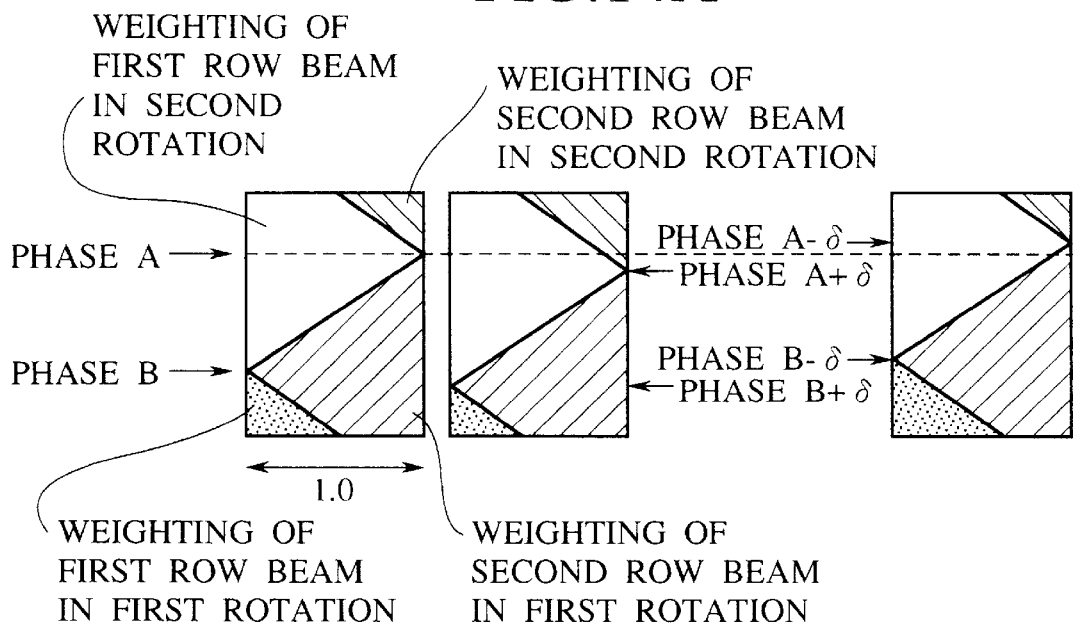
FIGS. 14A to 14C are diagrams showing weightings of interpolation at the target slicing location, at a slicing location dislocated by $\pm\alpha Z$ from the target slicing location, and a sum of the two weightings respectively.

For example, a weighting for the interpolation at a slicing location $Z=Z0+\Delta \times Z$ shown in FIG. 12 is interpreted to at the center in FIG. 14A. Shown at the right in FIG. 14A is a weighting at a slicing location $Z=Z0-\Delta \times Z$. As apparent from FIG. 14A, the phase point where the switching is involved is slightly shifted from A to A±δ and from B to B±δ with a forward or backward displacement of the slicing location.

It is now assumed that the interpolated DATA(h, Z0+i×Δ) where i=−n,n of 2n+1 slices at the slicing locations from $Z=Z0-n\times\Delta$ to $Z=Z0+n\times\Delta$ spaced by Δ is acquired, and then the DATA(h, Z0+i×Δ) is weighted by a weighting of W(i) as expressed by the equation (2) to acquire the DATA(θ, Z0) at the target phase point:

$$\text{DATA}(\theta, Z_0) = \Sigma W(i) \, \text{DATA}(\theta, Z0+i\times\Delta) \qquad \ldots (2)$$

where i varies from −n to n.

As the interpolated data at the displaced slicing location is subjected to weighted addition, the slice thickness $W_{as}$ is increased. However, the change of the weighting for the interpolation appears moderate as shown in FIG. 14B.

Figure 14B:
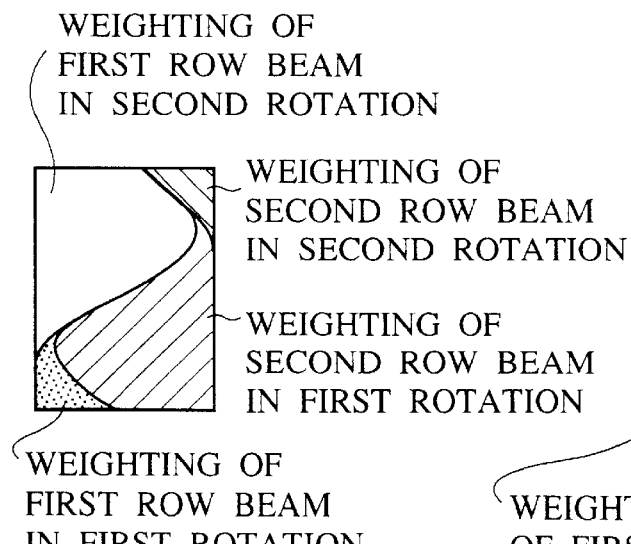
Figure 14C:
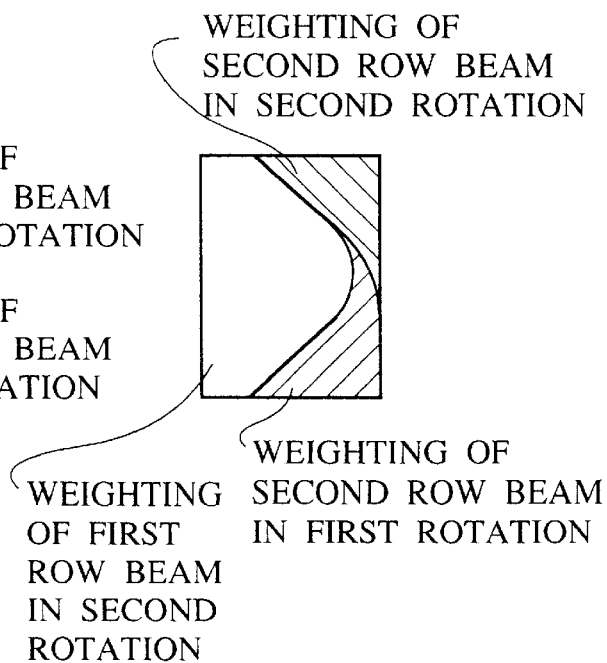

FIG. 14C shows an enlarged view of the change of the weighting (at the phase A of FIG. 14B). As apparent, the change of the weighting for the interpolation (above the phase A of FIG. 14B) involves increase of the weighting of the first-row beam in the second rotation. Simultaneously, while the weighting of the second-row beam in the second rotation is decreased, the weighting of the second-row beam in the first rotation increases. This is followed by decreasing the weighting of the first-row beam in the second rotation, eliminating the weighting of the second-row beam in the second rotation, and increasing the weighting of the second-row beam in the first rotation. As the result, the change of the weighting will be moderate thus attenuating the effect of the switching between beams for the interpolation and improving the quality of a reconstructed image.

Figure 15:
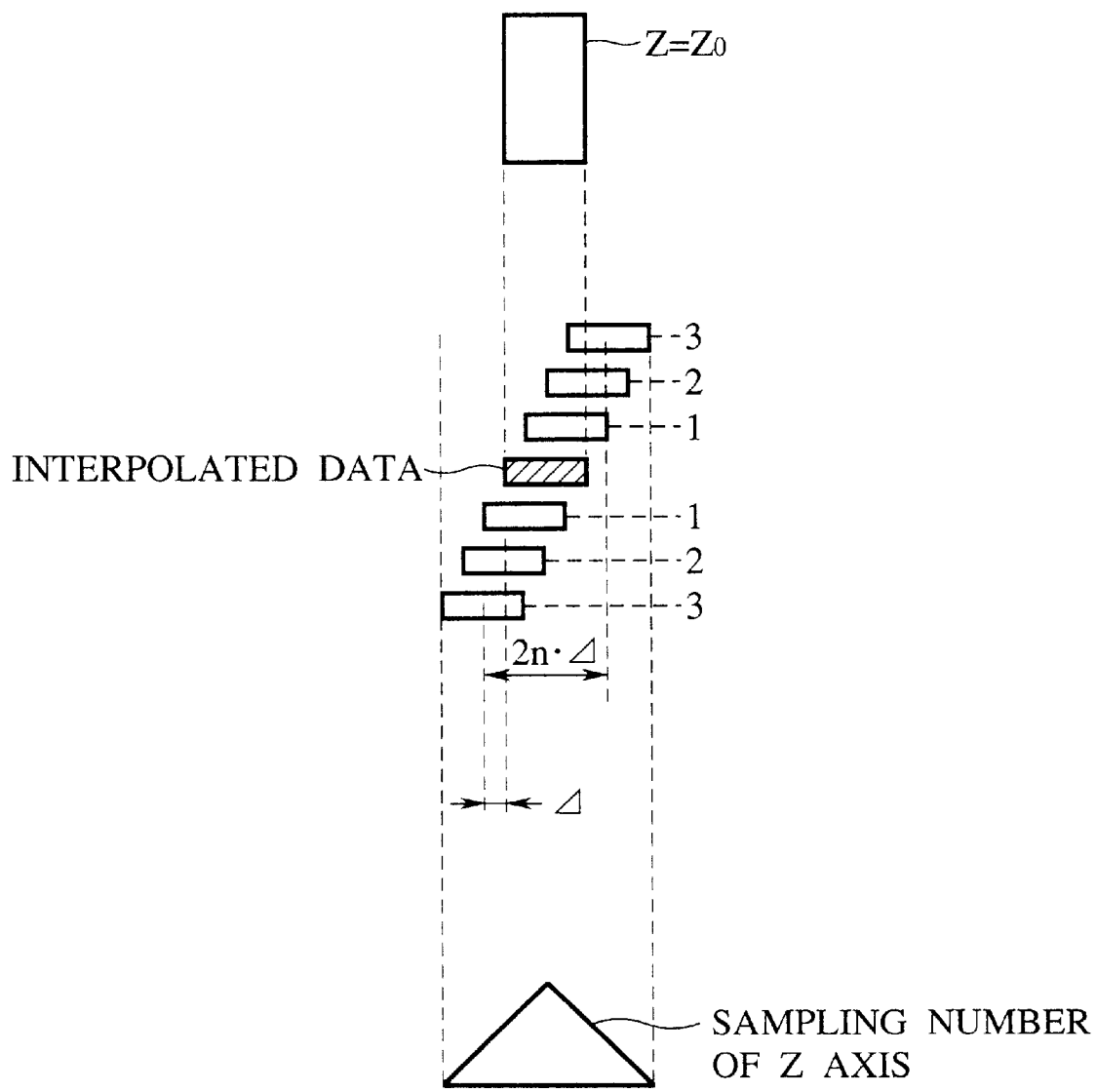
FIG. 15 is an explanatory view showing addition of n data about the data of the target slicing location Z=Z0.

At the time, data of 2n+1 slices is added about the target slicing location Z=Z0, as shown in FIG. 15. This is equivalent to a filtering process shown at the lower in FIG. 15 in respect to the action of counting (or sampling) the Z-axial locations. Also, the interpolation is made between more than one pair of beam data as compared with two beams for one phase point in the prior art. The number of beams is determined depending on the interval between the interpolating beams and the relation between the current phase point and the switched phase point. The process of the interpolation is then referred to as filter-like interpolation. The weighting may be of any type while FIG. 15 illustrates a uniform addition mean method.

As clearly understood from its principle, the filter-like interpolation is more effective with a higher rate of the sampling density. This embodiment permits the interpolation with weighted addition of 2n+1 slices as for ease of the description. In practice, the interpolation may be carried out with the use of a filter which is highly functionable along the slice direction.

Figure 16:
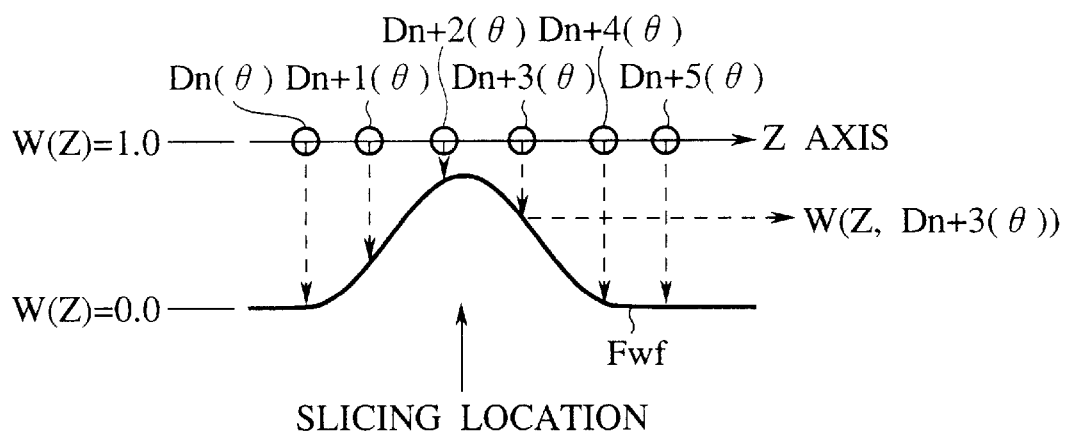
FIG. 16 is a diagram showing a data sampled at a fixed point $\theta$ of the phase with a weighted filtering function.

For example, if the data collected at the fixed phase θ are $D_n(\theta)$, $D_{n+1}(\theta)$, and so on, a plurality of sampling points are aligned in the slice direction as shown in FIG. 16. Through filtering in the slice direction, weighted coefficients are determined for producing the interpolated data at the target slicing location.

The weighted coefficient for each data is calculated from a filtering function $F_{wf}$ shown in FIG. 16. For example, the weighting of the (n+3)th data $D_{n+3}(\theta)$ at the phase θ is expressed by $W(Z, D_{n+3}(\theta))$ in consideration of the relation between the target slicing location, the weighted filtering function, and the Z axis value of $D_{n+3}(\theta)$. For normalization, the weighting is divided by the weightings of all the data as shown in the equation (3):

$$\text{Weighting } (Z, D_{n+3}(\theta)) = W(Z, D_{n+3}(\theta))/\Sigma W(Z, D_k(\theta)) \qquad (3)$$

The weighting of each data is then used for calculating the interpolated data from:

$$\text{DATA}(\theta) = \Sigma[\text{Weight}(Z, D_k) \times D_k(\theta)] \qquad (4)$$

The interpolated X-ray beam data (detected data) from the interpolator 29 is supplied to the image reconstructor 31 where an image is reconstructed, and then image data is transferred and displayed on the monitor of the display 33.

As described, the X-ray CT apparatus 10 of the first embodiment produces an X-ray beam data of a desired slice by carrying out adjacent interpolation to produce an X-ray beam at the target slicing location and X-ray beams at at least two slicing locations, and subjecting the interpolated X-ray beams to weighted addition, whereby declination of the quality of a reconstructed image caused by switching between the interpolating beams will be minimized.

A second embodiment of the X-ray CT apparatus will now be described. The X-ray CT apparatus of the second embodiment is characterized by positive interpolation of opposite beams as compared with the conventional opposite beam interpolation method in which the original beam and its opposite beam sampled at the closest point to the target slicing location are used for either interpolation (where the target slicing location is inside the interpolating beams) or extrapolation.

The interpolation is carried out with a couple of beams which are sampled at the two closest locations to and on both sides of the target slicing location as selected out of from 16 different beams, i.e. 2 rows×4 rotations×2 (an original beam and its opposite beam), which have been delivered at the phase point θ from two rows of the detector elements of the detector 23 during four rotations. In this interpolation, opposite beams are actively interpolated. Hence, the interpolation of this embodiment is referred to a new opposite beam interpolation.

The X-ray CT apparatus of the second embodiment is substantially identical in the construction to the X-ray CT apparatus 10 of the first embodiment shown in FIG. 11. Accordingly, like components are denoted by like numerals and will be explained in no more detail.

The action of the X-ray CT apparatus of the second embodiment is explained in which the action of the components other than an interpolator 29 is identical to that of the first embodiment and will not be referred.

Figure 17:
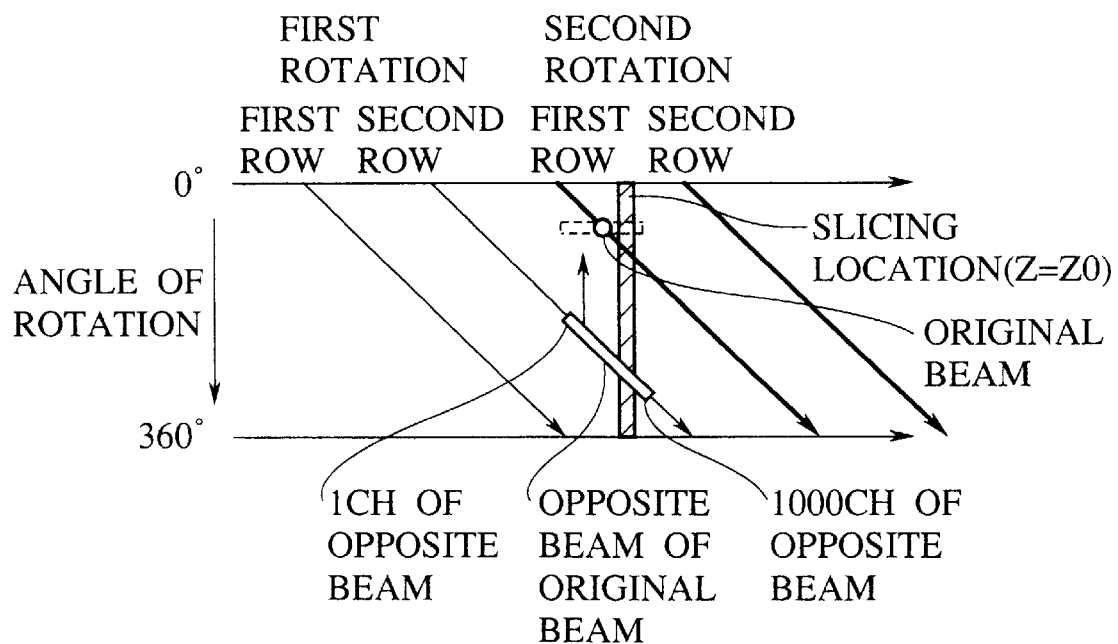
FIG. 17 is an explanatory view showing the original beam and its opposite beam with a detector having the number of rows of $N_{seg}=2$ and the number of channels of $N_{ch}=1000$.
Figure 18A:
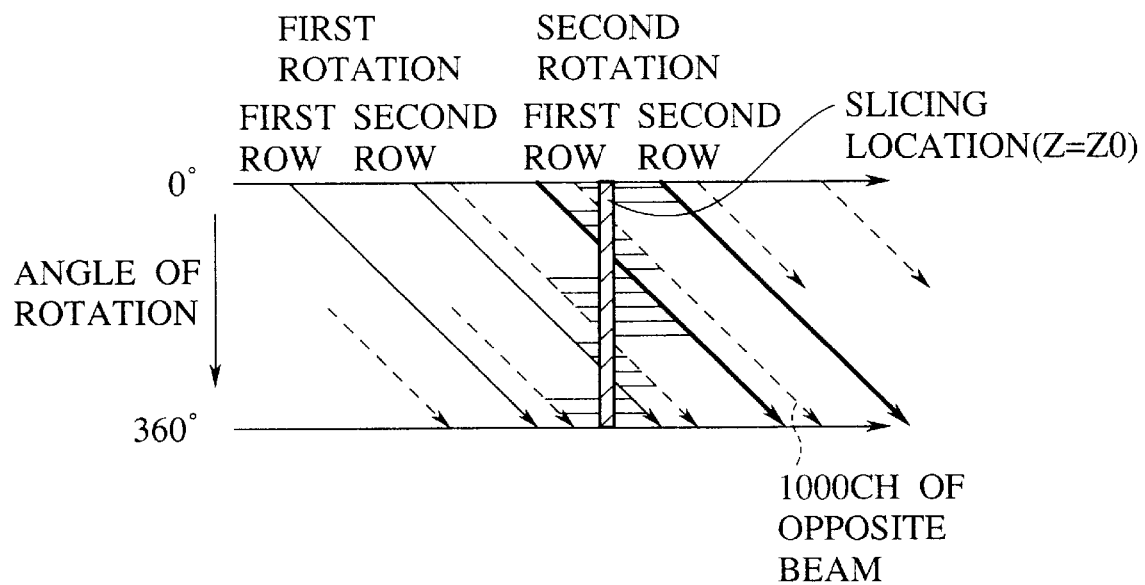
FIGS. 18A and 18B are explanatory views showing a new opposite beam interpolation on an X-ray CT apparatus of a second embodiment.
Figure 18B:
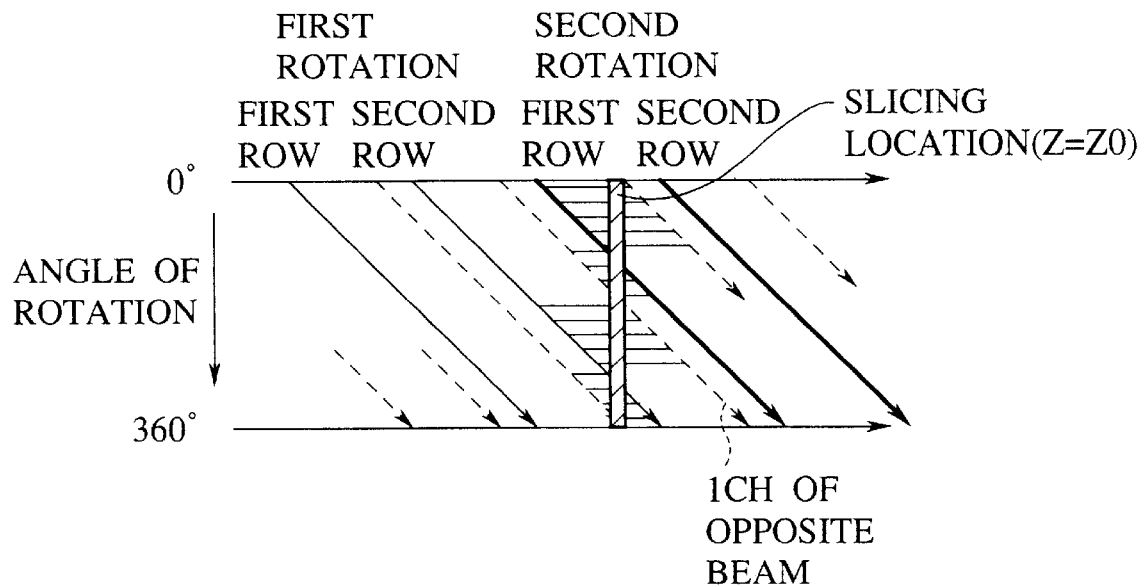

When the detector 23 is identical to that of the first embodiment (including the detector elements of $N_{seg}=2$ by $N_{ch}=1000$), opposite beams at all applicable phase points are defined by the rectangular shaped real line in FIG. 17 from channel 1 to channel 1000. The opposite beams appear at different slicing locations depending on the number of channels. It is now examined at the channel 1000 where the opposite beams appear as are denoted by the dotted line in FIG. 18A. Two beams located most adjacent to and on both sides of the target slicing location are selected from eight beams which include four original beams, 2 rotations by 2 rows, denoted by the real lines and four opposite beams, 2 rotations by 2 rows. The linear or non-linear interpolation between the two selected beams with an inverse of the ratio of distance between the beam location and the target slicing location hence produces data of the channel 1000 at the phase point. Similarly, the channel 1 is interpolated as shown in FIG. 18B. By repeating this procedure, all data through 360 degrees of the phase can be obtained.

As described, the X-ray CT apparatus of the second embodiment employs the new opposite beam interpolation for interpolation of data where the phase point involving the switching between interpolating beams is not uniform but different depending on the channel. Accordingly, the switching in each view will be minimized (or decreased in number in spite of the length of a helical pitch) thus improving the quality of a reconstructed image. Also, the interval between interpolating beams is decreased in average and so the effective slice thickness $W_{as}$ as compared with that of the adjacent interpolation shown in FIG. 12.

A third embodiment of the X-ray CT apparatus will be described which is implemented by a combination of the filter-like interpolation of the first embodiment and the new opposite beam interpolation of the second embodiment.

The X-ray CT apparatus of the third embodiment is substantially identical in the construction to the X-ray CT apparatus 10 of the first embodiment. Like components are denoted by like numerals and will be explained in no more detail.

The action of the X-ray CT apparatus of the third embodiment is explained in which the action of the components other than an interpolator 29 is identical to that of the first embodiment and will not be referred.

The interpolator 29 in the third embodiment produces, for example, DATA(Z0) of a desired phase point θ at the slicing location Z=Z0 shown in FIG. 12, and DATA(Z0+i×Δ) (i=−n, n) of the phase point θ at the location Z=Z0+i×Δ, using the new opposite beam interpolation. From the DATA(Z0) and DATA(Z0+i×Δ), target DATA(θ, Z0) is calculated using the weighted addition (2) of the filter-like interpolation. By repeating this procedure, all data through 360 degrees of the phase can be obtained.

As described, the X-ray CT apparatus of the third embodiment employs a combination of the filter-like interpolation and the new opposite beam interpolation for interpolation of desired data. Accordingly, declination in the quality of a reconstructed image caused by switching between interpolating beams will be minimized. Also, the interval between the interpolating beams is decreased in average and so the effective slice thickness $W_{as}$.

A fourth embodiment of the X-ray CT apparatus will now be described in which a combination of the filter-like interpolation of the first embodiment and the new opposite beam interpolation is used. In particular, the opposite beams are dislocated to have the helical pitch not aligned with the beam thickness so that error of the interpolation in the multi-slice type scanning remains small or the slicing location of the original beam is spaced away from that of the opposite beam.

The X-ray CT apparatus of the fourth embodiment is substantially identical in the construction to the X-ray CT apparatus 10 of the first embodiment shown in FIG. 11. Like components are denoted by like numerals and will be explained in no more detail.

The process of the X-ray CT apparatus of the fourth embodiment is explained referring to the relevant drawings.

In the X-ray CT apparatus of the fourth embodiment, the helical pitch P is defined smaller than the pitch shown in the equation (1) as expressed by:

$$(N/2-0.5)\times T<P<NT \quad (5)$$

Figure 19:
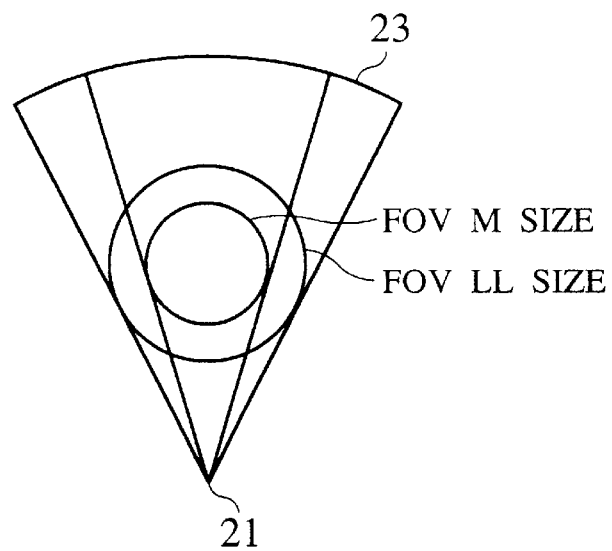
FIG. 19 is a view showing sizes of FOV.

Then, to prevent the location of the opposite beam from overlapping the location of the original beam, the helical pitch is determined from:

$$P<NT\times 180/(180+\alpha),\ NT\times 180/180-\alpha)<P \quad (6)$$

where α is greater than the angle of a fan beam irradiated from an X-ray source 21 (for example, α=55 when the fan angle is 50) for allowing the two beams to be spaced from each other when FOV (shown LL and MM in FIG. 19) is maximum (LL in FIG. 19).

The helical scanning in the X-ray CT apparatus of the fourth embodiment is carried out with the optimum helical pitch P defined above.

Figure 20:
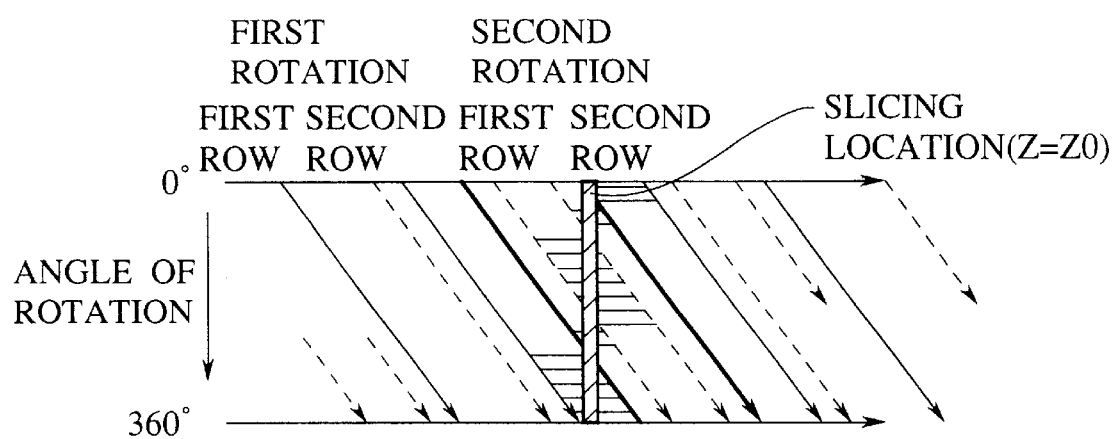
FIG. 20 is an explanatory view showing a combination of the filter-like interpolation and the new opposite beam interpolation on an X-ray CT apparatus of a fourth embodiment using two rows of detector elements.

The interpolator 29 produces DATA(Z0) of a desired phase point θ at the slicing location Z=Z0 shown in FIG. 20 using the new opposite beam interpolation. Referring to FIG. 20, the original beam is denoted by the real line and its opposite beam is denoted by the dotted line. Then, DATA(Z0+i·Δ)(i=−n, n) of the phase point θ at Z=Z0+i·Δ is calculated by the new opposite beam interpolation. From the DATA(Z0) and DATA(Z0+i·Δ), target DATA(h, Z0) is calculated using the weighted addition (2) of the filter-like interpolation. By repeating this procedure, all data through 360 degrees of the phase can be obtained.

If the number N of the detector rows is 2, the fan angle is 50 (at LL), and α is 55, the helical pitch P is expressed by P<3.06 or P>5.76. FIG. 20 is a scan diagram in which P is 3(mm) while the interpolation between the opposite beams is actively involved.

Figure 21A:
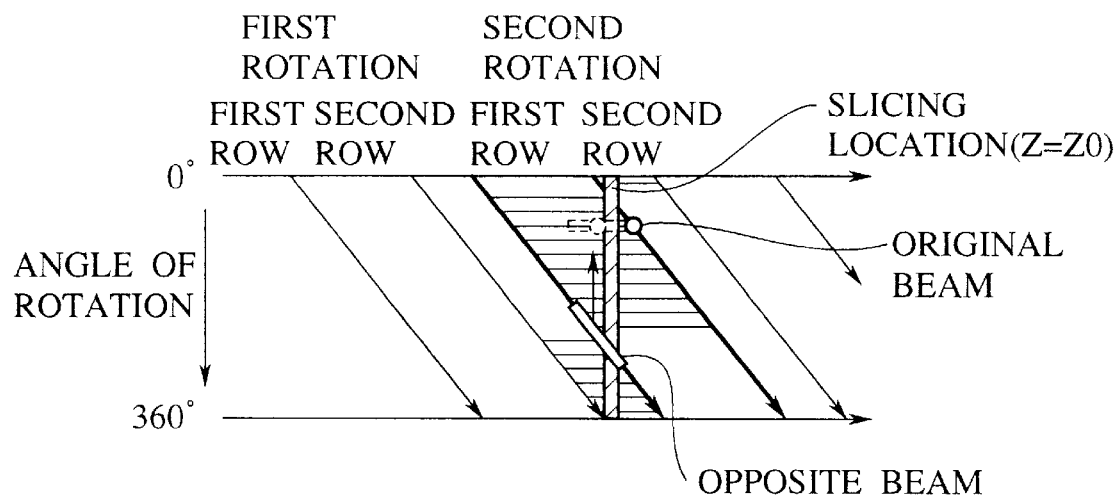
FIGS. 21A to 21C are explanatory views showing adjacent interpolation, 360-degree interpolation, and opposite beam interpolation respectively.

From comparison between the interpolation shown in FIG. 20 and the adjacent interpolation shown in FIG. 21A, it is apparent that the interval between interpolating beams is smaller and so the effective slice thickness $W_{as}$ in FIG. 20. For example, the original beam at the phase point denoted by the real line circle in FIG. 21A is adjacent interpolated between the two-row beam of the second rotation and the first-row beam of the second rotation. In FIG. 20, the data at the target slicing location is however interpolated between the original beam at the real line circle and its opposite beam at the dotted line circle which are narrowly spaced from each other.

Figure 21B:
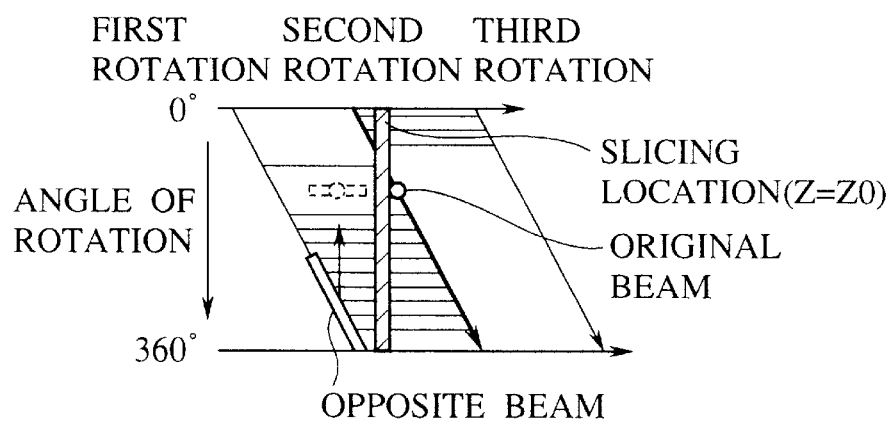
Figure 21C:
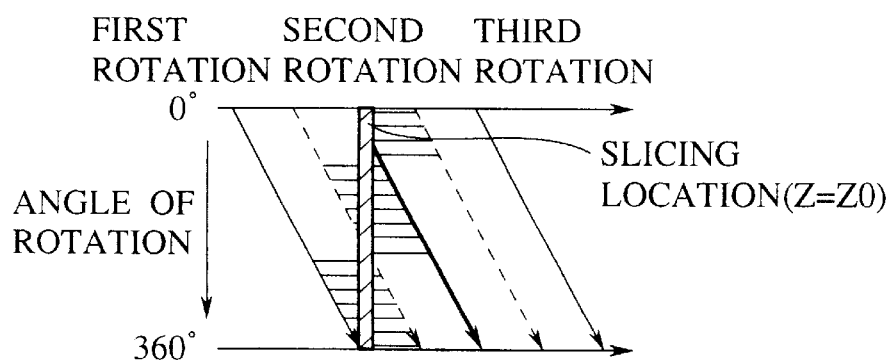

As compared with the 360-degree interpolation for single-slice type scanning shown in FIG. 21B and the opposite beam interpolation for single-slice type scanning in FIG. 21C, the interpolation shown in FIG. 20 has the interval between interpolating beams equal to or smaller than that of the opposite beam interpolation depending on a degree of the phase. For example, the target slicing location of a phase point denoted at the real line circle in FIG. 21B is 360-degree interpolated between the original beams of the second and first rotations. The interpolation at the target slicing location in FIG. 20 is carried out between the original beam denoted by the real line circle and its opposite beam denoted by the dotted line circle, allowing the interpolation interval to be smaller.

Accordingly, the filter-like interpolation and the new opposite beam interpolation in a combination can decrease the effective slice thickness.

If the number N of the detector rows is 4, the helical pitch P is P<6.12 or P>11.52 according to the equation (6). FIGS.

22, 23, and 24 show scan diagrams in which P=5(mm), P=6(mm), and P=7(mm) respectively are given. As P=5 (mm) in FIG. 22 is smaller than P=7(mm) in FIG. 25, the former is higher in the quality of a reconstructed image but longer in the scanning duration and greater in the dose of X-ray than the latter.

Figure 22:
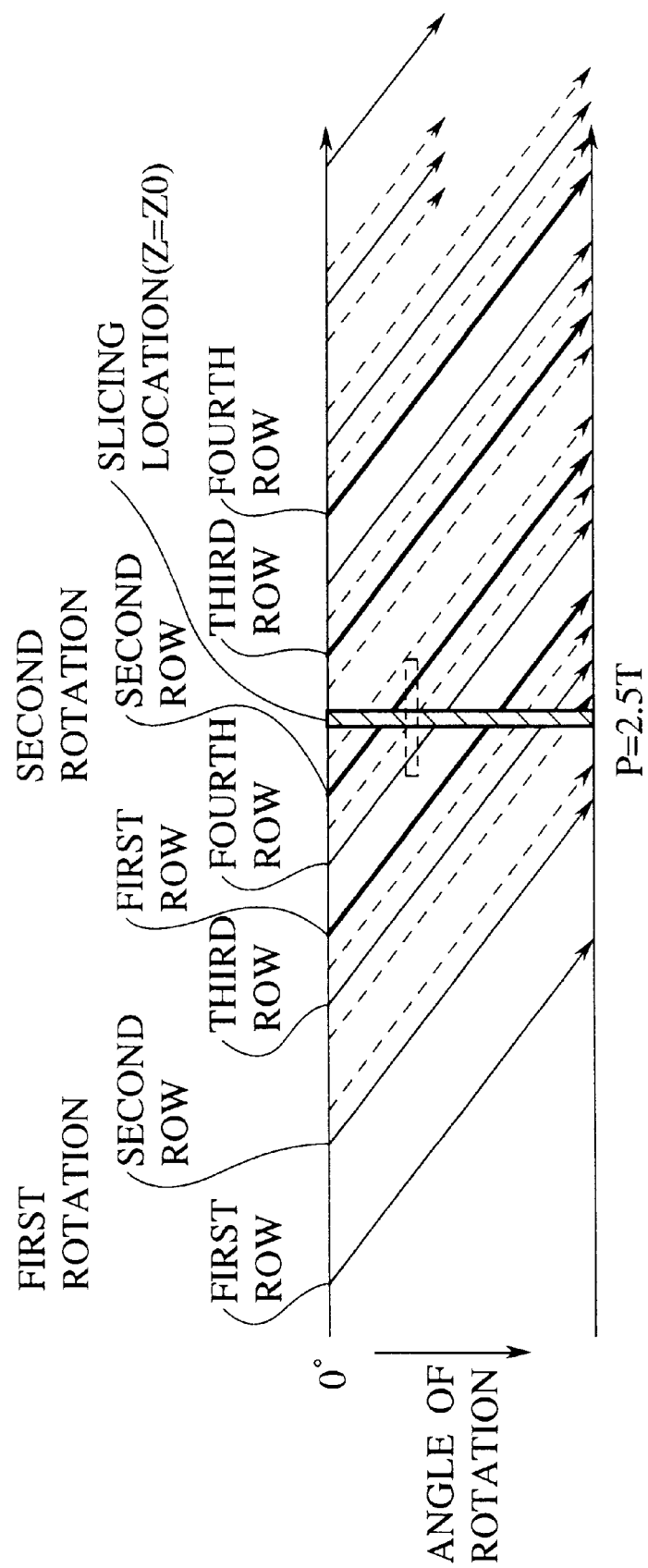
FIG. 22 is an explanatory view showing a combination of the filter-like interpolation with a helical pitch P=2.5T and the opposite beam interpolation on an X-ray CT apparatus of the fourth embodiment using four rows of detector elements.
Figure 23:
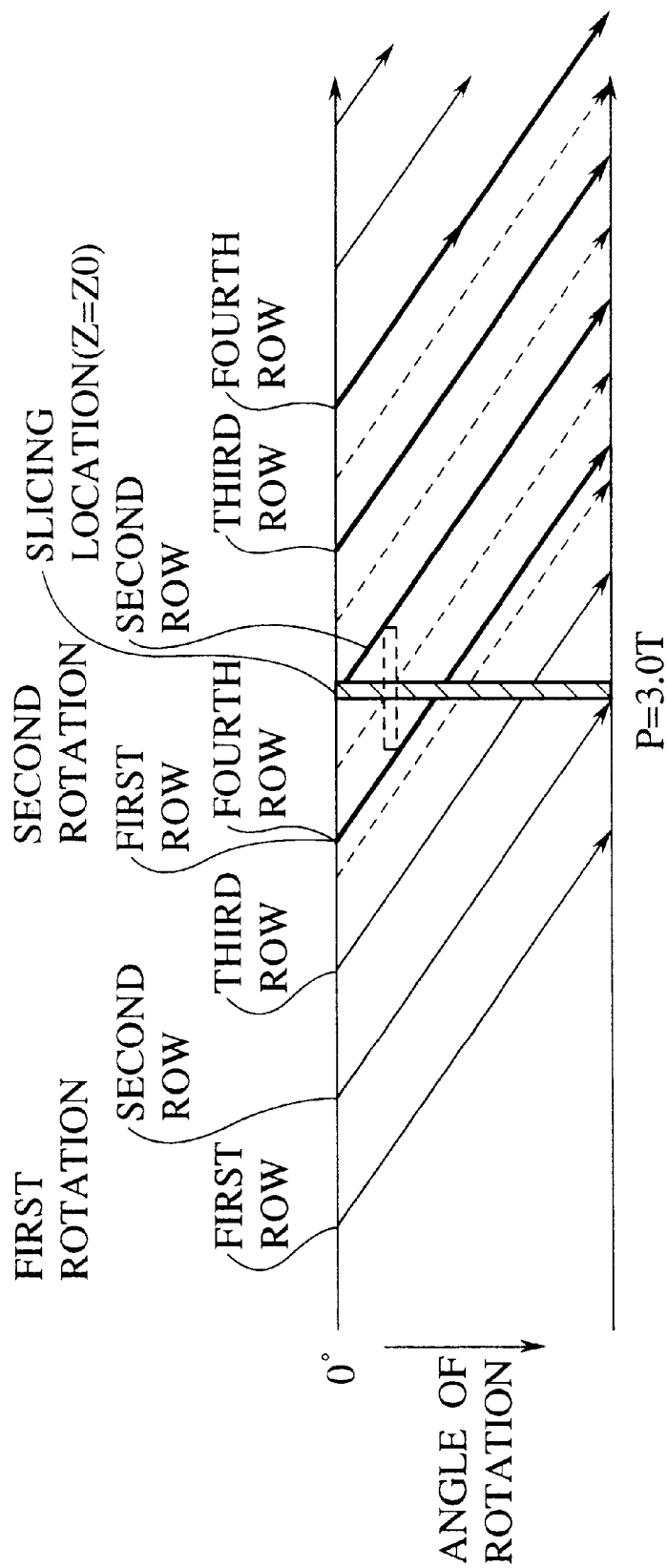
FIG. 23 is an explanatory view showing a combination of the filter-like interpolation with a helical pitch P=3.0T and the opposite beam interpolation on the X-ray CT apparatus of the fourth embodiment using four rows of detector elements.
Figure 24:
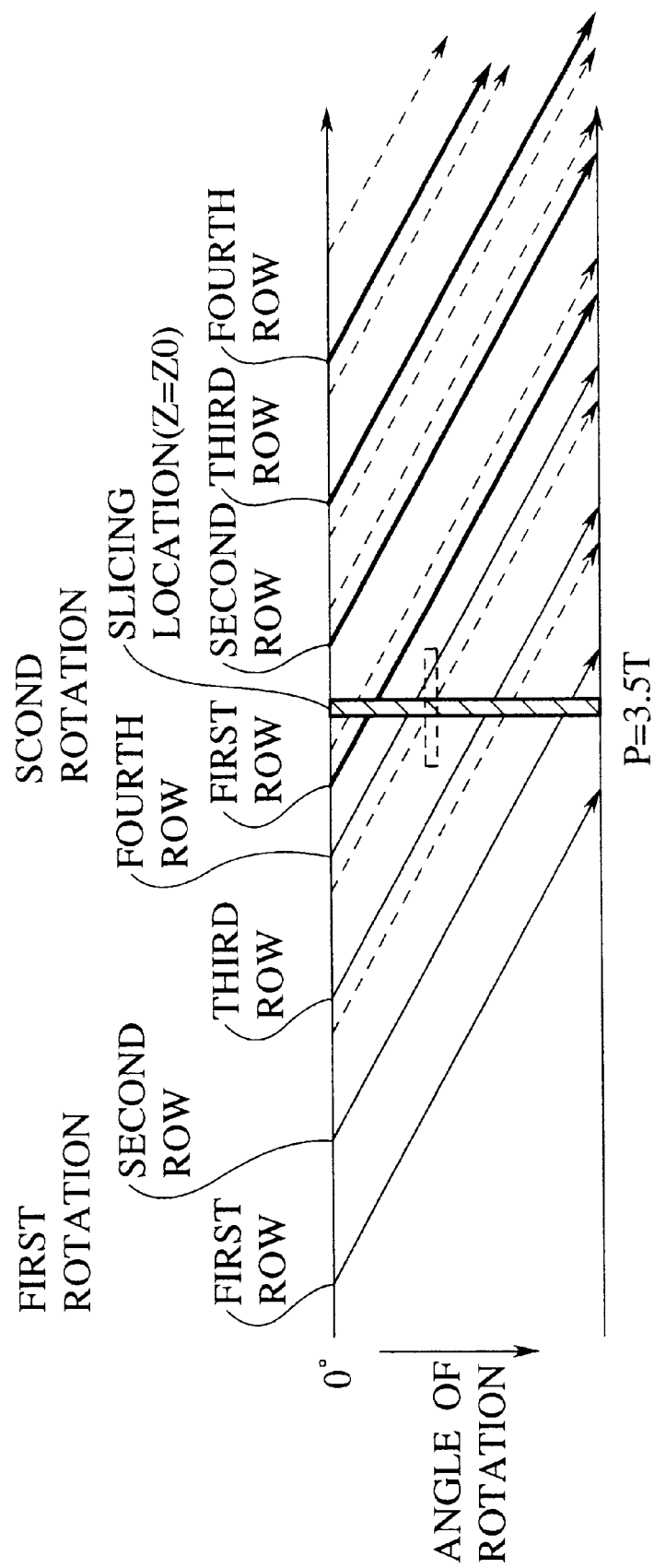
FIG. 24 is an explanatory view showing a combination of the filter-like interpolation with a helical pitch P=3.5T and the opposite beam interpolation on the X-ray CT apparatus of the fourth embodiment using four rows of detector elements.
Figure 25:
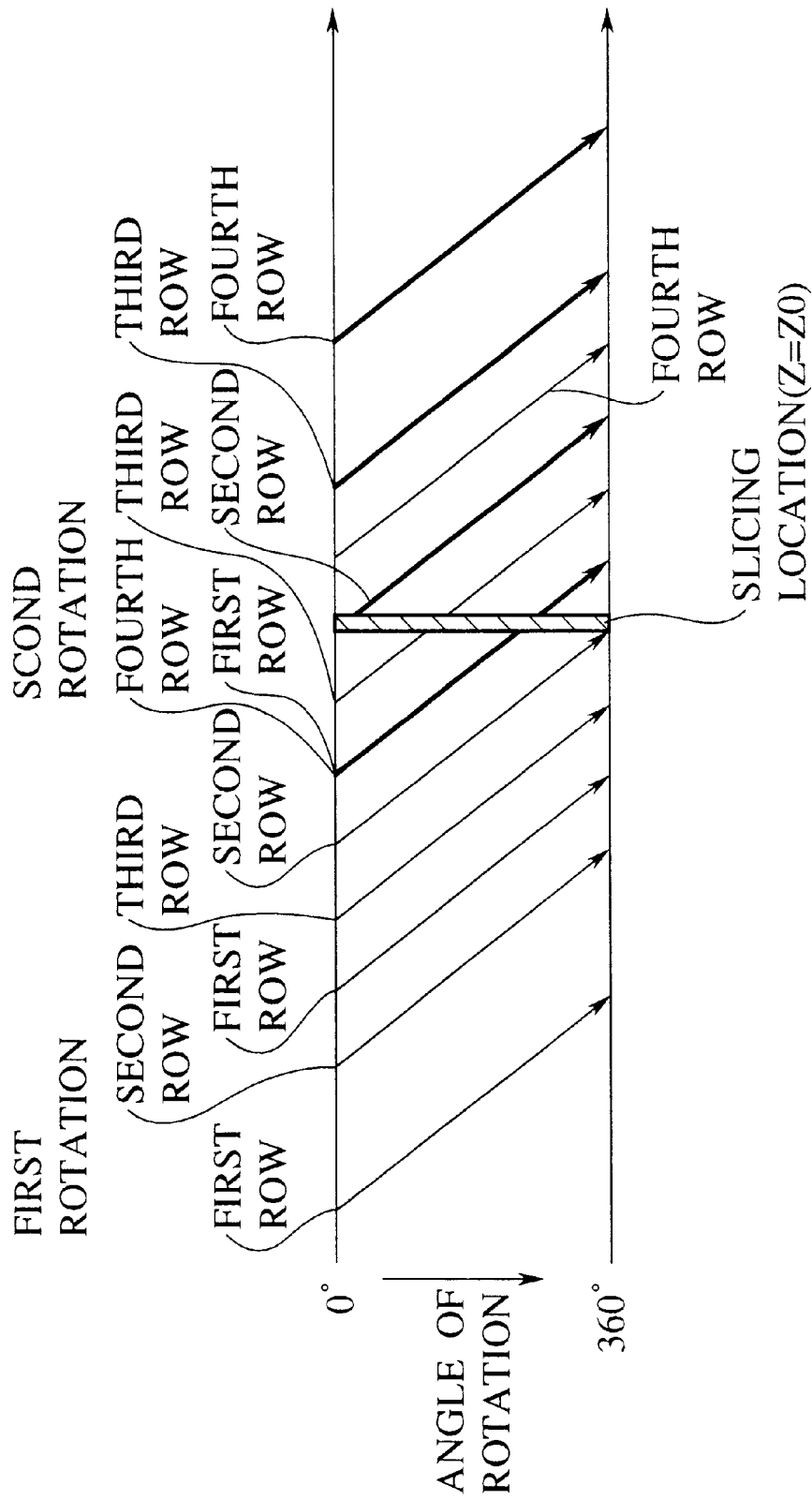
FIG. 25 is an explanatory view showing a conventional interpolation with a helical pitch P=(N/2−0.5)×T.

As compared with the conventional interpolation shown in FIG. 25, the interpolations shown in FIGS. 22, 23, and 24 is greater in the helical pitch P by one row, 1.5 rows, and 2 rows respectively but identical in the sampling density. Hence, the helical CT scanning with the helical pitches P of FIGS. 22, 23, and 24 can increase the sampling density and enhance the effect of the filter-like interpolation.

The helical pitch P may be determined so that the slicing location of the original beam is dislocated from that of its opposite beam. The sampling density is optimum with P=1.5T and P=2.5T when the rows of the detector elements are 2 and 4 respectively, thus giving almost equal sampling intervals without biasing.

The X-ray CT apparatus of the fourth embodiment provides a combination of the filter-like interpolation and the new opposite beam interpolation in which the helical pitch P and the beam thickness are not identical to each other thus to dislocate the opposite beams, whereby the sampling density will be increased and noise in the image reconstruction will be minimized.

The fourth embodiment of the present invention is not limited to the combination of the filter-like interpolation and the new opposite beam interpolation. The interpolation of the fourth embodiment can be conducted with equal success by either the filter-like interpolation or the new opposite beam interpolation.

A fifth embodiment of the X-ray CT apparatus of the present invention will be described (in which the adjacent interpolation is carried out with the helical pitch of 2.5, 3.5, or 4.5).

The X-ray CT apparatus of the fifth embodiment like the X-ray CT apparatus 10 of the first embodiment shown in FIG. 11 comprises a system controller 11, a gantry/couch controller 13, a couch driver 15, an X-ray controller 17, a high-voltage generator 19, an X-ray source or X-ray tube 21 having a focal point, a detector 23, a gantry 25, a DAS 27, an interpolator 29, an image reconstructor 31, and a display 33.

The system controller 11 delivers to the couch controller 13 a couch control signal indicative of the slice thickness T, the helical pitch P, and the rotating speed out of the requirements entered through an entry device not shown. Also, supplied from the system controller 11 are an X-ray beam generation control signal for controlling the generation of X-ray beam to the X-ray controller 17, an detection control signal for timing the detection of X-ray beam and a data collection control signal for collection of data to the DAS 27, and an interpolation control signal to the interpolator 29.

The gantry/couch controller 13 is responsive to the gantry/couch control signal from the system controller 11 for rotating the gantry 25 and delivering a couch drive signal to the couch driver 15.

The couch driver 15 upon receiving the couch drive signal from the gantry/couch controller 13 calculates a movement of a couch 15a per one rotation of the gantry 25 and driving the couch 15a to travel through the movement.

The X-ray controller 17 is responsive to the X-ray beam generation control signal from the system controller 11 for timing the generation of a high voltage of the high-voltage generator 19.

The high-voltage generator 19 upon receiving the X-ray control signal from the X-ray controller 17 supplies the high voltage to the X-ray source 21 for irradiation of an X-ray beam.

The X-ray source 21 is driven by the high voltage from the high-voltage generator 19 thus irradiating the X-ray beam.

The detector 23 is provided for detecting the X-ray beam irradiated from the X-ray source 21 and passed through an object to be examined.

The X-ray source 21 and the detector 23 are mounted on the gantry 25. The gantry 25 is driven by a gantry drive mechanism not shown for rotating the X-ray source 21 and the detector 23 about the center of rotation.

The DAS 27 is responsive to the data collection control signal from the system controller 11 for sampling data from X-ray signal outputs of the detector 23 and subjecting it to various processes including X-ray intensity compensation and detector sensitivity compensation to provide a raw data.

The interpolator 29 receives the raw data from the DAS 27 and performs interpolation with the raw data to produce a data at the target slicing location. The interpolator 29 may comprise a CPU and memories.

The image reconstructor 31 reconstructs a visual image from the interpolated data produced by the interpolator 29.

The image reconstructed by the image reconstructor 31 is then displayed on a monitor screen, not shown, of the display 33.

The action of the X-ray CT apparatus of the fifth embodiment is explained in which the detector 23 is of a four-row multi-slice type.

Relevant requirements for the scanning are entered by the operator through the unshown entry device. For example, the requirements are:

Scanning mode: helical scan

Pitch: 2.5

Interpolation: adjacent interpolation

Slice thickness: T

Number of data: 4

The requirements are fed to the system controller 11 which in turn initiates the system and informs the operator of readiness of the system. When the operator starts the system, the system controller 11 drives a helical scanning action with an X-ray beam irradiated according to the requirements and samples data which is then converted to a raw data. A data at the target slicing location is produced by interpolation between the raw data and processed by a known manner to reconstruct its visual image.

The interpolation with a specific helical scanning pitch according to the fifth embodiment will be explained.

Figure 9:
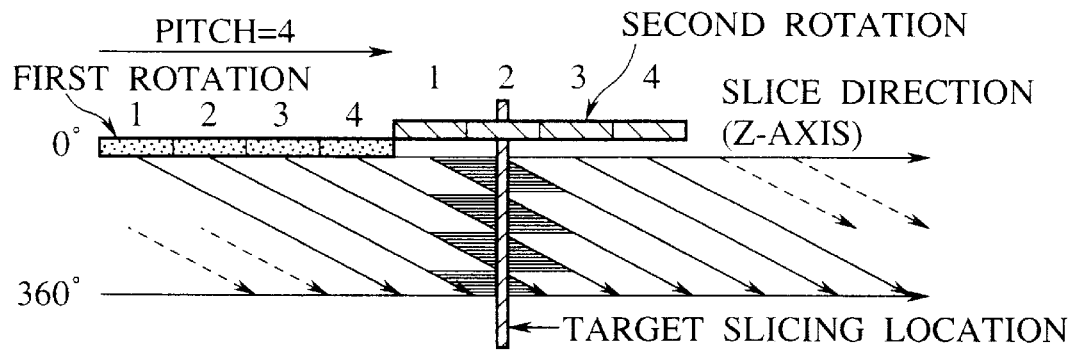
FIG. 9 is a scan diagram of the four-row multi-slice CT scanning with adjacent interpolation.
Figure 26:
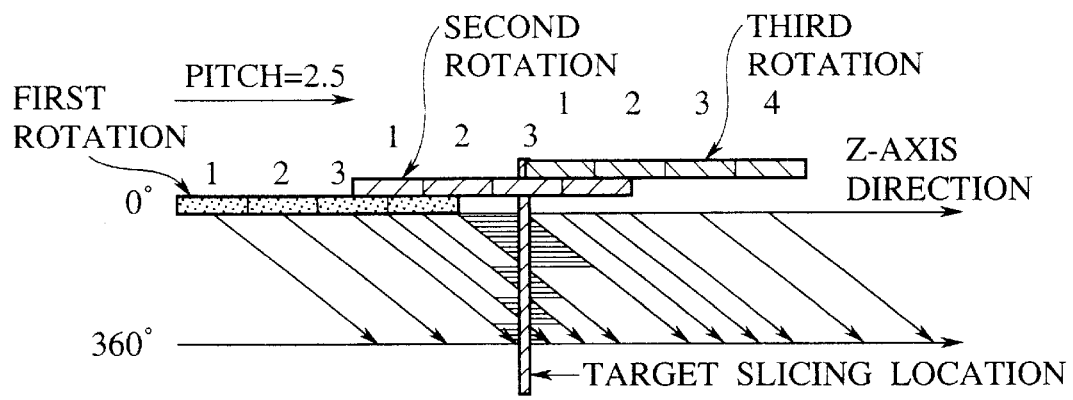
FIG. 26 is a scan diagram of the four-row multi-slice CT scanning with P=2.5.

FIG. 26 is a scan diagram at the helical scanning pitch of 2.5. The interpolation is a common adjacent interpolation using only real data. As apparent, the interpolation interval is reduced to ½ in more than a half of the full phase of 360 as compared with the scan diagram of FIG. 9 where the pitch is 4. This means that the effective slice thickness $W_{as}$ is remarkably decreased.

Figure 27:
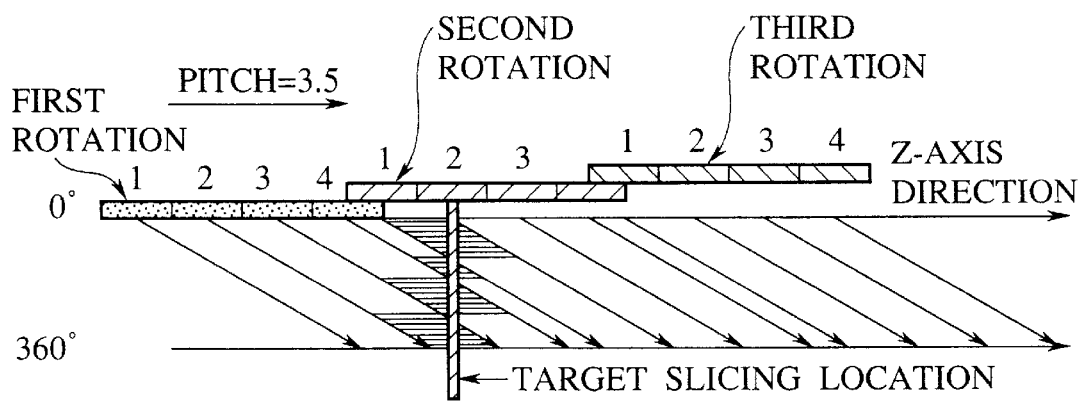
FIG. 27 is a scan diagram of the four-row multi-slice CT scanning with P=3.5.

FIGS. 27 and 28 are scan diagrams with P=3.5 and P=4.5 respectively. P=3.5 allows the interpolation interval to be smaller than with P=4.5 and so the effective slice thickness $W_{as}$. Although the interpolation interval is greater with P=4.5 shown in FIG. 28 than with P=4, it becomes even narrower than with P=2.5 when the fundamental slice thickness is reduced to a half as shown in FIG. 29.

Figure 30:
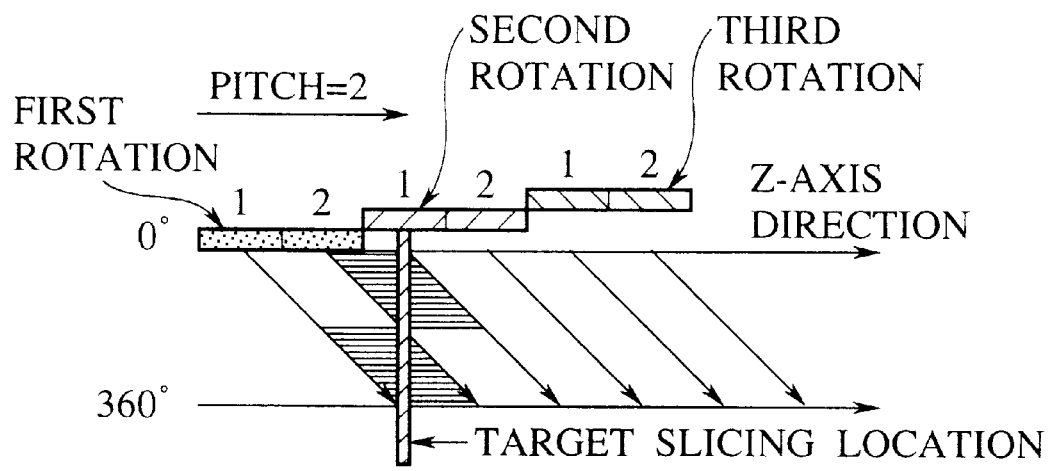
FIG. 30 is a scan diagram of the two-row multi-slice CT scanning with P=2.
Figure 31:
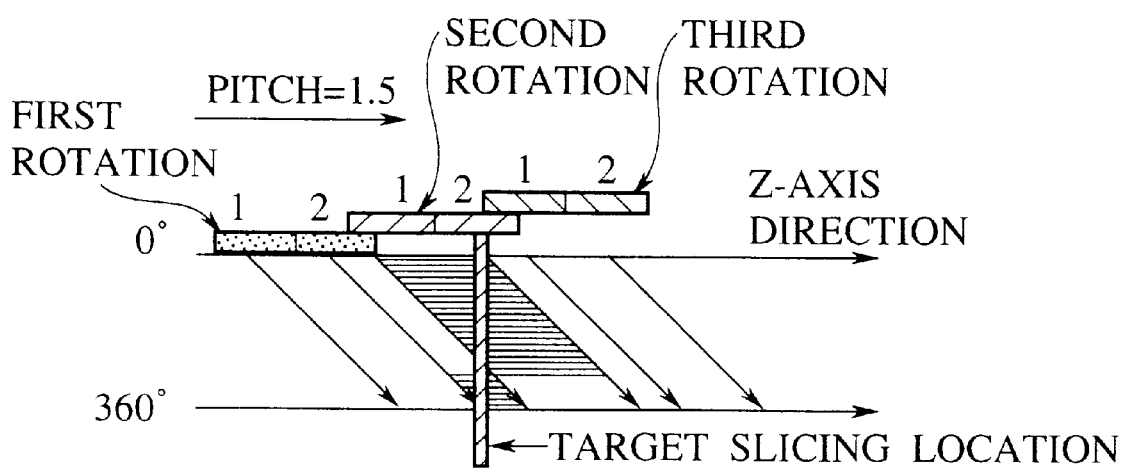
FIG. 31 is a scan diagram of a high-density sampling scanning with P=1.5.

The detector 23 may be of two-row multi-slice type. FIG. 30 is a scan diagram with P=2 while FIG. 31 is a scan diagram showing a high-density sampling scanning with P=1.5. As apparent, the interpolation interval is as small as of the four-row multi-slice scanning and so the effective slice thickness $W_{as}$.

As described above, the X-ray CT apparatus of the fifth embodiment allows the fundamental slice thickness and the helical pitch to be determined so that the interpolation interval is decreased and the sampling density is increased, whereby an image of high quality will be reconstructed.

A sixth embodiment of the present invention will be described (in which the new opposite beam interpolation is employed). An X-ray CT apparatus of the sixth embodiment is identical to that of the fifth embodiment.

The fundamental slice thickness and the helical pitch of the multi-slice type helical CT scanning are determined so that the real data do not overlap one over the other in sweep pattern and the density of sampling real data is increased in the fifth embodiment.

The sixth embodiment employs the new opposite beam interpolation in which a high-density sampling scanning is involved. More particularly, the substantial slice thickness and the helical pitch in the multi-slice type helical CT scanning are determined so that the real data hardly overlap one over the other in the sweep pattern while the opposite beams rarely overlap one over the other, whereby the density of sampling the real data and the opposite beams in total will be increased.

It should be noted that the number of rows of the detector elements for the multi-slice type scanning is not limited to two or four. The helical pitch may be determined other than the above values. It is thus understood that various changes, modifications, and applications are possible without departing from the spirit of the present invention.

The interpolation of the sixth embodiment for the helical CT scanning is explained as different from that of the fifth embodiment.

The new opposite beam interpolation is defined in which two beams (of data) which are located most close to and on both sides of the target slicing location are selected for each channel from groups of real data and opposite beams and used for weighted interpolation. The weighted interpolation may be either linear interpolation with an inverse of the ratio of interpolation interval or non-linear interpolation. The groups of data from which the two interpolating beams are selected are sampled at different spatial sampling locations and timings of the detector. The new opposite beam interpolation is differentiated from a known opposite beam interpolation manner, which interpolates between a real data closest to the target slicing location and its opposite data, by the fact that the real data is varied depending on the channels and by the fact that the interpolation is sometimes made between opposite data or between real data.

FIG. 30 is a scan diagram of the fifth embodiment in which the sampling location of an opposite beam at the center channel overlaps with that of its real data. Let us think of the opposite beam of some channel which is not the center channel. As shown at the lower in FIG. 32, beams for real data are irradiated from the focal point to the first, N1-th, the center, N2-th, . . . and the 1000th channel. The real data beams incident on the N1-th and N2-th channels are dislocated by an angle θ from the center channel in the fan angle.

Figures 5A, 5B, 5C, 5D:
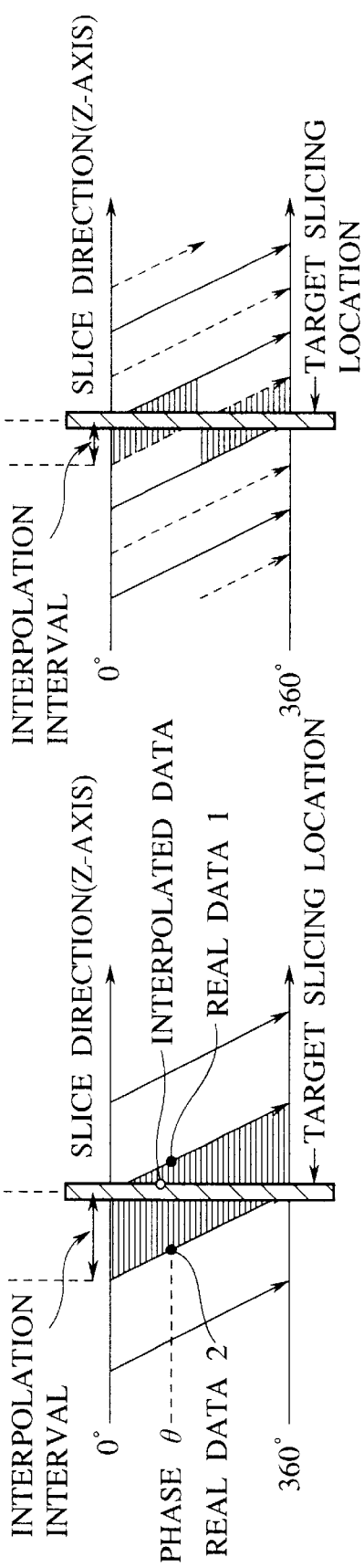
FIGS. 5A to 5D are explanatory views showing 360-degree interpolation, counter-beam interpolation, opposite beams, and sampling locations of opposite beams.
Figure 32:
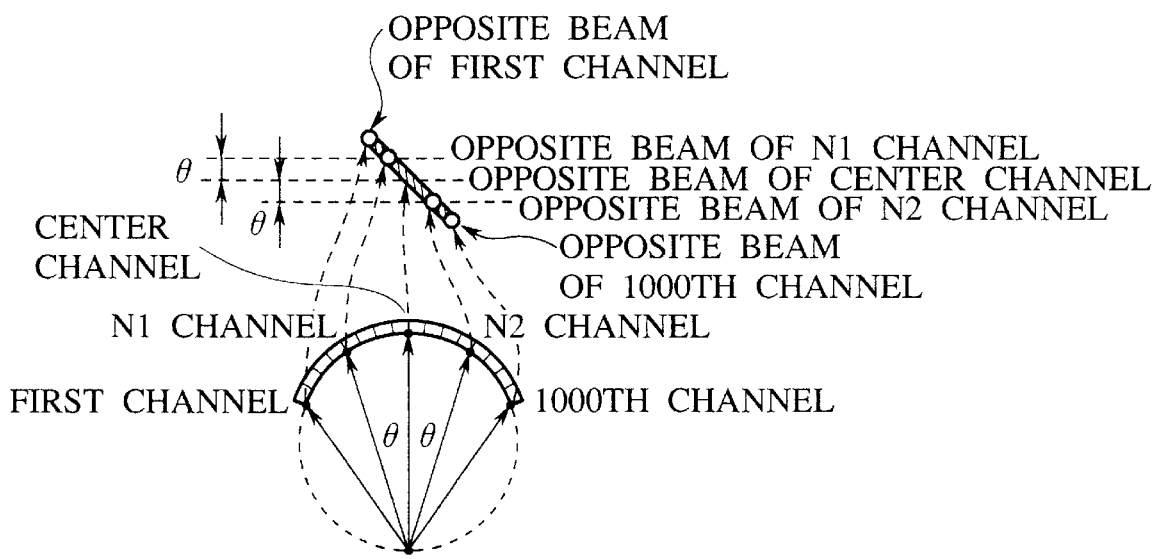
FIG. 32 is a view showing the real data beams and their opposite beams of the first, N1, center, N2, and 1000th channels.

Referring back to FIG. 5D, the opposite data of a real data is produced by extracting an opposite beam in each channel from the data at the focal point shown at the upper in FIG. 32. If P=2, the real data and the opposite beams in the N1-th channel are expressed by the real and dotted lines respectively in a scan diagram of FIG. 33A. On the contrary, the real data and the opposite beams in the N2-th channel are as shown in FIG. 33B. As apparent, the sampling location of the opposite data in the N1-th channel is located on the left side of the real data (as shifted to the negative direction of Z axis) while the sampling location of the opposite data in the N2-th channel is located on the right side of the real data (as shifted to the positive direction of Z axis). Although the sampling location of the real data remains the same throughout the channels, the sampling location of the opposite beams is varied depending on the channels.

Figure 33A:
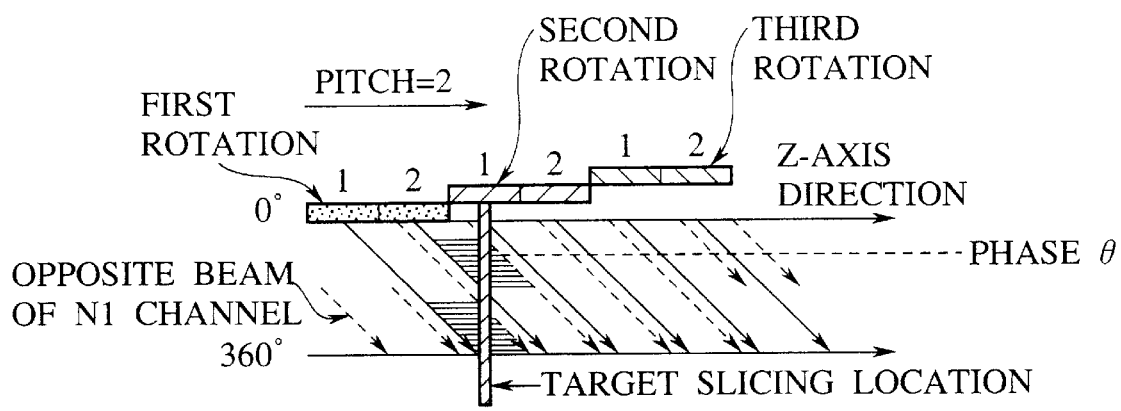
FIGS. 33A and 33B are scan diagrams showing opposite beams of the N1 and N2 channels respectively denoted by the dotted lines and their real data denoted by the real lines in the two-row multi-slice CT scanning with P=2.
Figure 33B:
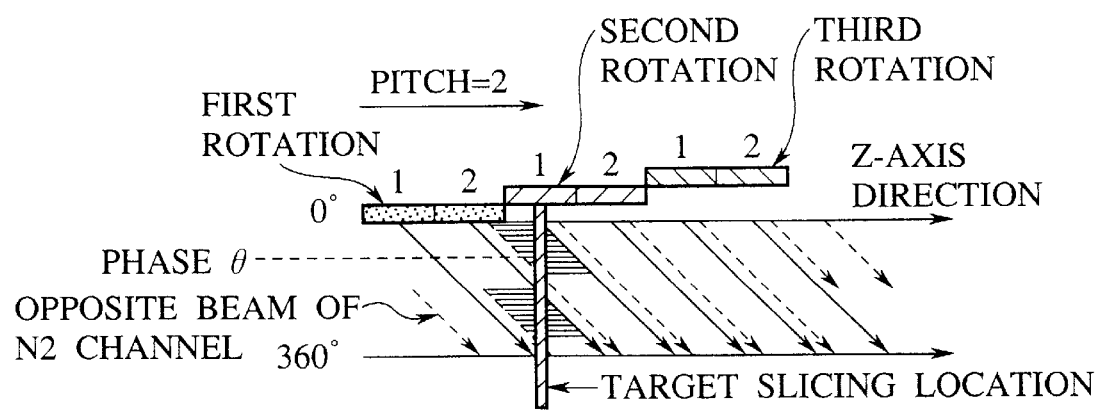

The new opposite beam interpolation allows the interpolating data to be selected for the N1-th and N2-th channels separately as shown in FIGS. 33A and 33B respectively. For example, at the phase θ of the N1-th channel, the interpolation is made between the second row real data of the first rotation and the second row opposite beam of the first rotation. As understood, the selection of data and the weighting of interpolation are different between channels. This method is not intended to solve one of the two major drawback that the beam sampling location is discontinuous between two adjacent channels, but enables to overcome the other that the weighting of interpolation is discontinuous between two adjacent channels. In addition, the process is stable interpolation but not extrapolation hence improving the quality of a reconstructed image. The distance between two interpolating beams or interpolation interval is smaller than that shown in FIG. 30 and so the effective slice thickness $W_{as}$. This method is standardized as the N-row multi-slice type helical CT scanning is conducted with P=N. More specifically, this embodiment is successfully applicable to the four-row multi-slice helical CT scanning with P=4.

It is assumed that the high-density sampling helical scanning is made with P=1.5 on a two-row multi-slice CT apparatus.

Figure 34:
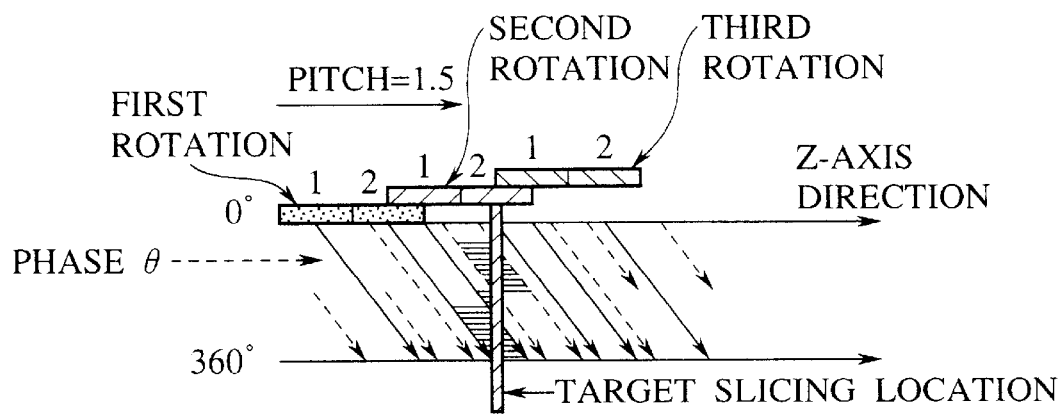
FIG. 34 is a scan diagram of a high-density sampling helical scanning of the two-row multi-slice CT mode with P=1.5.

FIG. 34 is a scan diagram in which the high-density sampling helical scanning is conducted with P=1.5 on the two-row multi-slice type CT apparatus. A sweep of the opposite beam in the center channel is denoted by the dotted line.

In the high-density sampling scanning, the value determined by dividing the pitch by two is not an integer (P/2≠integer or P≠even value). This allows the sampling location of the opposite beam in the center channel to be dislocated from that of the real data. As the sampling location of the opposite beam is not overlapped with that of the real data, the density of sampling both the real and opposite data is thus increased. Hence, the interpolation interval is substantially equal to or decreased to a half of the single-slice scan type opposite beam interpolation (FIG. 5B) and so the effective slice thickness $W_{as}$. It is also apparent that the interpolation is made between the opposite beams about the phase θ and between the real data close to 360.

As easily understood, the helical pitch is determined so that the sampling density in a primary region is increased without overlapping of the sampling locations, because the sampling location of the opposite beam in N1, N2, or any other channel than the center channel is dislocated from the center channel to the positive direction of Z axis. The effective field of view FOV may vary depending on the conditions of an object. It should be noted that, the scanning across e.g. a head produces effective data of the channels close to the center channel and the sampling density far from the center channel will not affect the quality of a reconstructed image. FIG. 34 illustrates a high-density sampling scanning in which the sampling density is increased in a primary or center region of the reconstructed image as peaked around the center channel.

The new opposite beam interpolation in a high-density sampling helical scanning of the four-row multi-slice CT mode with P=2.5 is explained.

Figure 35:
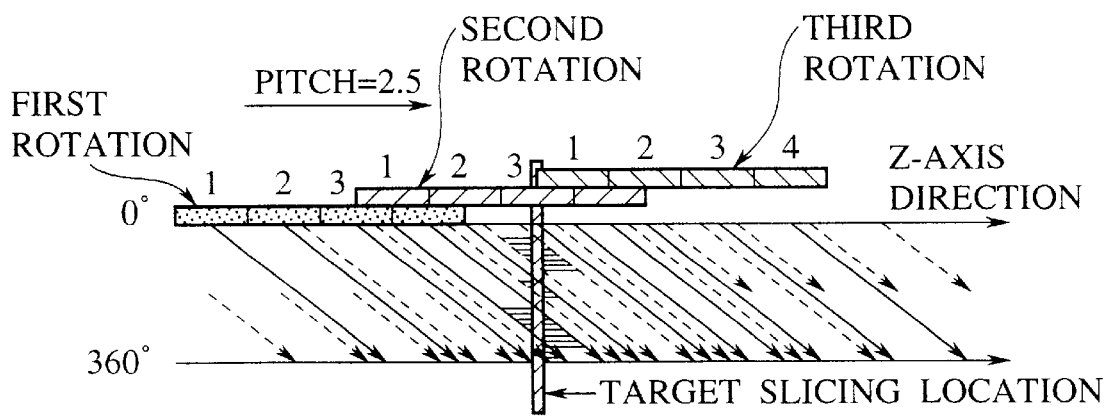
FIG. 35 is a scan diagram of a high-density sampling helical scanning of the four-row multi-slice CT mode with P=2.5.

FIG. 35 is a scan diagram showing the high-density sampling helical scanning of the four-row multi-slice CT mode with P=2.5. Similar to FIG. 34, the interpolation between opposite beams and between real data allows the interpolation interval to be minimized and so the effective slice thickness $W_{as}$.

Figure 36:
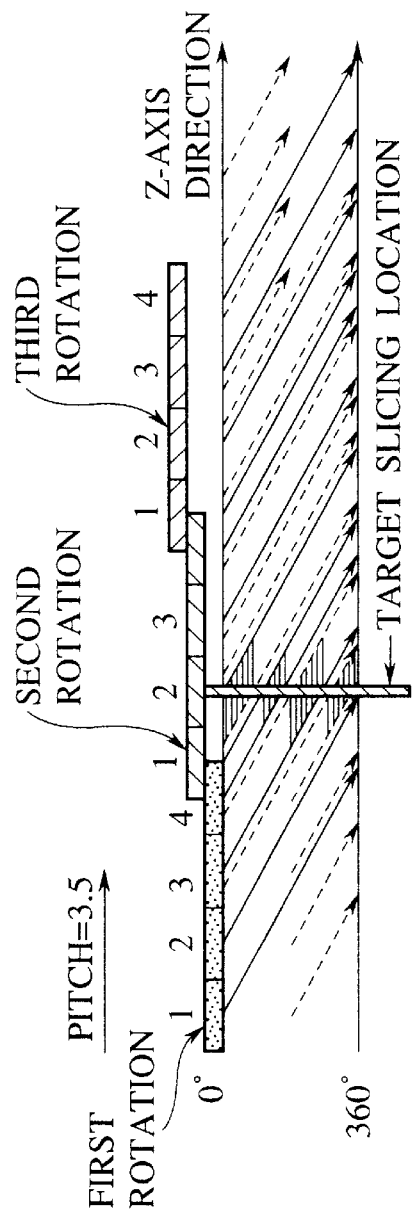
FIG. 36 is a scan diagram of a high-density sampling helical scanning of the four-row multi-slice CT mode with P=3.5.

FIG. 36 is also a scan diagram showing a high-density sampling helical scanning of the four-row multi-slice CT mode with P=3.5. As apparent, the interpolation interval is smaller than that of the adjacent interpolation with P=4 Shown in FIG. 9 and so the effective slice thickness $W_{as}$, although it is less than that with P=2.5 of FIG. 35.

Figure 37:
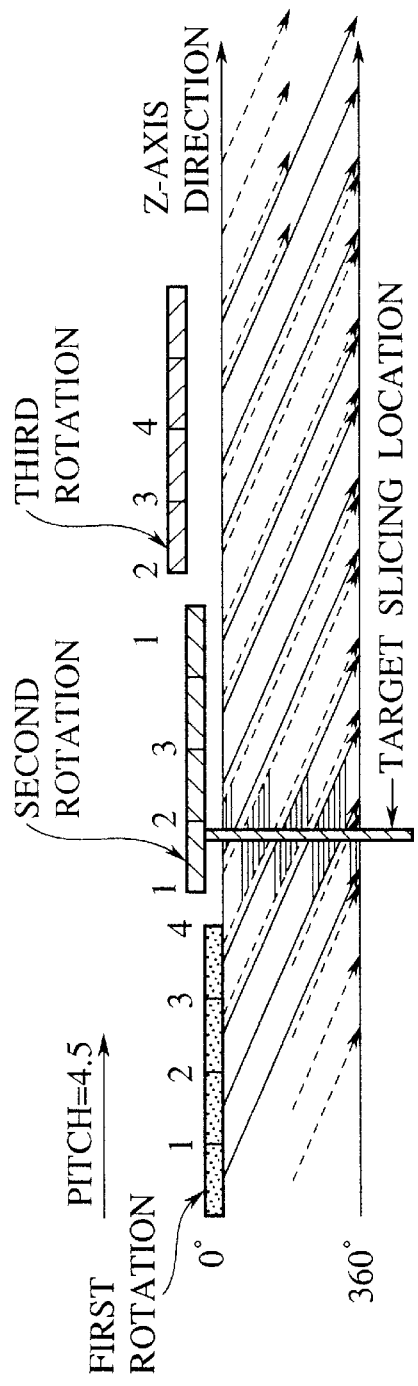
FIG. 37 is a scan diagram of a high-density sampling helical scanning of the four-row multi-slice CT mode with P=4.5.

FIG. 37 illustrates a scan diagram of a high-density sampling helical scanning of the four-row multi-slice CT mode with P=4.5. A apparent, the interpolation interval is smaller than that of the adjacent interpolation with P=4 shown in FIG. 9, the interpolation interval is narrower despite of the greater helical pitch. In this high-density sampling helical scanning of the four-row multi-slice CT mode with P=4.5, the interpolation interval will be further decreased if the fundamental slice thickness is minimized as shown in FIG. 29.

It is now understood that the new opposite beam interpolation and its combination with the high-density sampling scanning are advantageous. As described, the high-density sampling scanning with the new opposite beam interpolation is characterized by the real data being not overlapped each other in the sweep pattern, and both the fundamental slice thickness and the helical pitch being selectively optimized to increase the sampling density of the real data in the multi-slice CT mode helical scanning. More specifically, it is not a simple scanning method concerning the total sampling density but a novel method in which either the real data and their opposite data are not (or least) overlapped one another in the sweep pattern and also, the fundamental slice thickness and the helical pitch are selectively determined to have such a sweep (sampling) pattern that the total sampling density including the real data and their opposite data is increased. "Least" is used because the sampling location of the opposite beam depends on channels. In some channels, the opposite beams may overlap at the sampling location with the real data. If the sampling locations are aligned with each other, the helical pitch is determined so that the sampling density of such a data as from the center channel which largely affects the quality of a desired reconstructed image.

The sampling density is increased as the helical pitch decreases. For example, a maximum of the density of the four-row multi-slice CT mode is gained by the high-density sampling helical scanning with P=1.5. The higher the sampling density, the smaller the helical pitch becomes but the longer the scanning duration takes. Therefore, the density may be determined depending on the purpose of scanning.

The number of rows of the detector elements is not limited to two or four and any number of rows will be employed with equal success. The helical pitches described are not of limitation and various modifications, changes, and applications will be possible without departing the spirit of the present invention.

As describe, the X-ray CT apparatus of the sixth embodiment allows the two (data) beams located most close to and on both sides of the target slicing location to be selected separately in each channel from the read data and their opposite beams of the multi-slice CT scanning and used for weighted interpolation, whereby the quality of a resultant reconstructed image will be enhanced.

A seventh embodiment of the X-ray CT apparatus of the present invention will now be described (in which the interpolation is implemented by direct filtering). The X-ray CT apparatus of the seventh embodiment is substantially identical in the construction to that of the sixth embodiment and its interpolation of helical scanned data is explained which is different from that of the sixth embodiment.

A filter-like interpolation with the direct filtering is provided in which data of plural beams which are in phase with each other and oriented in the same direction within a range adjacent to the target slicing location are filtered along the slice direction to produce a data at the target slicing location of which phase and beam direction are identical to those of the plural beams. (In theory, it is hence equivalent to a filtering along the Z axis rather than interpolation.)

The procedure includes the high-density sampling helical scanning of data described in the fifth embodiment, the sampling of opposite beams with the new opposite beam interpolation described in the sixth embodiment, and the filter-like interpolation to produce a desired data at the target slicing location.

Figure 38:
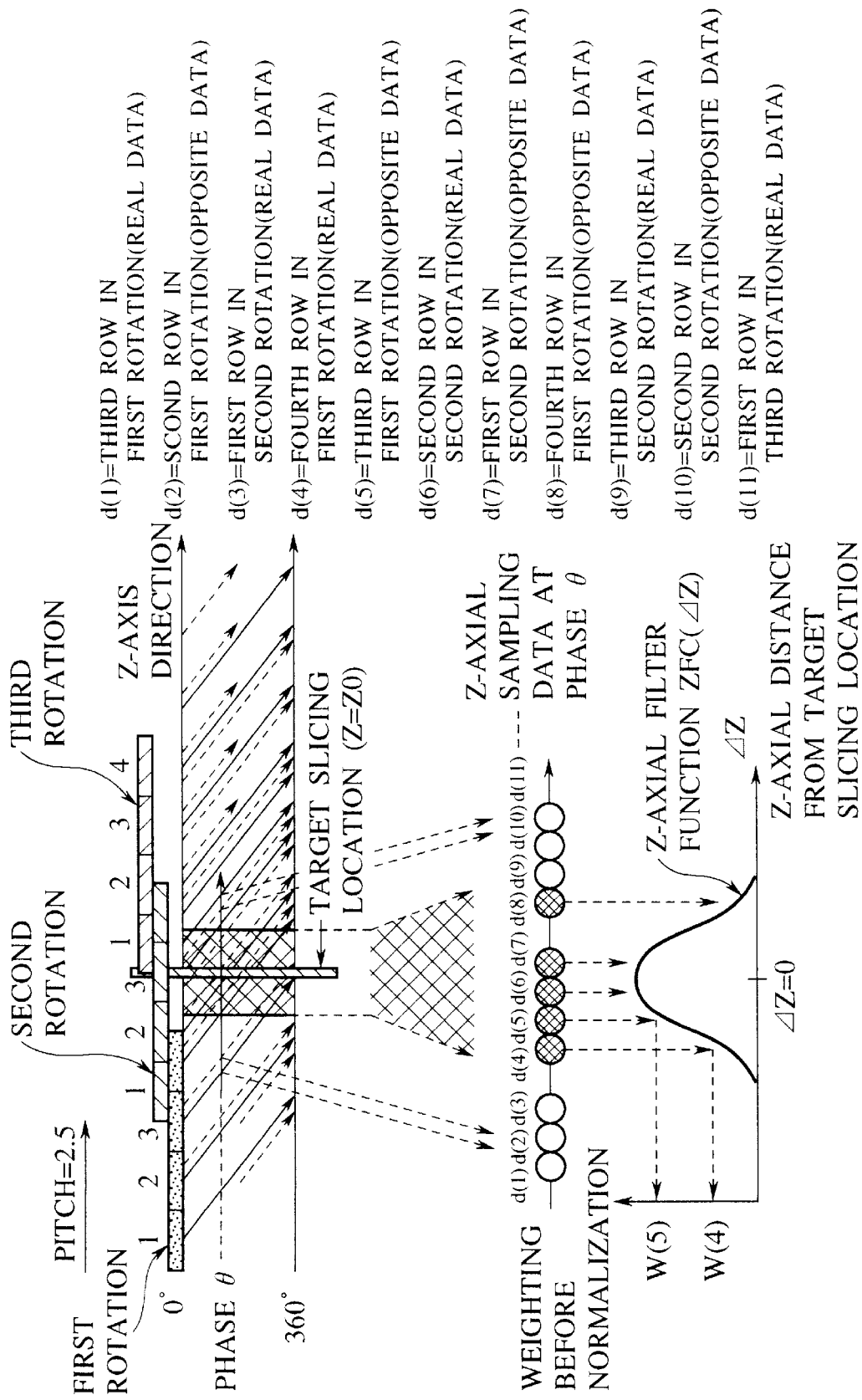
FIG. 38 is an explanatory view showing the filter-like interpolation of opposite beams in a high-density sampling helical scanning of the four-row multi-slice CT mode with P=2.5.

FIG. 38 illustrates at the upper a scan diagram of a helical scanning of the four-row multi-slice CT mode with P=2.5. A shaded square area represents an adjacent area to the target slicing location Z=Z0.

Shown at the lower in FIG. 38 is a data d(i) sampled from the adjacent area about the target slicing location at a phase point θ. The sampled data is then filtered using the filtering function ZFC(ΔZ) along the slice direction for filter-like interpolation. It is assumed that the number of the data is N.

First of all, weightings W(i) of sampling data d(i) at the phase point θ are acquired by using the filtering function ZFC(ΔZ) along the slice direction according to the following equations (7) and (8).

$$\Delta Z(i)=Z(i)-Z0 \qquad (7)$$

$$W(i)=ZFC(\Delta Z(i))=ZFC(Z(i)-Z0) \qquad (8)$$

Then, the weighting W(i) of the sampled data d(i) at the phase point θ is normalized to have a weighting WU(1) using an equation (9).

$$WU(i) = \frac{W(i)}{\sum_{i=1}^{N} W(i)} \qquad (9)$$

This is followed by calculating a DATA(θ) of the phase point θ at the target slicing location from an equation (10).

$$DATA(\theta) = \sum_{i=1}^{N} [WU(i) \cdot d(i)] \qquad (10)$$

By repeating the above process with the equation (7), (8), (9) and (10), data of the other phase points are calculated to reconstruct a wanted pattern of fan beam.

From the data at the target slicing locations, a desired image is reconstructed. It is noted again that the weighting of the data sampled from the defined area (real or opposite data of a particular row in a given rotation) is independent in each channel as the sampling location of opposite beams depends on the channel. Also, when a plurality of results (of width and weighting) are obtained from the filtering function ZFC, the weighting depends on ZFC.

This embodiment is not limited to the high-density sampling scanning of the four-row multi-slice CT mode with P=2.5 but will be applicable to the same mode with P=3.5 or 4.5 and to the other mode, for example, two-row multi-slice CT mode high-density sampling scanning with equal success.

Figure 6:
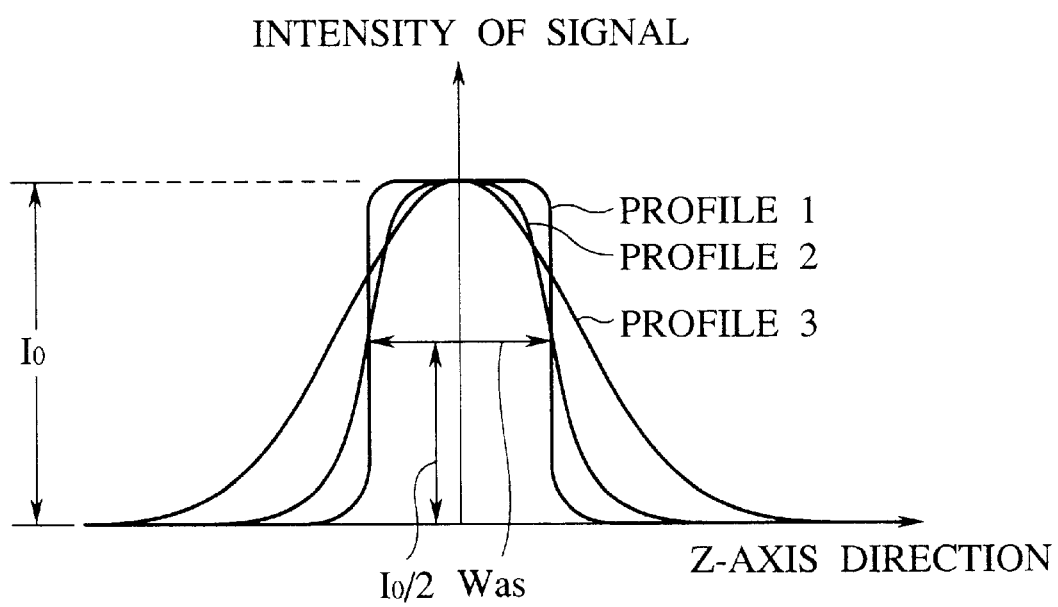
FIG. 6 is a view of slice profiles.
Figure 7A:
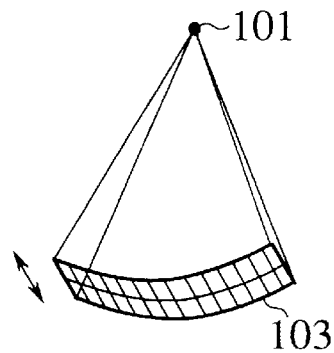
FIGS. 7A to 7C are diagrams showing two-row multi-slice CT scanning, four-row multi-slice CT scanning, and eight-row multi-slice CT scanning.
Figure 7B:
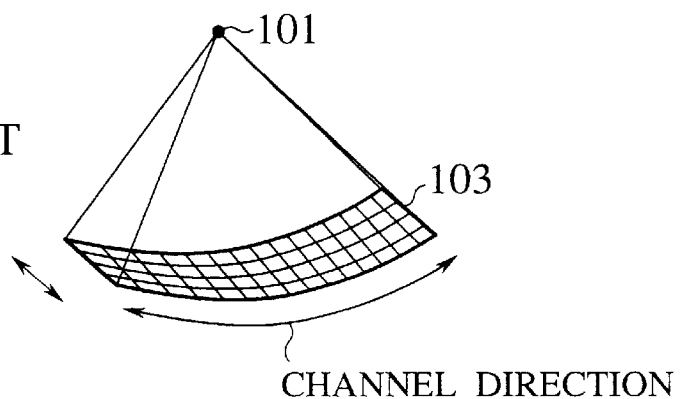
Figure 7C:
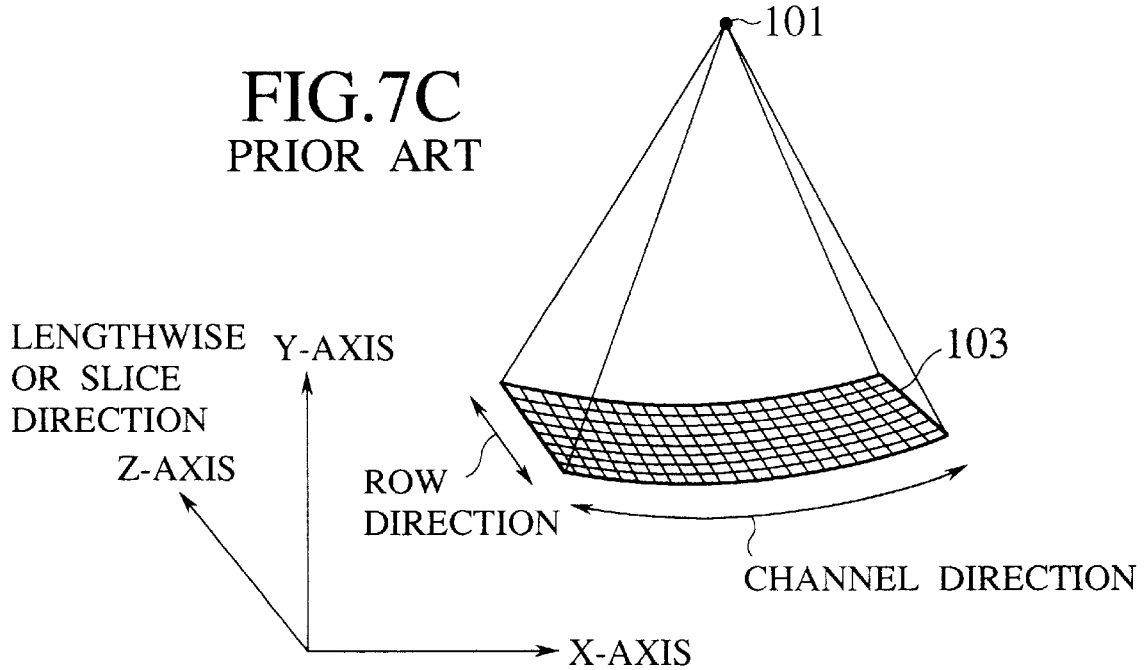
Figure 8A:
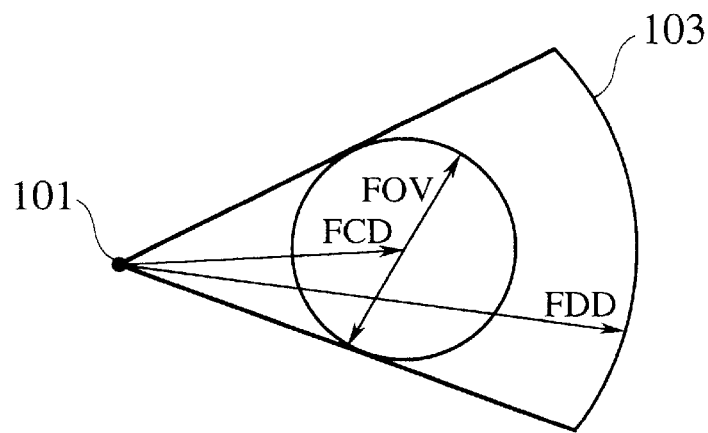
FIGS. 8A and 8B are views of the multi-slice CT scanning seen from the Z-axis direction and of the four-row multi-slice CT scanning along the Z axis seen from a direction vertical to the Z-axis.
Figure 8B:
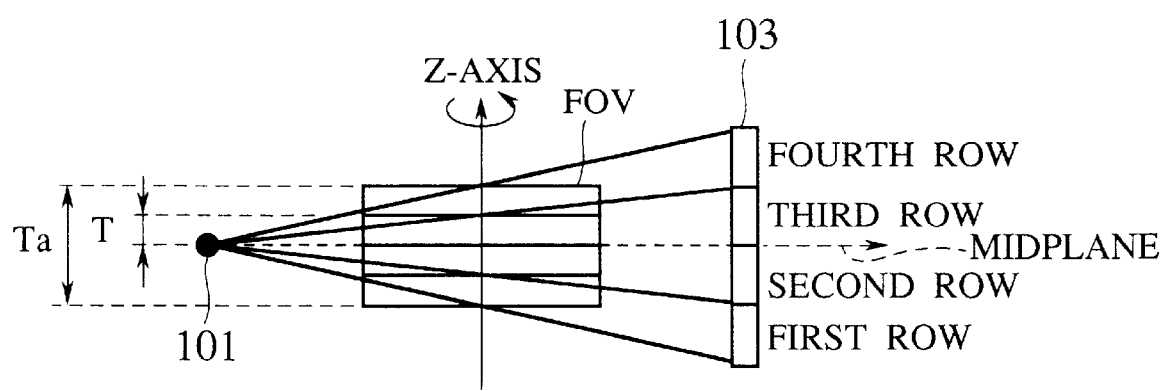
Figure 39A:
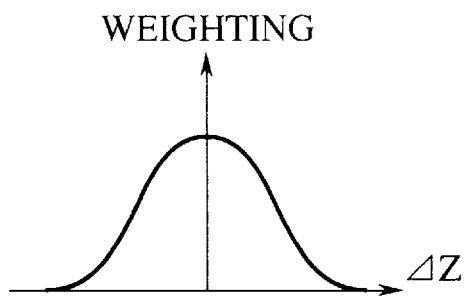
FIGS. 39A to 39F are diagrams showing patterns of a filtering function ZFC.
Figure 39B:
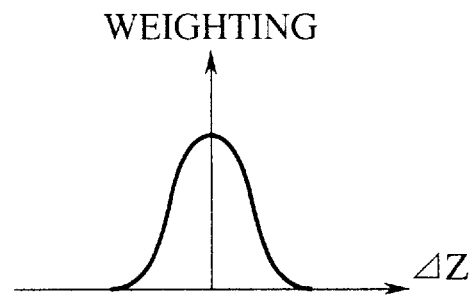
Figure 39C:
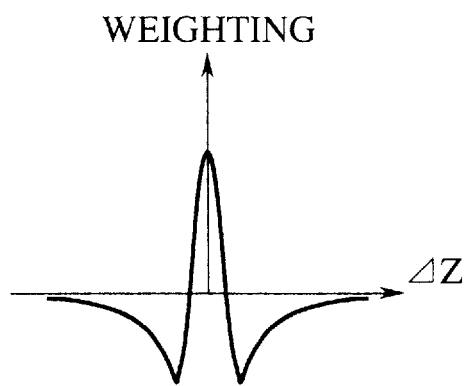
Figure 39D:
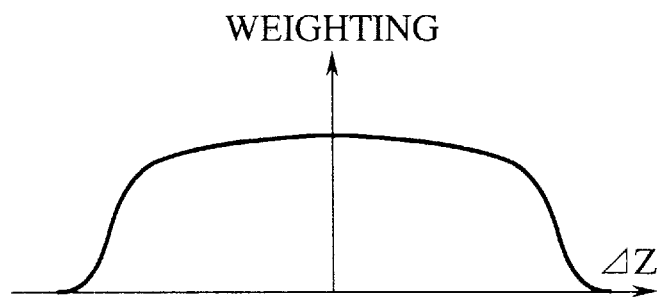
Figure 39E:
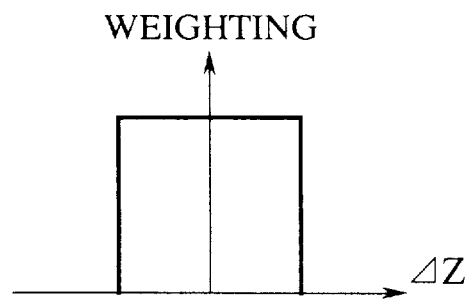
Figure 39F:
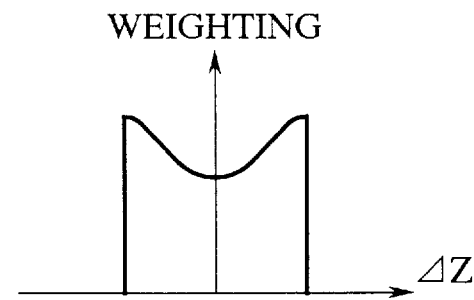

Although the embodiment employs the filtering function ZFC, another type or a series of filtering functions will be used in a sequence or selectively corresponding to the characteristics of an image to be reconstructed, such as shown in FIGS. 39A to 39F. Using desired filters, the effective slice thickness $W_{as}$ can arbitrarily be determined. As compared with the opposite beam interpolation or the adjacent interpolation, the sampled data in the embodiment contributing to the quality of a reconstructed image is increased in amount thus allowing each data to serve a smaller part. This will offset the negative factor of the detector 23 and increase the image quality. As described previously with FIG. 6, the slice profile of a helical scanned data commonly has a gaussian-like distribution but not an ideal square shape. Such a specific filter as shown in FIG. 39F may shape the slice profile to a square or quasi-square at the final stage. This means that the slice profile can be modified to any desired shape as well as an ideal square shape. When a desired shape of the slice profile is determined in advance, its relevant filter may easily be prepared by reverse operation. As the slice profile has been filtered by the calculated filter, its desired shape is gained.

In practice, such a slice profile SP2(Z) shown in FIG. 40B is predicted or calculated using a provisional filter F1($\Delta$Z) shown in FIG. 40A. If the target slice profile is SP3(Z) of FIG. 40C, a function SP4(Z) shown in FIG. 40D has to be calculated for changing the shape to SP3(Z). This may be done by dividing SP3(Z) by SP2(Z). It is thus given SP4(Z)=SP3(Z)/SP2(Z). However, such an adjustment is need that the slice profile SP3(Z) is set to not a true square but a quasi-square shape as shown in FIG. 40C or that the result of the division is slightly modified (e.g. by giving an upper limit) so as not to occur divergence on calculation with respect to both ends of a profile. Then, for producing a slice profile SP4(Z) shown in FIG. 40D, a filter F5($\Delta$Z) is calculated as shown in FIG. 40E, a filter F5(AZ) is divided by F1($\Delta$Z), a final filter F5'($\Delta$Z) shown in FIG. 40F is obtained. If the provisional filter F1($\Delta$Z) has a square shape shown in FIG. 40A, the change from F5($\Delta$Z) to F5'($\Delta$Z) is a simple normalization process.

Also, the procedure of calculating a desired shape of the slice profile may be carried out on a frequency base.

The filter-like interpolation using high-density sampling scanning with no use of opposite data is applicable. In this case, the principle is identical to that shown in FIG. 38 except data d(2), d(5), d(7), d(8), and d(10) of the opposite data denoted by the dotted lines. As no more explained in detail, the other modes including two-row CT and single-slice CT modes will be used with equal success.

The filter-like interpolation using opposite data with no use of high-density sampling scanning is also applicable. FIG. 41 is a scan diagram showing a common helical scanning of the four-row multi-slice CT mode with P=4, in which the dotted lines represent the opposite beams of N1 channel of FIG. 32 but not of the center channel.

Figure 42A:
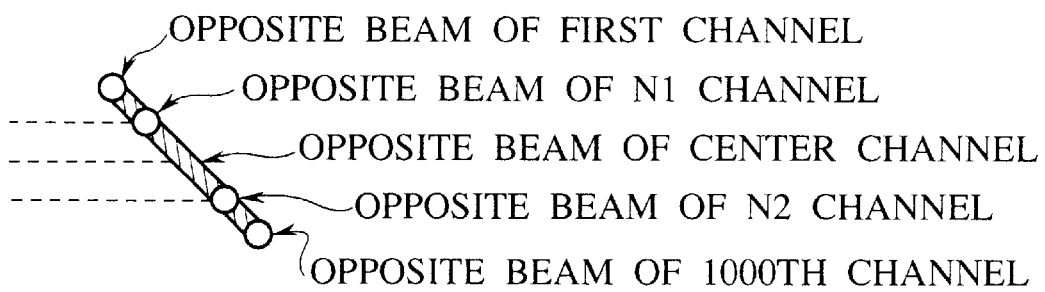
FIGS. 42A and 42B are views of opposite beams in the two-row multi-slice CT scanning with P=1.5 and P=4 respectively.
Figure 42B:
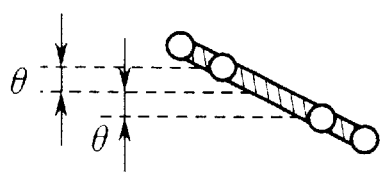

As compared with the opposite beams shown in FIG. 42B, the N1-th channel opposite beams of the two-row multi-slice CT mode with P=1.5 shown in FIG. 42A are fairly close to the sampling location of the opposite beams of the center channel, i.e. of the real data, to the negative direction of the Z axis because the sweep pattern of the real data is tilted along the Z axis. As apparent from FIG. 41, sampled data are substantially equal along the Z axis. As described, the sampling location of the opposite beams of the N2channel is dislocated in the positive direction of their real data.

The sample data d(i) shown at the lower in FIG. 41 are from a defined area adjacent to the target slicing location Z=Z0 similar to those shown in FIG. 38. The data d(1) is then filtered using the same filtering function ZFC($\Delta$Z) along the Z axis as shown in FIG. 38, thus producing a data of the N1-th channel of the phase point $\theta$ at the target slicing location. By repeating this process for data of all the channels, a group of desired data of the phase point $\theta$ at the target slicing locations are obtained. For reconstruction of an image, data throughout the phase of 360° or 180°+a fan angle are produced in the same manner and subjected to back projection.

For reconstruction of an image from data of not opposite beams sampled by a common helical scanning of the four-row multi-slice CT mode with P=4 and subjected to the filter-like interpolation at the target slicing location, the process is carried out as shown in FIG. 41 except data d(1), d(3), d(5), d(7), . . . of N1 channel opposite beams denoted by the dotted lines.

As described, the X-ray CT apparatus of the seventh embodiment allows a plurality of data sampled from a defined area adjacent to the target slice location, which are in phase to each other and aligned in the same direction, to be filtered along the slice direction, thus reconstructing an image of higher quality.

An eighth embodiment of the X-ray CT apparatus of the present invention will be described (using a combination of P=2.5, the new opposite beam interpolation, and the filter-like interpolation with resampling). The construction of the X-ray CT apparatus of the eighth embodiment is substantially identical to that of the seventh embodiment and a difference in the interpolation of helical scanned data from the seventh embodiment only is explained.

While the prescribed filter-like interpolation of direct filtering comprises filtering along the slice direction a plurality of data which are sampled from a defined area adjacent to the target slice location to produce a desired data at the target slicing location which is identical in the phase and direction to the sampled data, the filter-like interpolation with resampling is characterized by determining a plurality of slicing locations adjacent to the target slicing location which are spaced at equal intervals of a small distance, producing a group of interpolated data (resampled data) through the new opposite beam interpolation or adjacent interpolation between data sampled at the slicing locations, and subjecting the interpolated data (resampled data) to the weighted addition or filtering to have a data at the target slicing location. The principle may be similar to that of the seventh embodiment.

For ease of the description, imaginary data or resampled data V-data(i) are produced by the high-density sampling helical scanning of the fifth embodiment and the new opposite beam interpolation of the sixth embodiment and subjected to weighted addition of the filter-like interpolation for having a desired data at the target slicing location.

Figure 43:
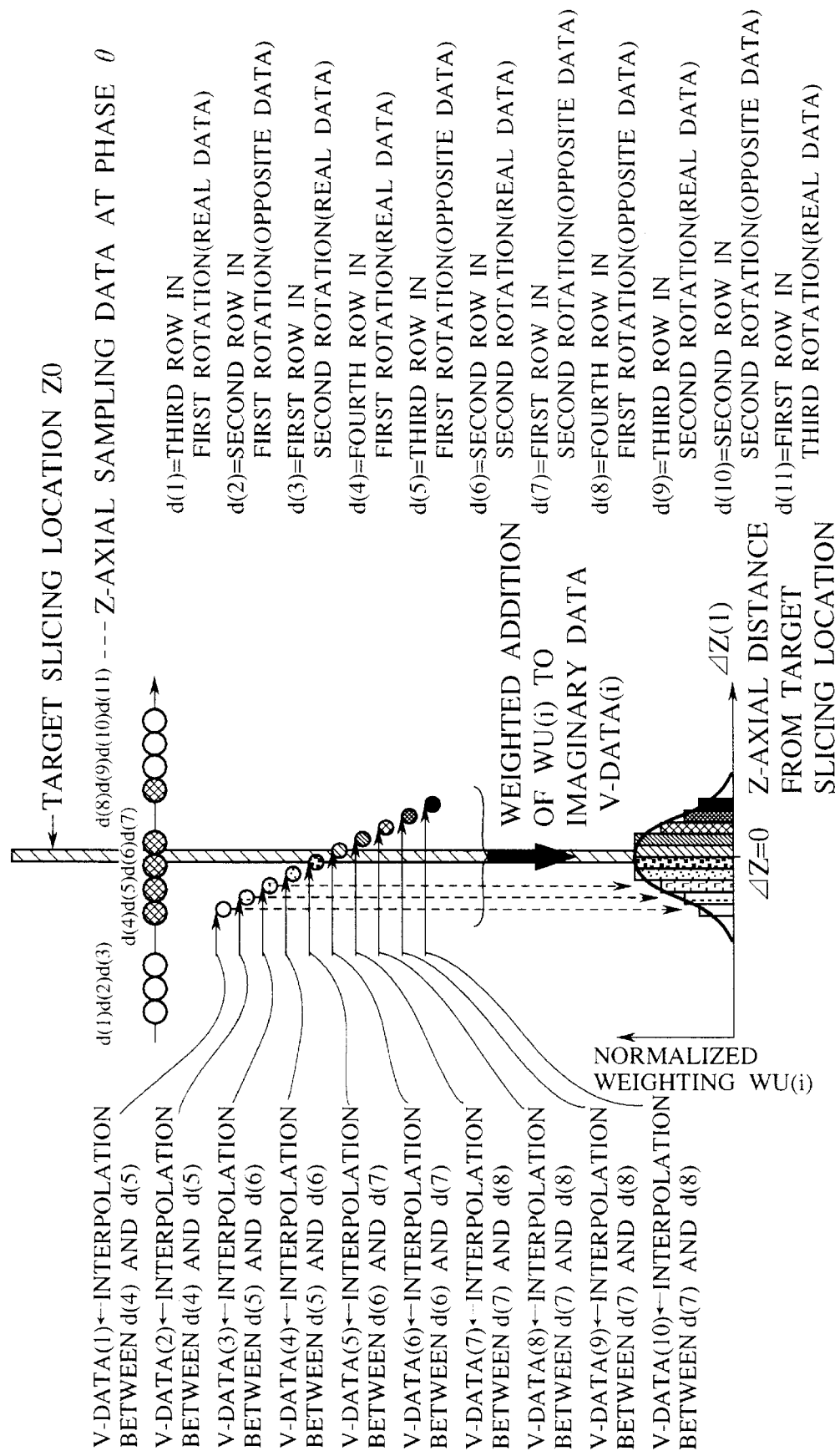
FIG. 43 is an explanatory view showing a resampling process.

FIG. 43 is a scan diagram showing a helical scanning of the four-row multi-slice CT mode with P=2.5. As shown, a series of data d(1), d(2), . . . of a phase point $\theta$ are sampled from a given area adjacent to the target slicing location Z=Z0 and aligned at the lower. It is assumed that the number of resampling points is N=10.

While the N resampling points are defined in the given area adjacent to the target slicing location Z0, the resampled data V-DATA(i) at the resampling points are calculated by linear, new opposite beam interpolation between two data d(j) and d(j+i) using an equation (11).

$$\text{V-DATA}(i) = w \cdot d(j) + (1-W) \cdot d(j+1) \tag{11}$$

Then, using an equation (12), DATA($\theta$) of the phase point $\theta$ at the target slicing location Z0 is calculated by subjecting the resampled data V-DATA(i) to weighted addition with a normalized weighting WU(i).

$$DATA(\theta) = \sum_{i=1}^{N} [WU(i) \cdot V - DATA(i)] \quad (12)$$

This method compensates an increased number of resampling data interpolating actions with the normalization of a weighting since the target slicing location is fixed relative to the resampling points. Also, the spatial resolution of the data along the slice direction will be modified using a desired weighting as shown at the lower in FIG. 43, or in FIGS. 39A to 39F or FIG. 40.

The interpolation for producing resampled data is not limited to the new opposite beam interpolation and other applicable interpolation methods including adjacent interpolation and non-linear interpolation will be used with equal success. Also, this embodiment like the sixth embodiment is of no limitation in the helical pitch and the number of the detector elements and will be applicable to the single-slice CT mode.

It is also understood that the filter-like interpolation with resampling and the filter-like interpolation of direct filtering are linearly carried out in this order or a revere sequence as permitted in arithmetic process.

A×B×C=(A×B)×C=A×(B×C)

Figure 44:
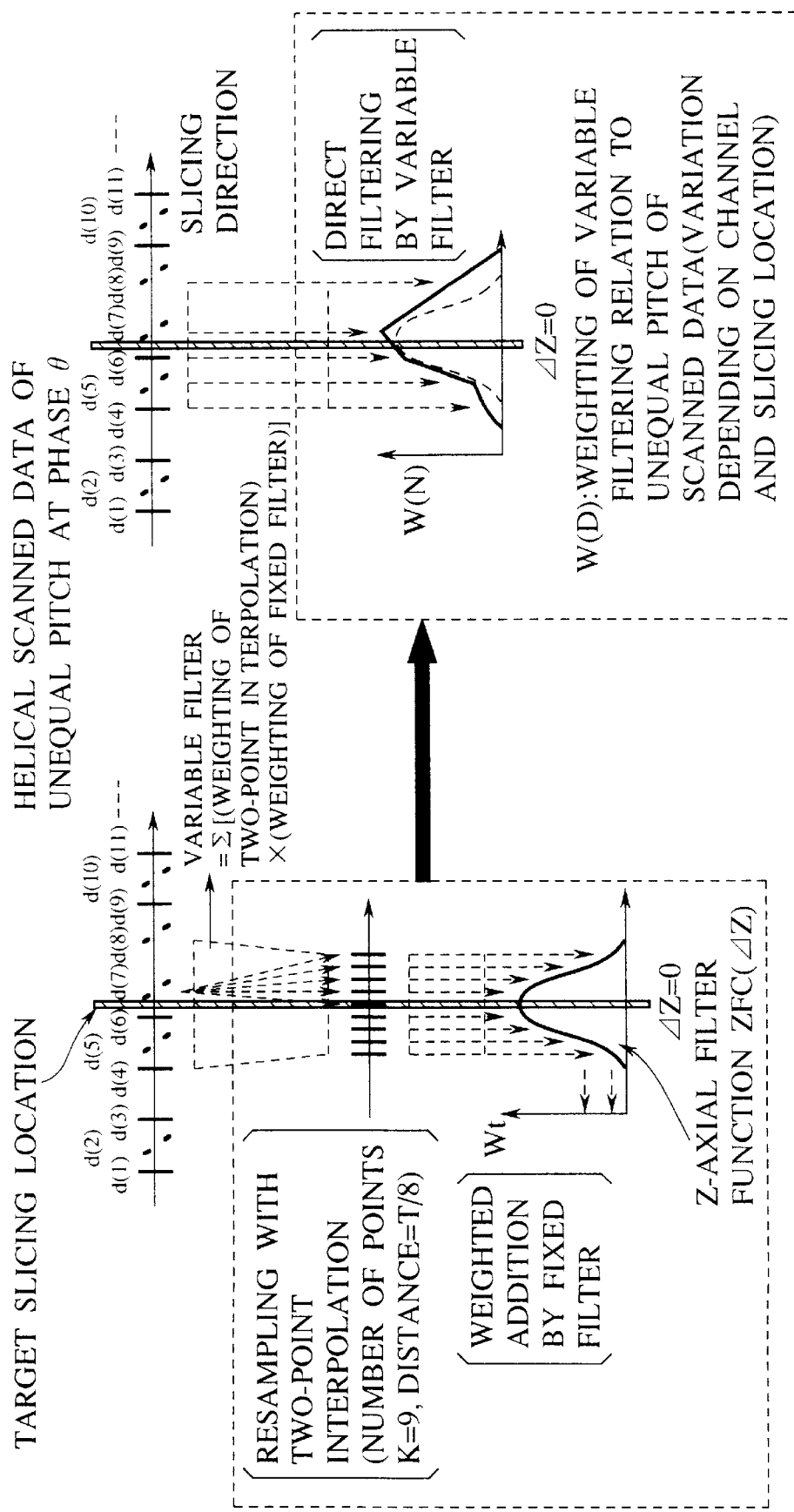
FIG. 44 is an explanatory view showing the resampling and its equivalent process using a direct filter-like interpolation.

FIG. 44 shows at the left a two-step resampling mode in which raw data is sampled to have resampled data and the resampled data is filtered. This is equivalent to the center section of the above equation.

Also, as shown at the right in FIG. 44, the resampling of location-dependent two-point interpolation and the filtering of weighted addition of no location-dependent are performed on the raw data. In other words, the raw data may be processed with a variable filter having location-dependency. This is intermediate between the seventh and eighth embodiments.

As described, the X-ray CT apparatus of the eighth embodiment comprises the steps of determining a plurality of slicing locations adjacent to the target slicing location which are spaced at equal intervals of a small distance, producing a group of interpolated data (resampled data) through the new opposite beam interpolation or adjacent interpolation between data sampled at the determined slicing locations, and subjecting the interpolated data (resampled data) to the weighted addition or filtering to have a data at the target slicing location, whereby the quality of a reconstructed image will be improved.

A ninth embodiment of the X-ray CT apparatus of the present invention will be described (using a combination of P=2.5, the new opposite beam interpolation, and the filter-like interpolation of high-density interpolation).

The X-ray CT apparatus of the ninth embodiment produces a raw data of imaginary conventional scanning and subjects it to filtering or weighted addition.

Figure 10A:
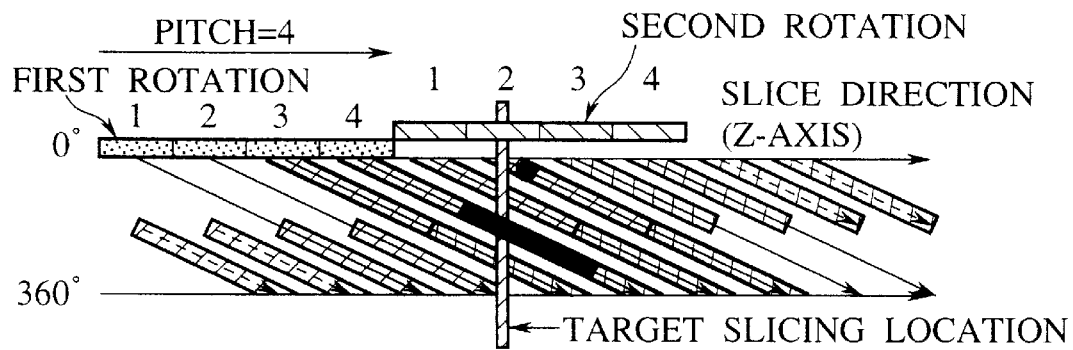
FIGS. 10A and 10B are scan diagrams in which a helical scanning of opposite beams is carried out with pitch=4 in a four-row multi-slice CT mode.
Figure 10B:
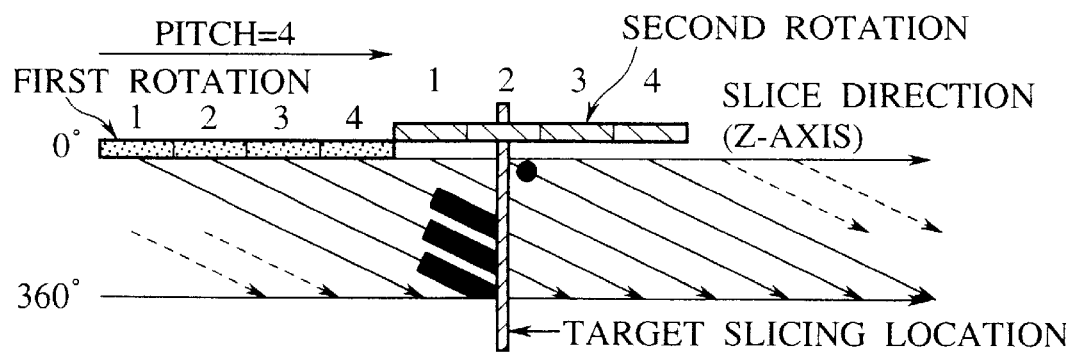

Similar to the apparatus shown in FIG. 11, the X-ray CT apparatus of the ninth embodiment comprises a system controller 11, a gantry/couch controller 13, a couch driver 15, an X-ray controller 17, a high-voltage generator 19, an X-ray source or X-ray tube 21 having an X-ray focal point, a detector 23, a gantry 25, a DAS 27, an interpolator 29, an image reconstructor 31, and a display 33. The detector 23 is of a four-row multi-slice type such as shown in FIG. 10B.

The system controller 11 delivers to the gantry/couch controller 13 a gantry/couch control signal indicative of the dose of X-ray, the slice thickness T, the helical pitch P, and the rotating speed out of the requirements entered through an entry device not shown. Also, supplied from the system controller 11 are an X-ray beam generation control signal for controlling the generation of X-ray beam to the X-ray controller 17, an detection control signal for timing the detection of X-ray beam and a data collection control signal for collection of data to the DAS 27, and an interpolation control signal to the interpolator 29. The gantry/couch controller 13 is responsive to the gantry/couch control signal from the system controller 11 for rotating the gantry 25 and delivering a couch drive signal to the couch driver 15.

The X-ray controller 17 is responsive to the X-ray beam generation control signal from the system controller 11 for timing the generation of a high voltage of the high-voltage generator 19. The high-voltage generator 19 upon receiving the X-ray control signal from the X-ray controller 17 supplies the high voltage to the X-ray source 21 for irradiation of an X-ray beam.

The X-ray source 21 is driven by the high voltage from the high-voltage generator 19 thus irradiating the X-ray beam.

The detector 23 is provided for detecting the X-ray beam irradiated from the X-ray source 21 and passed through an object to be examined.

The X-ray source 21 and the detector 23 are mounted on the gantry 25. The gantry 25 is driven by a gantry drive mechanism not shown for rotating the X-ray source 21 and the detector 23 about the center of rotation.

The DAS 27 is responsive to the data collection control signal from the system controller 11 for sampling data from X-ray signal outputs of the detector 23 and subjecting it to various processes including X-ray intensity compensation and detector sensitivity compensation to generate a raw data.

Figure 45:
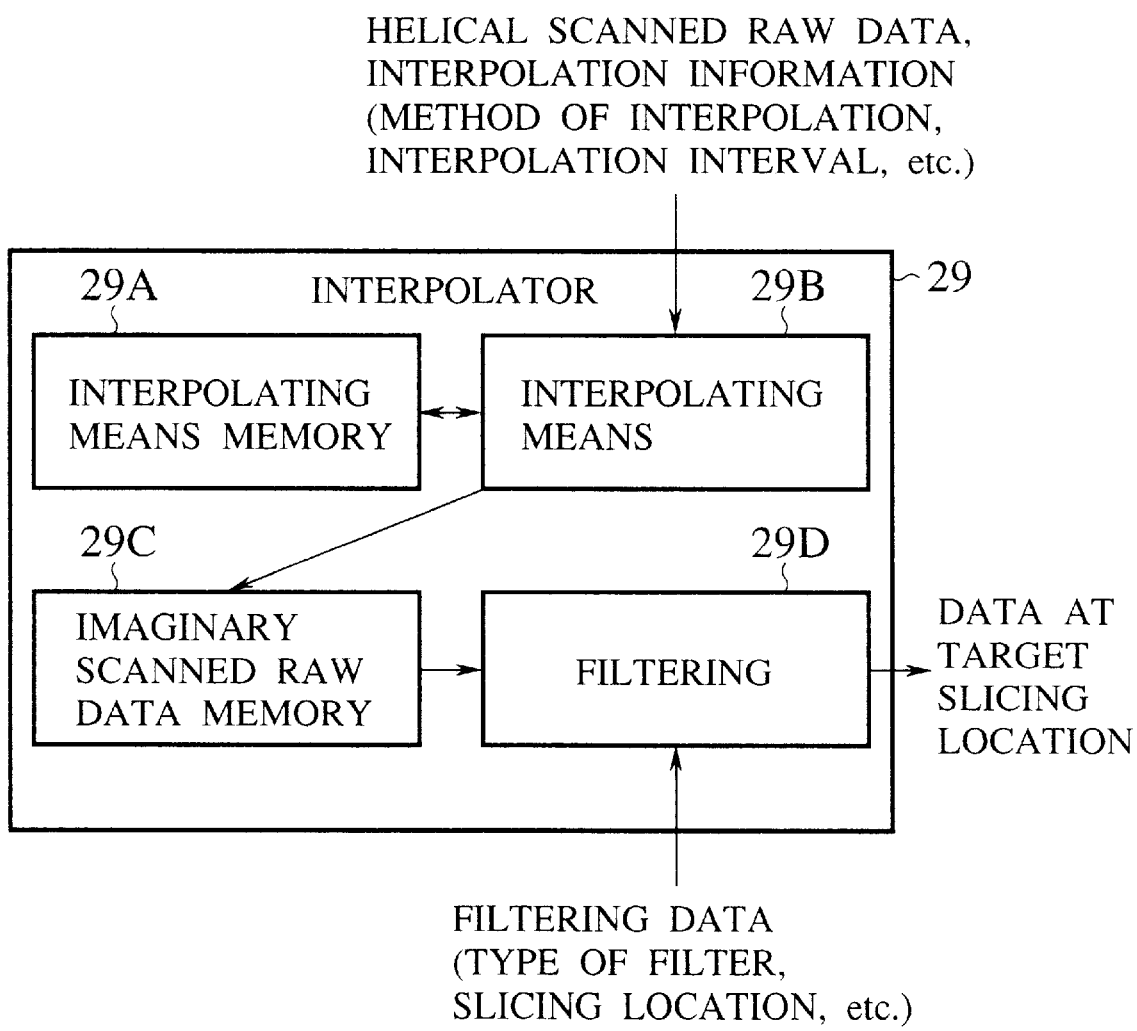
FIG. 45 is a block diagram of an interpolator.

The DAS 29 comprises, as best shown in FIG. 45, an interpolating means memory storage 29A for storing various interpolation means including the new opposite beam interpolation, adjacent interpolation, and non-linear interpolation, an interpolating means 29B for producing an imaginary scanned raw data (referred to as an imaginary scanned raw data hereinafter) by interpolation of a selected type between the raw data sampled by helical scanning, an imaginary scanned raw data storage 29C for storing the imaginary scanned raw data interpolated at small intervals, and a filter processor 29D for filtering the imaginary scanned raw data.

The image reconstructor 31 reconstructs a visual image from the filtered data at the target slicing location, using a predetermined reconstructing mode.

The image reconstructed by the image reconstructor 31 is then displayed on a monitor screen, not shown, of the display 33.

Figure 46:
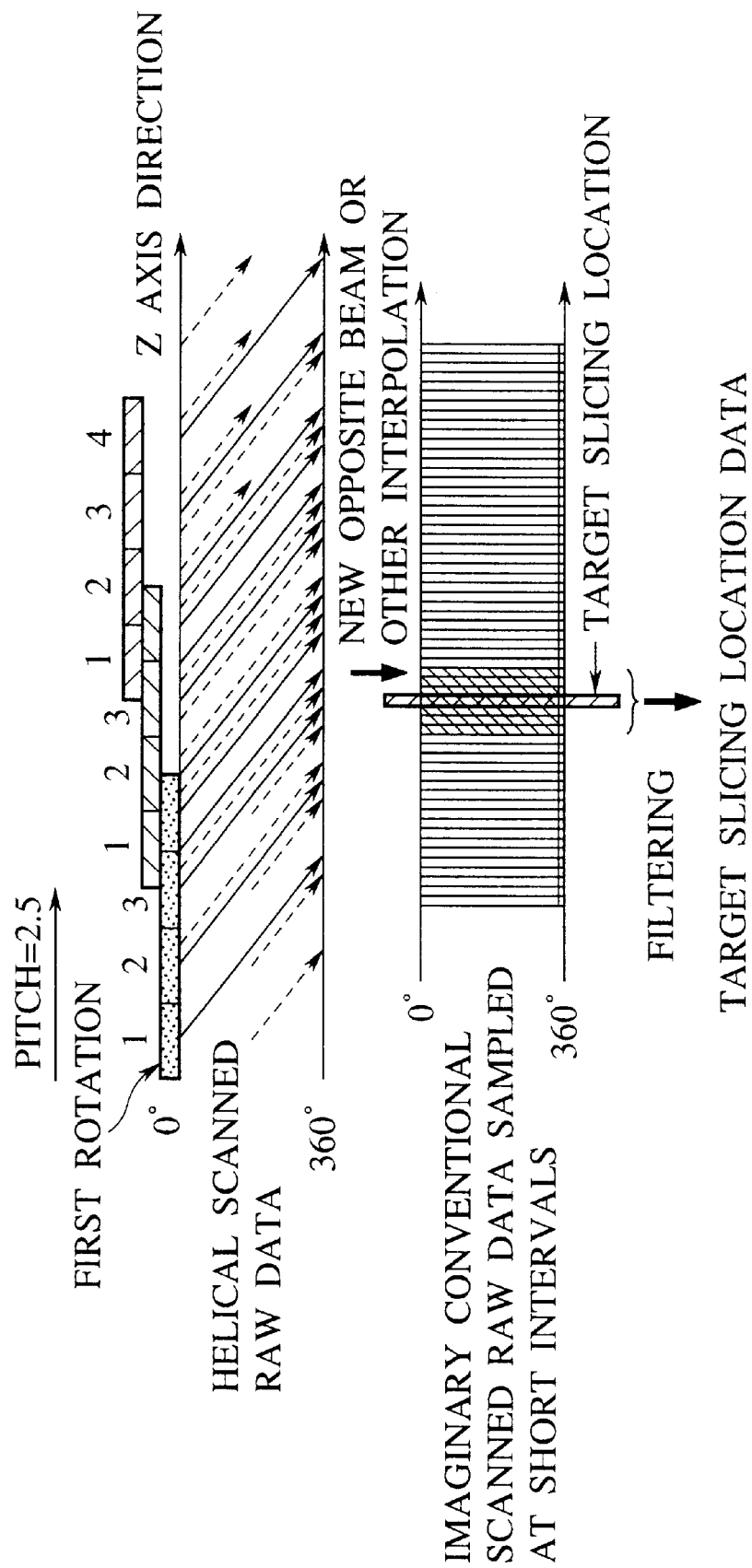
FIG. 46 is a diagram showing a helical scanned raw data sampled by the four-row multi-slice CT scanning with P=2.5 and an imaginary conventional scanned raw data produced from the helical scanned raw data.
Figure 47:
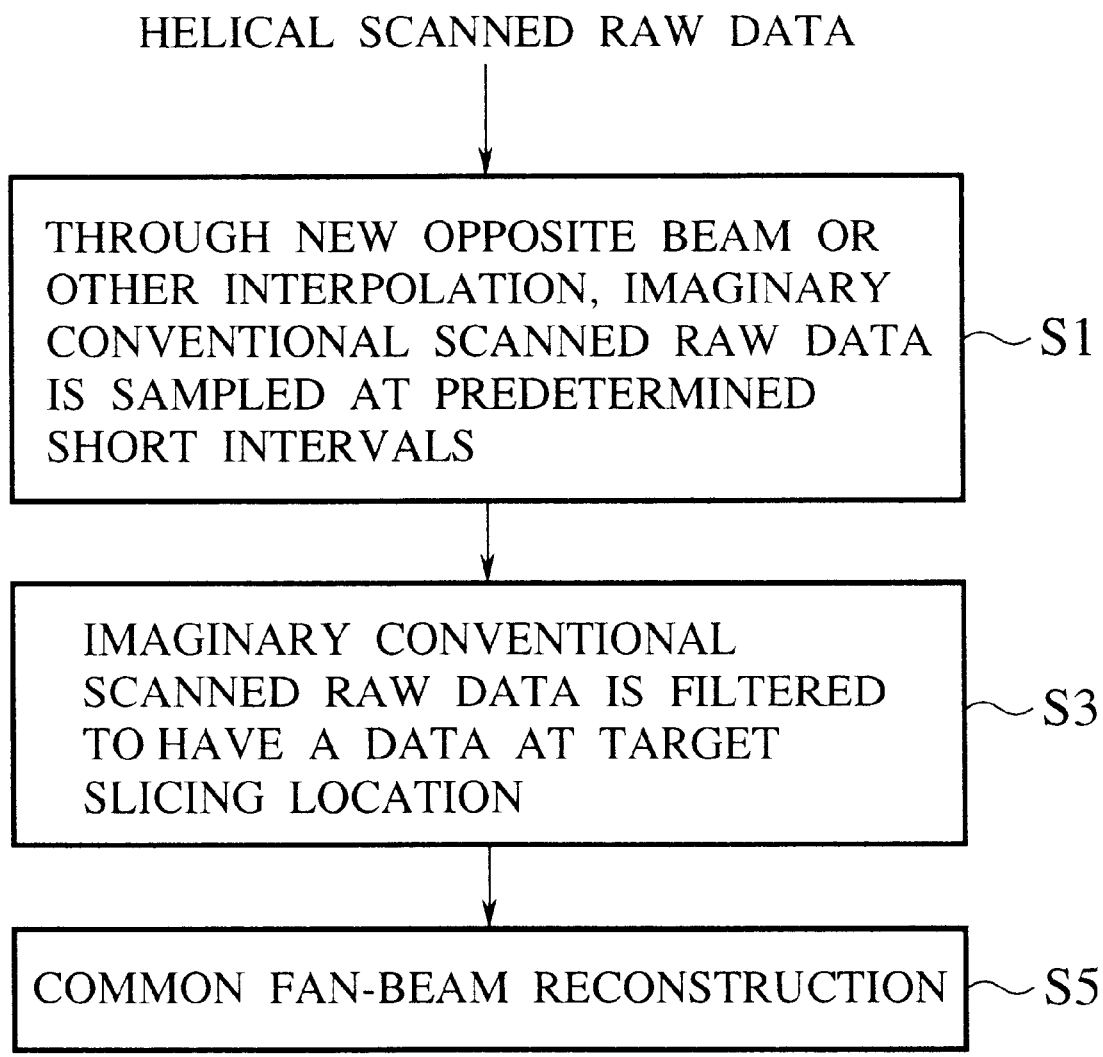
FIG. 47 is a flowchart showing the specific action of a ninth embodiment.

The action of the X-ray CT apparatus of the ninth embodiment is explained referring to FIGS. 46 and 47 in which a primary action of the X-ray CT apparatus of the ninth embodiment is illustrated.

The interpolating means storage 29A of the interpolator 29 reads out and sends one of the predetermined interpolating methods to the interpolating means 29B which in turn carries out an action of the predetermined interpolation to produce the imaginary scanned raw data which are imaginary conventional scanned data at corresponding slicing locations spaced at the small intervals as shown at the lower in FIG. 46 (Step S1 of FIG. 47). The imaginary scanned raw data are then stored in the imaginary scanned raw data storage 29C in relation to their slicing locations. The system controller 11 permits deletion of unwanted storage data or overwriting for saving the memory area.

The image reconstructor 31 accesses the interpolator 29 for having the imaginary scanned raw data at the corresponding slicing locations. In response, the filter processor 29D of the interpolator 29 reads out one or more of the imaginary scanned raw data at the corresponding slicing location from the imaginary scanned raw data storage 29C, subjects the data to its filtering action to have a requested data at the target slicing location, and delivers the requested data to the image reconstructor 31 (Step S3). Upon receiving the requested data at the target slicing location, the image reconstructor 31 processes it by a common fan-beam reconstruction thus reproducing a desired image (Step S5).

Figure 48:
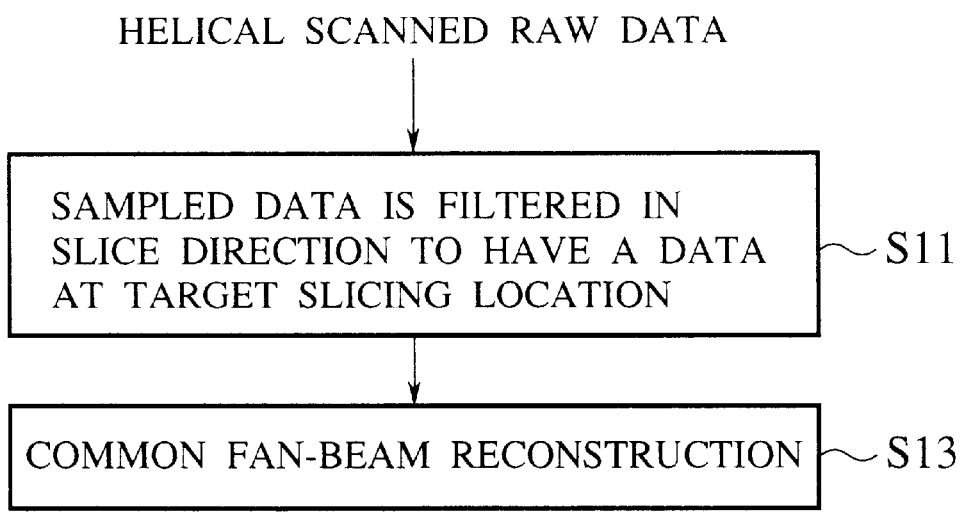
FIG. 48 is a flowchart showing the specific action of a seventh embodiment.
Figure 49:
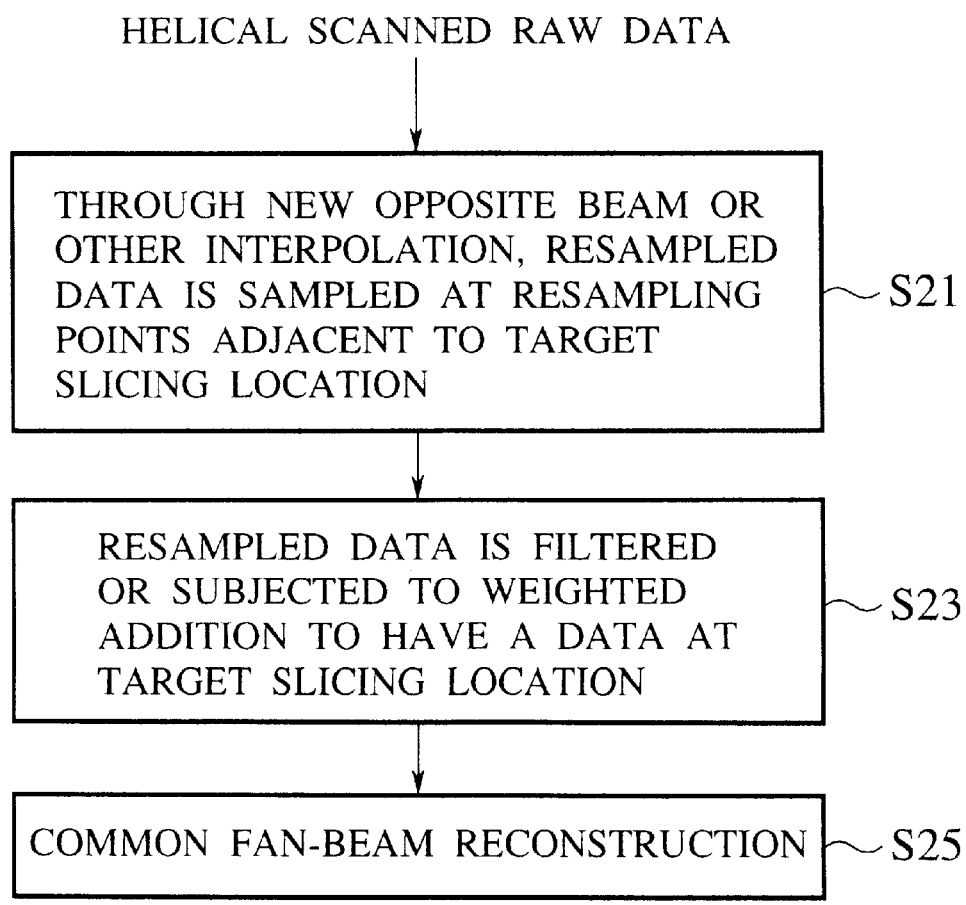
FIG. 49 is a flowchart showing the specific action of an eighth embodiment.

According to the seventh embodiment, the raw data is read out and its sampled data are filtered to have a desired data at the target slicing location (Step S11) before a common fan-beam reconstruction is carried out (Step S13) as shown in FIG. 48. The eighth embodiment produces data at the imaginary slicing locations adjacent to the target slicing location from the helical scanned raw data and subjects them to the new opposite beam interpolation or the like thus having an imaginary data (Step S21), as shown in FIG. 49. This is followed by processing the imaginary data with filtering or weighted addition to have a desired data at the target slicing location (Step S23) and performing a common fan-beam reconstruction (Step S25). In both the embodiments, the image reconstruction can be conducted with the helical scanned raw data stored in the relevant storage.

The ninth embodiment however allows the raw data of imaginary conventional scanned type to be produced at a high density by conventional scanning of the helical scanned raw data at the small intervals and, in response to the requirement of reconstruction, to be subjected to the weighted addition or filtering before the reconstruction of an image.

It should be noted that the interpolation for having the imaginary conventional scanned raw data is arbitrarily selected form the new opposite beam interpolation, adjacent interpolation, and other non-linear interpolation. Also, the number of rows of the detector elements and the helical pitch are optional.

Figure 50:
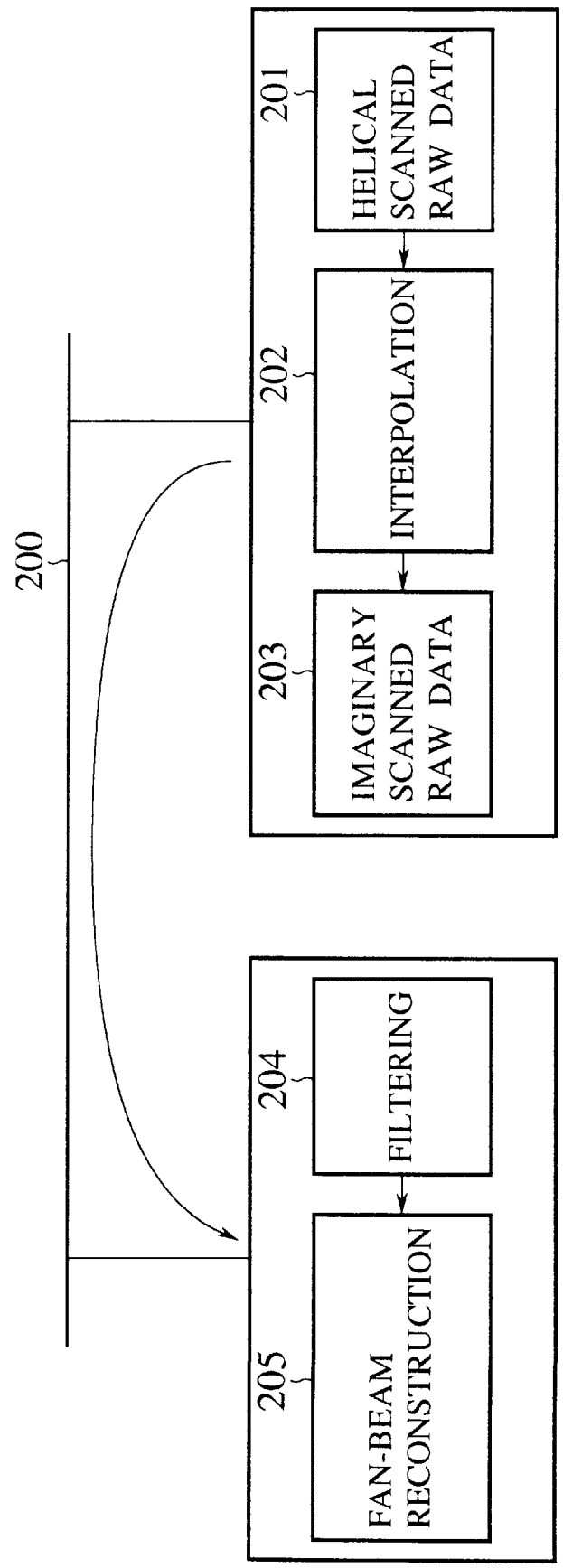
FIG. 50 is a hardware view of the specific action of the ninth embodiment.

FIG. 50 illustrates a hardware arrangement of the ninth embodiment in which a helical scanned raw data 201 is fed to an interpolator 202 where it is subjected to the new opposite beam interpolation or the like and saved temporarily as an imaginary scanned raw data 203 at a high density. When the imaginary scanned raw data 203 is accessed, it is transmitted at a high speed via a bus 200 to another hardware for filtering 204. The filtered data 204 is subjected to fan-beam reconstruction for having a reconstructed image.

As described, according to the ninth embodiment, the raw data of imaginary conventional scanned type are produced at a high density by conventional scanning of the helical scanned raw data at the small intervals and processed for the reconstruction of an image, whereby the image will be improved in quality as well as reconstructed at a higher speed.

Figure 51:
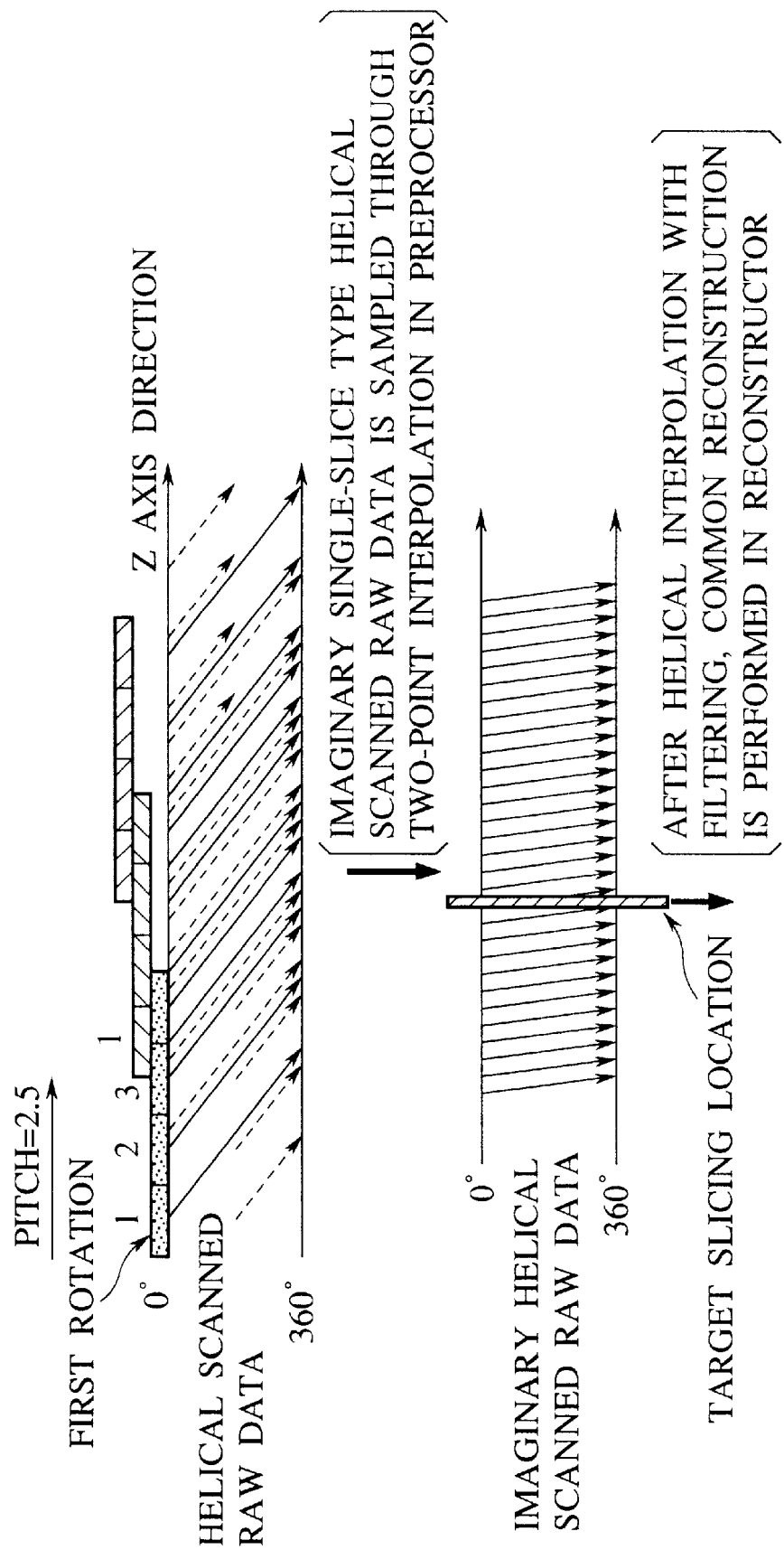
FIG. 51 is an explanatory view showing sampling of an imaginary helical scanned raw data in the imaginary single-slice CT mode.

The filter-like interpolation of the imaginary helical scanned raw data is now explained. In the ninth embodiment, the process is similar to that shown in FIG. 46 where the imaginary conventional scanned raw data are sampled at wider intervals and may be carried out at shown in FIG. 51. The process shown in FIG. 51 produces imaginary helical scanned raw data of the imaginary single-slice CT mode.

For reconstruction, the raw data of the imaginary single-slice CT mode is read for several rotations depending on the filtering size and subjected to particular weighted addition where the filtering and interpolation are carried out at once.

A tenth embodiment of the X-ray CT apparatus of the present invention will be described (employing a combination of p=2.5, the new opposite beam interpolation, and the filter-like interpolation of voxel filtering). The construction of the X-ray CT apparatus of the tenth embodiment is substantially identical to that of the ninth embodiment and its primary part only is explained.

Figure 52A:
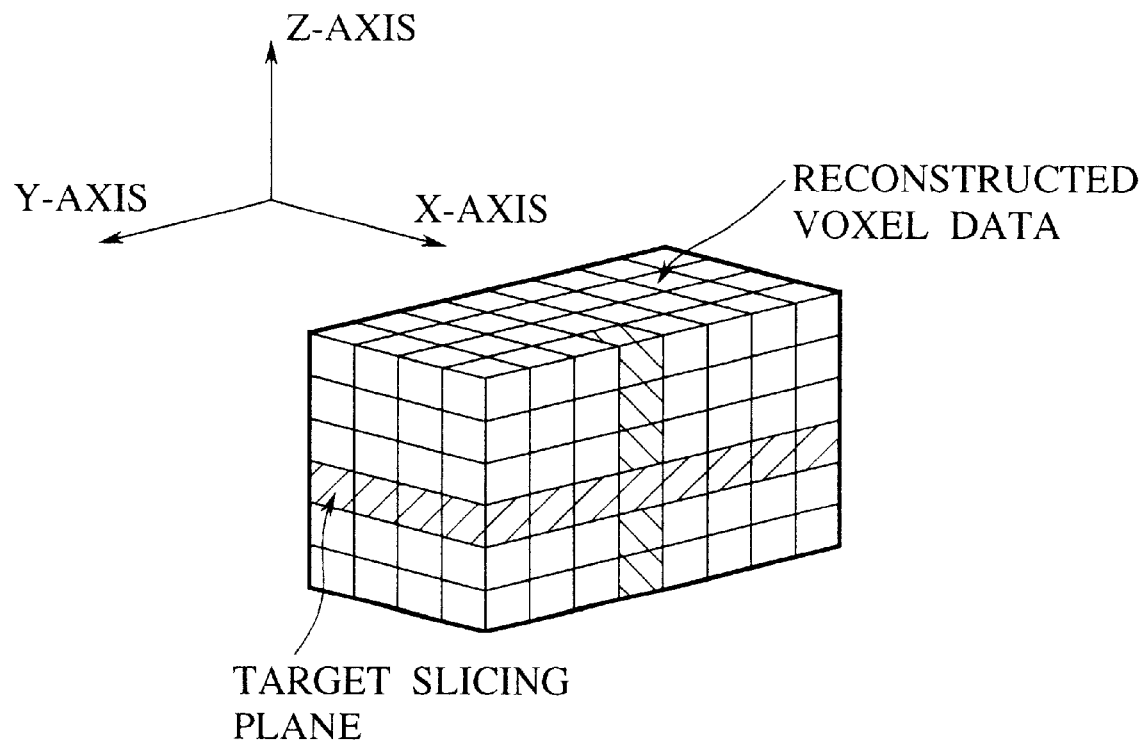
FIGS. 52A and 52B are schematic views of a tenth embodiment in which the filter-like interpolation is made by voxel filtering.

In the X-ray CT apparatus of the tenth embodiment, the filtering or weighted addition described in the seventh to ninth embodiments is applied to an image (of voxels) reconstructed at small intervals. FIG. 52 is a schematic view of the tenth embodiment and FIG. 53 is a flowchart showing a substantial procedure according to the tenth embodiment.

First of all, interpolation at target slicing location Z=Z0 is executed by adjacent interpolation or new opposite beam interpolation, and then convolution operation with a reconstruction function and back projection operation are executed as same as the conventional way so as to have the first reconstructed image.

Next, the procedure proceeds to producing interpolated data at the target slicing location $Z=Z(i)=Z0+\delta Z(i)$ spaced along the Z axis by $\delta Z(i)$ from the target slicing location Z=Z0 is performed using equations (13) and (14). As the result, the first image reconstruction is done for n images (Step S31 of FIG. 53). A resultant voxel data is shown in FIG. 52A.

$$IMAGE(Z(i))=\text{BACK PROJECTION} [\text{CONVOLUTION}\{\text{ADJACENT INTERPOLATION}(Z(i))\}] \quad (13)$$

$$Z(i)=Z0+\delta Z(i) \quad (14)$$

Figure 52B:
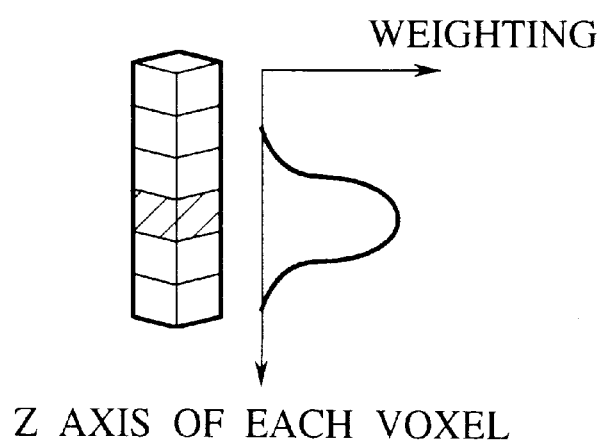
Figure 53:
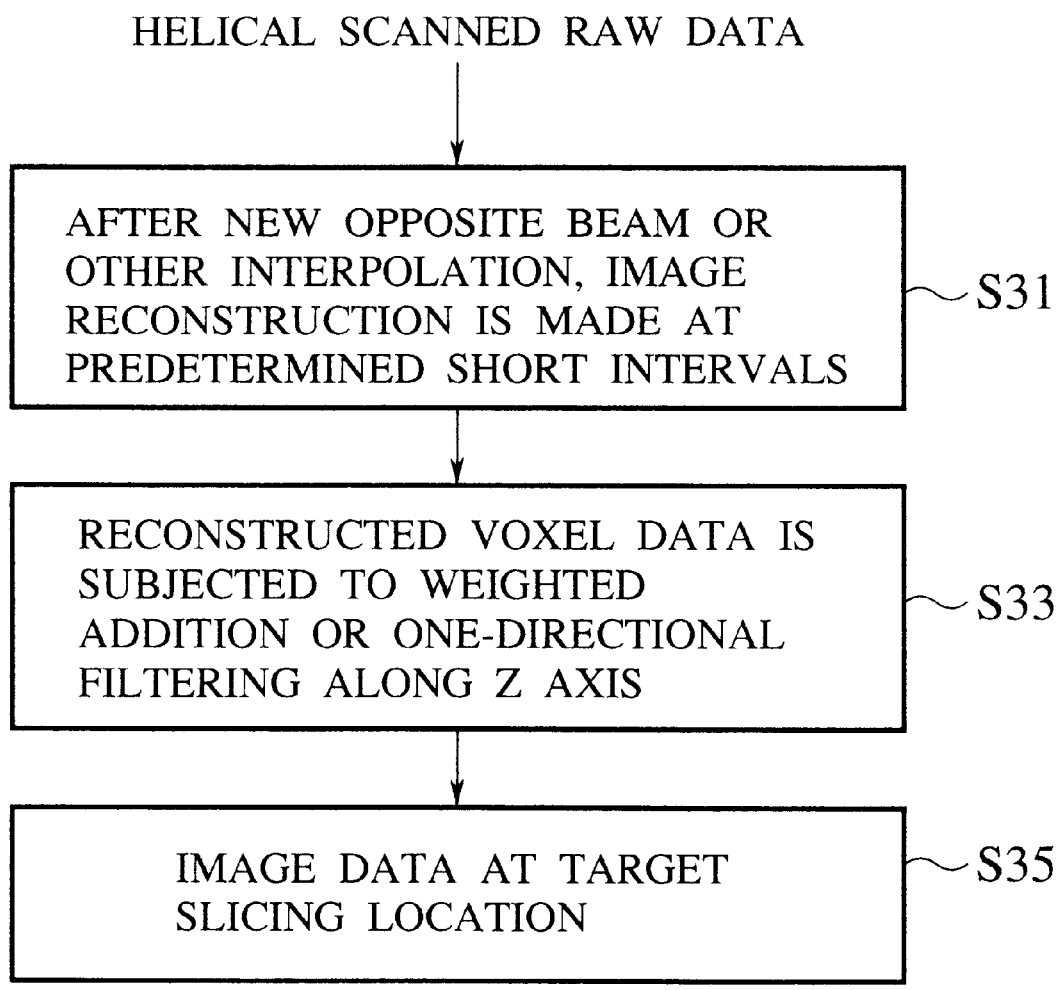
FIG. 53 is a flowchart showing the specific action of the tenth embodiment.

The n reconstructed image IMAGE(x, y, z) or reconstructed voxel data is then subjected to one-directional weighted addition of (x, y) coordinate values along the Z axis of filtering shown in FIG. 52B, using an equation (15) or (16) respectively, hence producing an image data at the target slicing location Z=Z0 (Step S33 and S35).

$$IMAGE(Z0) = \sum_{}^{n} (W(i) \cdot IMAGE(Z(I))) \quad (15)$$

$$IMAGE(Z0)=FILTERING(IMAGE(Z(1)), IMAGE(Z(2)), IMAGE(Z(3)), \ldots, IMAGE(Z(n))) \quad (16)$$

The filter shape, the number of rows of the detector elements, and the helical pitch are not limited to those of the embodiment and other appropriate variations will be possible.

As described, the X-ray CT apparatus of the tenth embodiment allows the preliminary image (of voxels) reconstructed at smaller intervals to be subjected to the filtering or weighted addition, thus enhancing the quality of a reconstructed image.

Figure 54A:
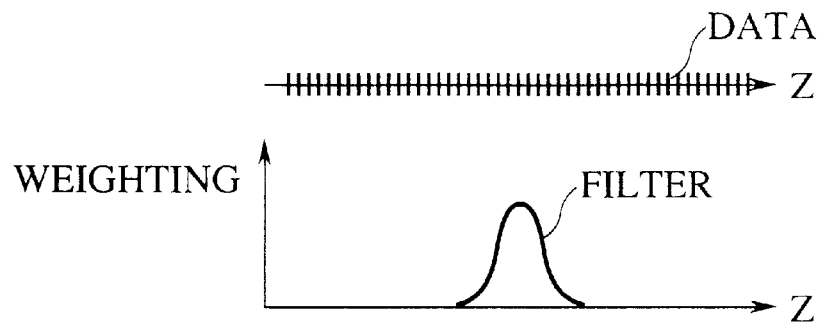
FIGS. 54A to 54C are explanatory views showing a series of filtering actions with a plurality of filter segments divided from one filter.
Figure 54B:
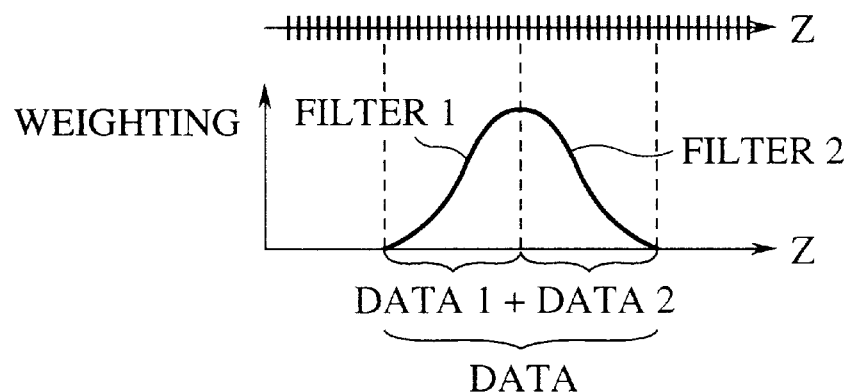
Figure 54C:
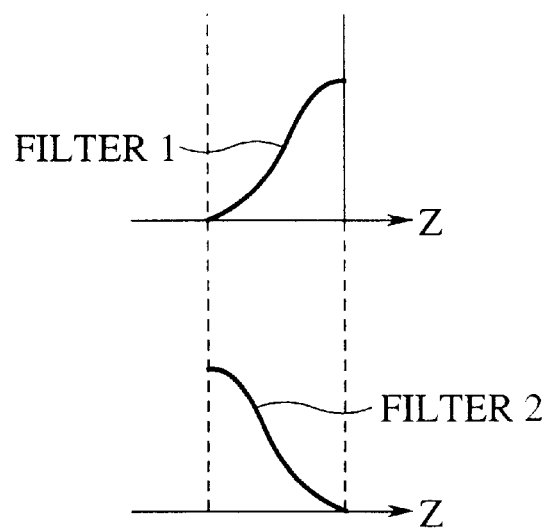

In the seventh to tenth embodiments, when the hardware or software has a common filtering size such as shown in FIG. 54A and an extended filtering width along the Z axis such as shown in FIG. 54B, it may comprise two filtering sections as shown in FIG. 54C. Data filtered by the two sections separately may be combined later during the interpolation or the reconstruction of an image. Also, the filter is not limited to such two sections as shown in FIG. 54C but may be composed of three or more filtering sections.

The filter operation from the seventh to the tenth embodiments is applicable to a single slice CT apparatus.

What is claimed is:

1. An X-ray CT scanning apparatus having an X-ray source for irradiating a beam of X-ray to an object to be examined, a detecting means provided with at least two rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction so that the real data sampled by the detecting means is not identical in the sweep pattern to its opposite data.

2. An X-ray CT scanning apparatus according to claim 1, wherein the real data is not identical in the sweep pattern to its opposite data in a specific channel.

3. An X-ray CT scanning apparatus according to claim 2, wherein the specific channel is a significant channel essential for the purpose of examination.

4. An X-ray CT scanning apparatus having an X-ray source for irradiating a beam of X-ray to an object to be examined, a detecting means provided with at least two rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and selecting two data located on both sides of the target slicing location from groups of the real data and their opposite data sampled by the detecting means and producing a desired data at the target slicing location by interpolation between the two selected data, wherein the selection of the two data is independently carried out in each channel.

5. An X-ray CT scanning apparatus according to claim 4, wherein the scanning of the object in the helical direction is conducted so that the real data is not identical in the sweep pattern to its opposite data.

6. An X-ray CT scanning apparatus having an X-ray source for irradiating a beam of X-ray to an object to be examined, a detecting means provided with at least two rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and selecting two data located on both sides of the target slicing location from groups of the real data and their opposite data sampled by the detecting means and producing a desired data at the target slicing location by interpolation between the two selected data, wherein the scanning of the object in the helical direction is conducted so that the real data is not identical in the sweep pattern to its opposite data.

7. An X-ray CT scanning apparatus having an X-ray source for irradiating a beam of X-ray to an object to be examined, a detecting means provided with rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and filtering a group of the real data and their opposite data sampled by the detecting means to have a desired data at the target slicing location, wherein the filtering comprises the steps of selecting a desired number of data from a group of the real data and their opposite data sampled by the detecting means, producing a corresponding number of data at imaginary slicing locations by interpolation between the selected data, and subjecting the data at the imaginary slicing locations to weighted addition.

8. An X-ray CT scanning apparatus according to claim 7, wherein the detecting means is provided with at least two rows of detector elements.

9. An X-ray CT scanning apparatus according to claim 8, wherein the interpolation is performed between two data which are located on both sides of each of the imaginary slicing locations and selected from the group of the real data and their opposite data sampled by the detecting means.

10. An X-ray CT scanning apparatus according to claim 8, wherein the scanning of the object in the helical direction is conducted so that the real data is not identical in the sweep pattern to its opposite data.

11. An X-ray CT scanning apparatus according to claim 10, wherein the interpolation is performed between two data which are located on both sides of each of the imaginary slicing locations and selected from the group of the real data and their opposite data sampled by the detecting means.

12. An X-ray CT scanning apparatus having an X-ray source for irradiating a beam of X-ray to an object to be examined, a detecting means provided with rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and filtering a group of the real data and/or their opposite data sampled by the detecting means to have a desired data at the target slicing location, wherein the filtering is a process of weighted addition, and the detecting means is provided with at least two rows of detector elements, and wherein the scanning of the object in the helical direction is conducted so that the real data is not identical in the sweep pattern to is opposite data.

13. An X-ray CT scanning apparatus having X-ray source for irradiating a beam of X-ray to an object to be examined, a detecting means provided with rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and filtering a group of the real data and their opposite data sampled by the detecting means to have a desired data at the target slicing location, wherein the filtering comprises the steps of interpolating among a group of the real data and their opposite data sampled by the detecting means to produce imaginary helical scanned real data of an imaginary single-slice CT mode, and producing a data at the target slicing location from the imaginary helical scanned real data and their opposite data.

14. An X-ray CT scanning apparatus according to claim 13, wherein the interpolation is performed between two data which are located on both sides of each of scanning locations for the imaginary helical scanning and selected from the group of the real data and their opposite data sampled by the detecting means.

15. An X-ray CT scanning apparatus according to claim 13, wherein the scanning of the object in the helical direction is conducted so that the real data is not identical in the sweep pattern to its opposite data.

16. An X-ray CT scanning apparatus according to claim 15, wherein the interpolation is performed between two data which are located on both sides of each of scanning locations for the imaginary helical scanning and selected from the group of the real data and their opposite data sampled by the detecting means.

17. An X-ray CT scanning apparatus having an X-ray source for irradiating a beam of X-ray to an object to be examined, a detecting means provided with rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and filtering a group of the real data and/or their opposite data sampled by the detecting means to have a desired data at the target slicing location, wherein the detecting means is provided with at least two rows of detector element, and wherein the scanning of the object in the helical direction is conducted so that the real data is not identical in the sweep pattern to its opposite data.

18. An X-ray CT scanning apparatus having an X-ray source for irradiating a beam of X-ray to an object to be examined, a detecting means provided with rows of detector elements for detecting the X-ray beam to have a real data, and a couch traveling means for traveling in an axial direction of the body of the object a couch on which the object is placed, characterized by:

irradiating the X-ray beam from the X-ray source which is being rotated and simultaneously, traveling the couch with the couch traveling means to scan the object in a helical direction; and filtering a group of the real data and their opposite data sampled by the detecting means to have a desired data at the target slicing location, wherein the filtering comprises the steps of interpolating among a group of the real data and their opposite data sampled by the detecting means to produce imaginary conventional scanned real data, and producing a data at the target slicing location from the imaginary conventional scanned real data.

19. An X-ray CT scanning apparatus according to claim 18, wherein the detecting means is provided with at least two rows of detector elements.

20. An X-ray CT scanning apparatus according to claim 19, wherein the interpolation is performed between two data which are located on both sides of each of scanning locations for the imaginary conventional scanning and selected from the group of the real data and their opposite data sampled by the detecting means.

21. An X-ray CT scanning apparatus according to claim 19, wherein the scanning of the object in the helical direction is conducted so that the real data is not identical in the sweep pattern to its opposite data.

22. An X-ray CT scanning apparatus according to claim 21, wherein the interpolation is performed between two data which are located on both sides of each of scanning locations for the imaginary conventional scanning and selected from the group of the real data and their opposite data sampled by the detecting means.

23. An X-ray CT scanning apparatus according to any of claims 7, 18–22, 8, 16, wherein the filtering is implemented by a plurality of filter segments divided along the direction of slices from a filter for filtering a series of the data separately and combining them.

24. An X-ray CT scanning apparatus having an X-ray source for irradiating a beam of X-ray to an object to be examined, a detecting means provided with at least two rows of detector elements for detecting the X-ray beam to have a real data, a couch traveling means for traveling in an axial direction of the body of the object a couch on which the object is placed, and an image reconstructing device for reconstructing a visual image from a group of the real data and their opposite data sampled by the detecting means, characterized by:

irradiating the X-ray beam from the X-ray source which is being rotated and simultaneously, traveling the couch with the couch traveling means to scan the object in a helical direction; and subjecting a group of the real data and their opposite data sampled by the detecting means to first image reconstruction for producing a series of preparatory voxel data and subjecting the preparatory voxel data to weighted addition along the direction of slices thus to produce the sliced image at the target slicing location.

* * * * *

UNITED STATES PATENT AND TRADEMARK OFFICE
CERTIFICATE OF CORRECTION

PATENT NO. : 5,974,108
DATED : October 26, 1999
INVENTOR(S) : Taguchi et al.

It is certified that error appears in the above-identified patent and that said Letters Patent is hereby corrected as shown below:

Column 28,
Line 53, change "is" to -- it's --.

Signed and Sealed this

Sixteenth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 5,974,108
DATED : October 26, 1999
INVENTOR(S) : Taguchi et al.

It is certified that error appears in the above-identified patent and that said Letters Patent is hereby corrected as shown below:

Column 28,
Line 53, change "it's" to -- its --.

Signed and Sealed this

Twenty-eighth Day of June, 2005

JON W. DUDAS
*Director of the United States Patent and Trademark Office*